(12) United States Patent
Jinno et al.

(10) Patent No.: US 8,512,316 B2
(45) Date of Patent: *Aug. 20, 2013

(54) MANIPULATOR

(75) Inventors: Makoto Jinno, Tokyo (JP); Takamitsu Sunaoshi, Yamato (JP)

(73) Assignee: Terumo Kabushiki Kaisha, Tokyo (JP)

( * ) Notice: Subject to any disclaimer, the term of this patent is extended or adjusted under 35 U.S.C. 154(b) by 967 days.

This patent is subject to a terminal disclaimer.

(21) Appl. No.: 12/432,511

(22) Filed: Apr. 29, 2009

(65) Prior Publication Data

US 2009/0216249 A1 Aug. 27, 2009

Related U.S. Application Data

(62) Division of application No. 11/390,458, filed on Mar. 28, 2006, now Pat. No. 7,540,867.

(30) Foreign Application Priority Data

Mar. 29, 2005 (JP) ................................. 2005-096115

(51) Int. Cl.
*A61B 19/00* (2006.01)
*B25J 17/02* (2006.01)

(52) U.S. Cl.
USPC .......................................... 606/1; 74/490.06

(58) Field of Classification Search
USPC ................. 74/490.01, 490.05–6; 901/14–16, 901/25, 28–29
See application file for complete search history.

(56) References Cited

U.S. PATENT DOCUMENTS

| | | | |
|---|---|---|---|
| 4,068,763 | A | 1/1978 | Fletcher et al. |
| 4,353,677 | A | 10/1982 | Susnjara et al. |
| 4,762,016 | A | 8/1988 | Stoughton et al. |
| 5,797,900 | A | 8/1998 | Madhani et al. |
| 5,817,119 | A | 10/1998 | Klieman et al. |
| 6,331,181 | B1 | 12/2001 | Tierney et al. |
| 6,394,998 | B1 | 5/2002 | Wallace et al. |
| 6,695,774 | B2 | 2/2004 | Hale et al. |
| 6,746,443 | B1 | 6/2004 | Morley et al. |
| 6,853,879 | B2 | 2/2005 | Sunaoshi |

(Continued)

FOREIGN PATENT DOCUMENTS

| | | |
|---|---|---|
| GB | 2 256 847 A | 12/1992 |
| JP | 57-156194 | 9/1982 |

(Continued)

OTHER PUBLICATIONS

Office Action issued on Aug. 10, 2010, in Japanese Patent Application No. 2007-332409 (with English-language Translation).

(Continued)

*Primary Examiner* — Sam Yao
*Assistant Examiner* — Scott T Luan
(74) *Attorney, Agent, or Firm* — Oblon, Spivak, McClelland, Maier & Neustadt, L.L.P.

(57) ABSTRACT

A manipulator has a treating portion, a driving portion which are connected by a connecting portion, a first pulley on which a first wire which passes through inside of the connecting portion and is driven by the driving portion is hung for rotation, and a main shaft portion which rotatably supports the treating portion around a main shaft along a direction different from a first rotor axis that the first pulley rotates, one end portion of which is fixed to the first pulley.

4 Claims, 36 Drawing Sheets

(56) References Cited

U.S. PATENT DOCUMENTS

| | | |
|---|---|---|
| 6,889,116 B2 | 5/2005 | Jinno |
| 6,993,413 B2 | 1/2006 | Sunaoshi |
| 6,994,716 B2 | 2/2006 | Jinno et al. |
| 2002/0040217 A1 | 4/2002 | Jinno |
| 2002/0103476 A1* | 8/2002 | Madhani et al. .......... 606/1 |
| 2002/0111621 A1 | 8/2002 | Wallace et al. |
| 2003/0100892 A1 | 5/2003 | Morley et al. |
| 2004/0266574 A1 | 12/2004 | Jinno et al. |
| 2004/0267406 A1 | 12/2004 | Jinno |
| 2005/0222587 A1 | 10/2005 | Jinno et al. |
| 2005/0234434 A1 | 10/2005 | Sunaoshi |
| 2009/0024123 A1* | 1/2009 | Young ................ 606/41 |
| 2009/0139364 A1* | 6/2009 | Forslund et al. .......... 74/490.06 |

FOREIGN PATENT DOCUMENTS

| | | |
|---|---|---|
| JP | 58-4385 | 1/1983 |
| JP | 61-68894 | 5/1986 |
| JP | 2001-277157 | 10/2001 |
| JP | 2002-102248 | 4/2002 |
| JP | 2003-61969 | 3/2003 |
| JP | 2003061969 A | 3/2003 |
| RU | 2063865 C1 | 7/1996 |
| SU | 704777 A | 12/1979 |
| SU | 334777 B | 5/1980 |
| SU | 1590370 A1 | 9/1990 |

OTHER PUBLICATIONS

Kouji Nishizawa, et al., "Development of Interference-Free Wire-Driven Joint Mechanism for Surgical Manipulator Systems", JSME Conference on Robotics and Mechatronics, 2003, pp. 1-2.

* cited by examiner

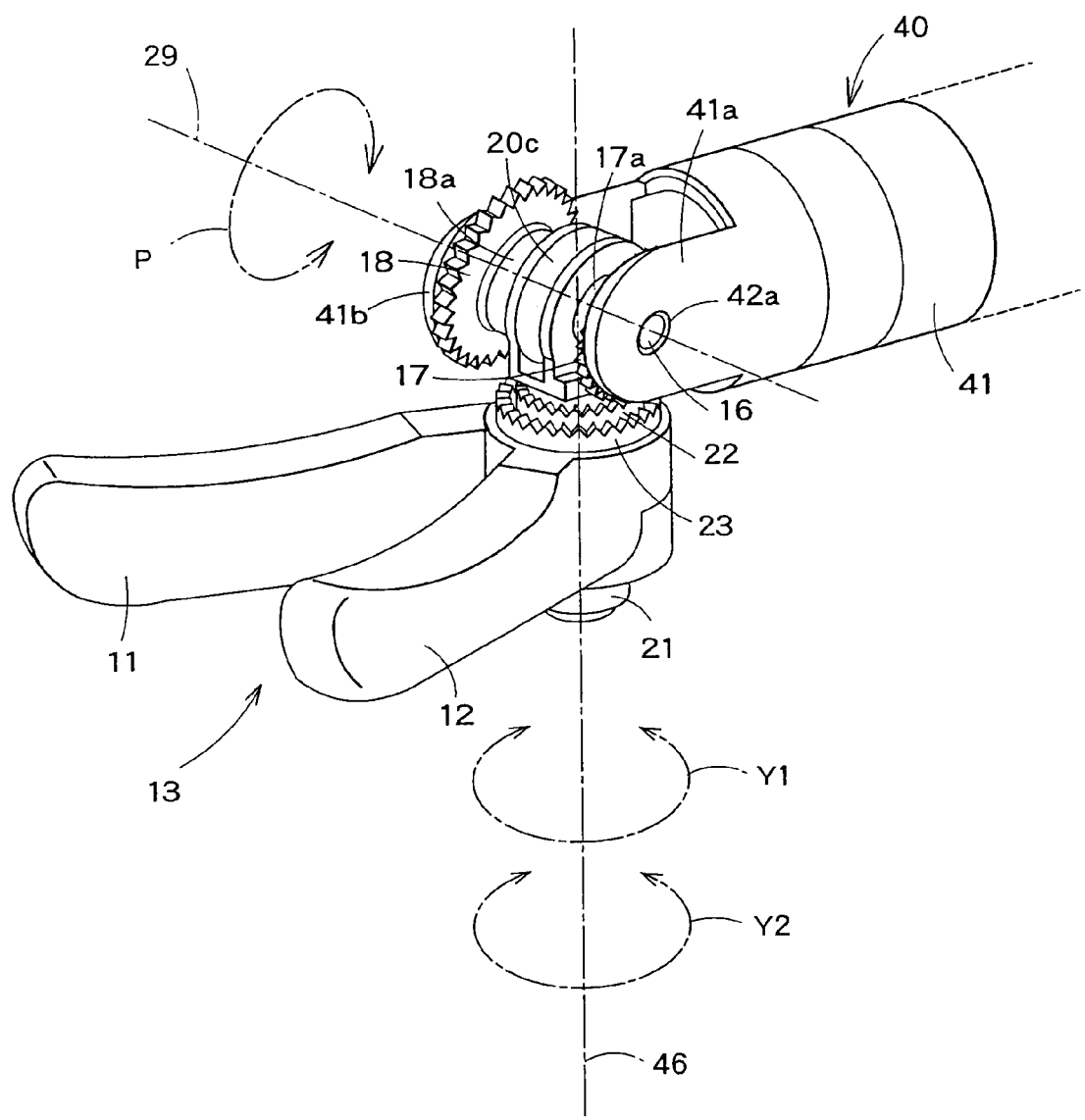
F I G. 2

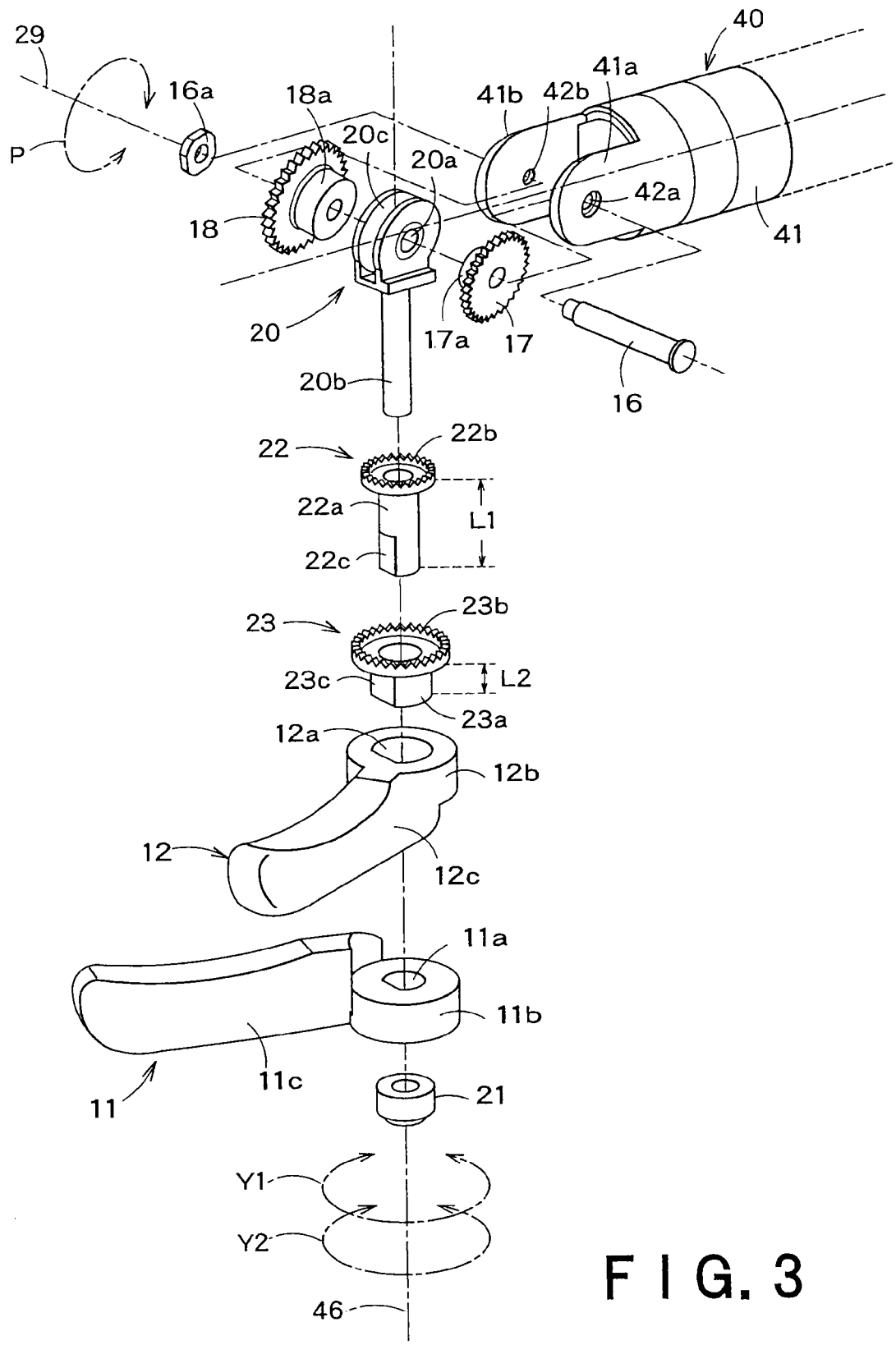
F I G. 3

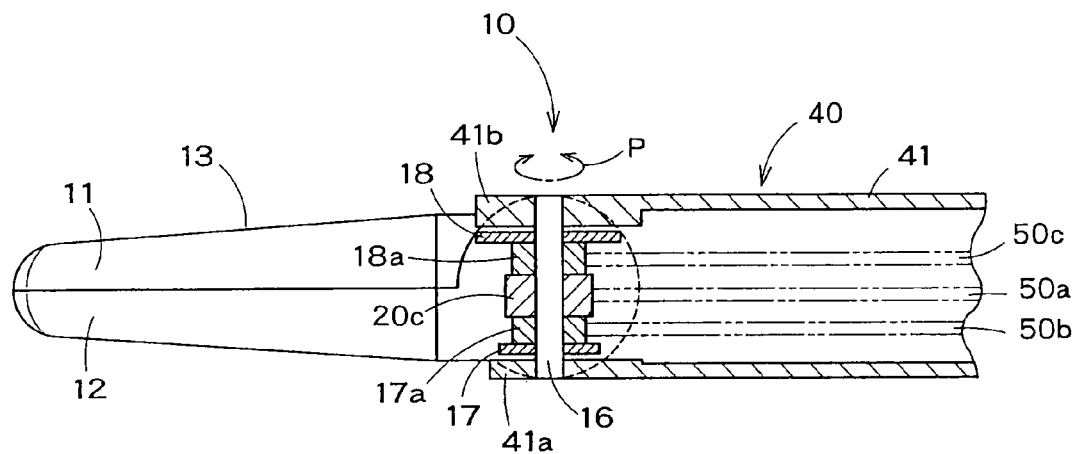
F I G. 4A
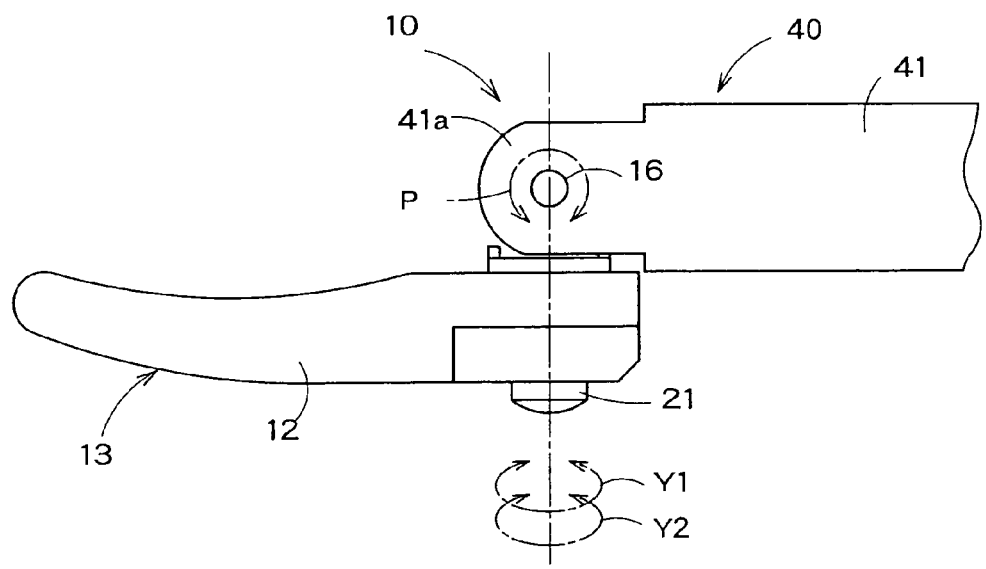
F I G. 4B

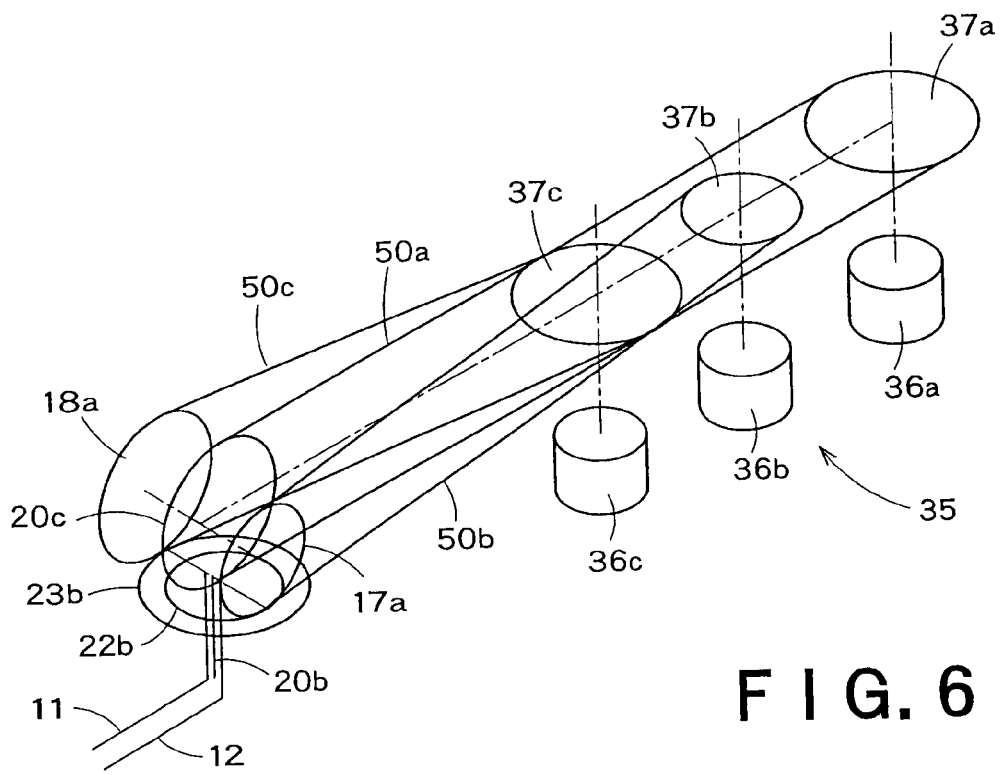
F I G. 6
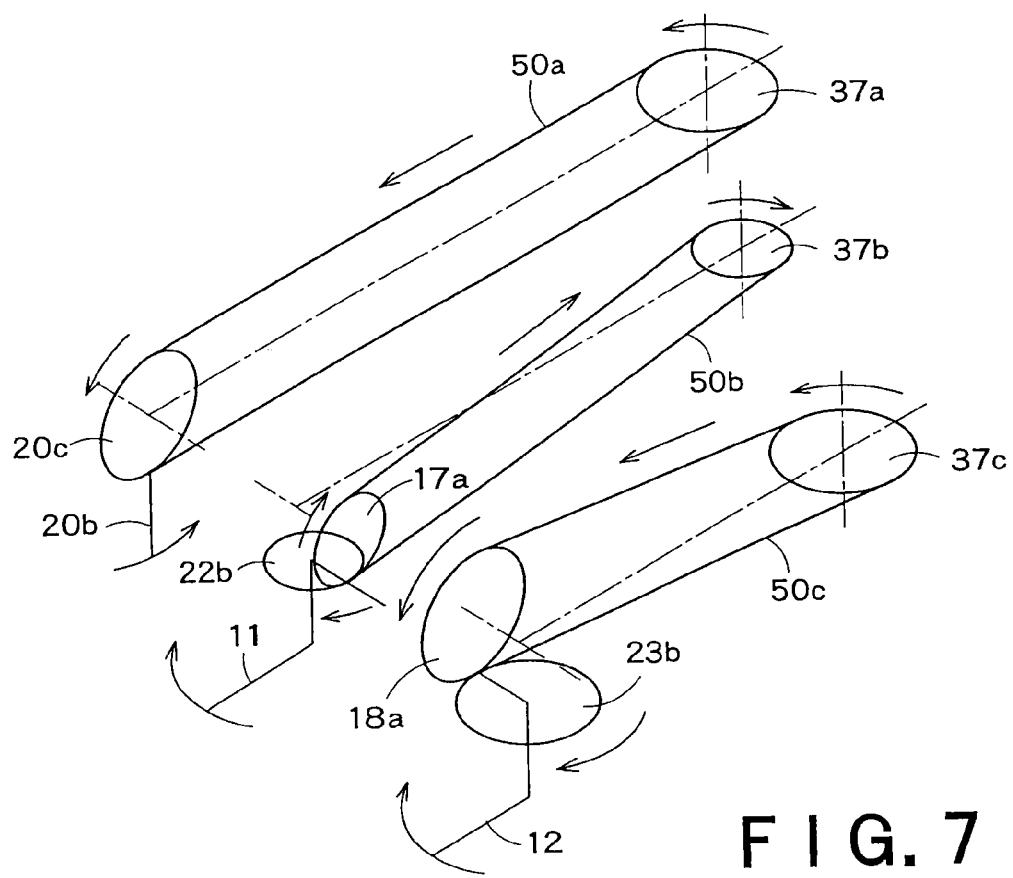
F I G. 7

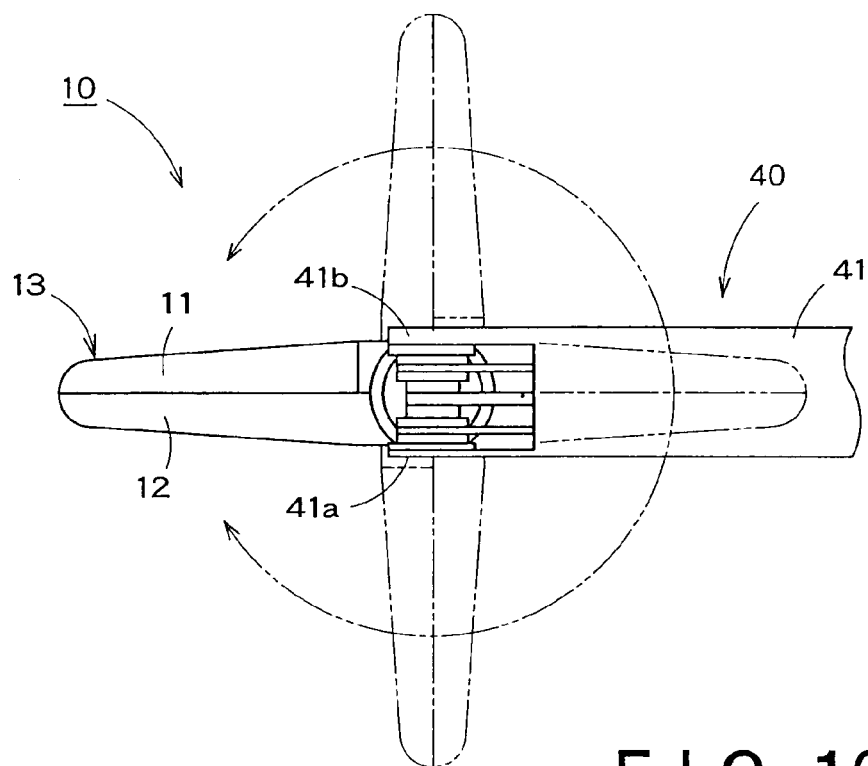
F I G. 10
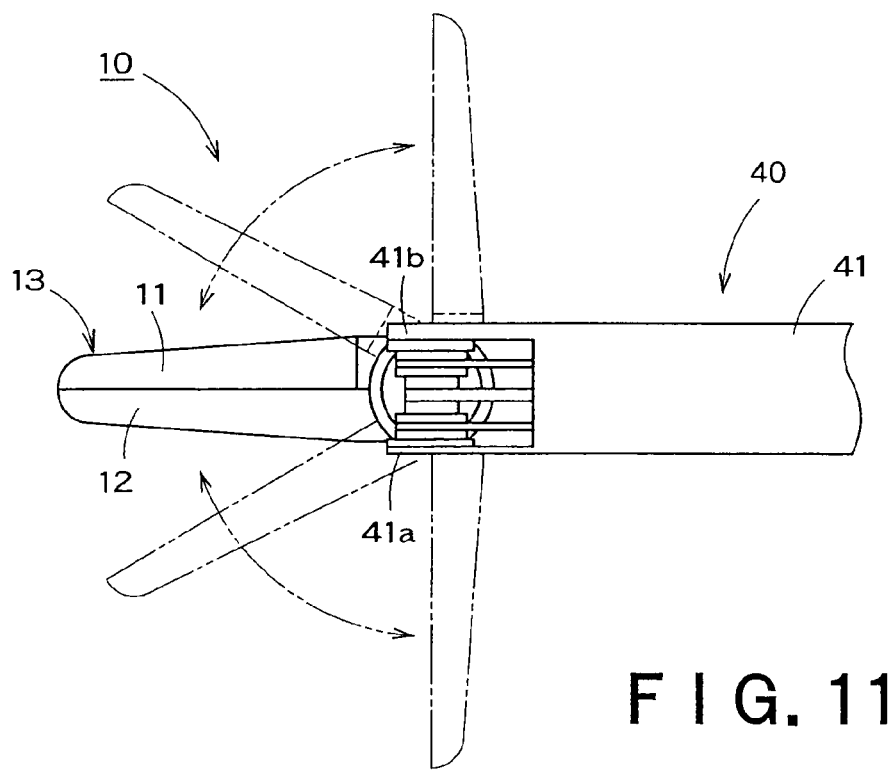
F I G. 11

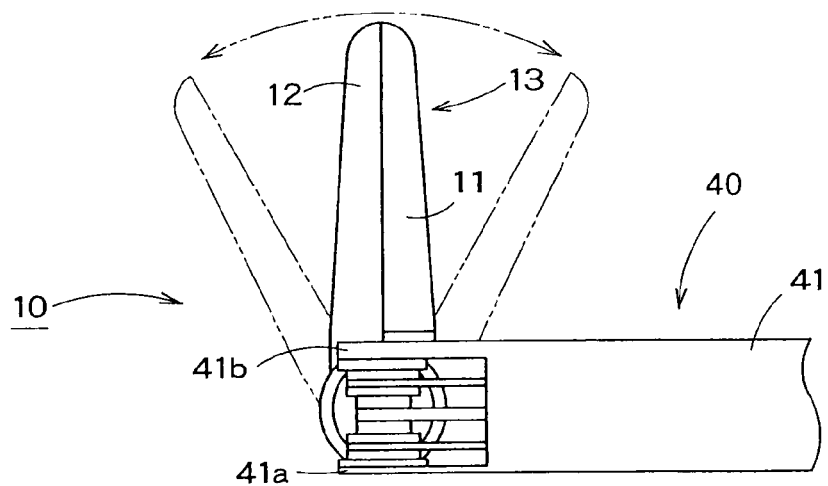
F I G. 12
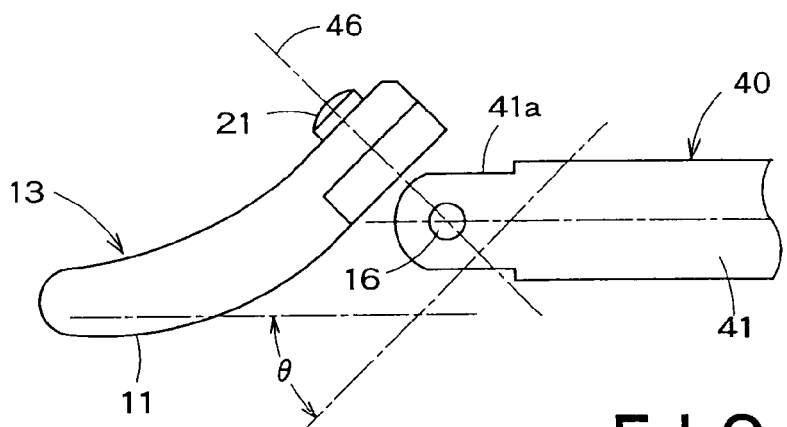
F I G. 13
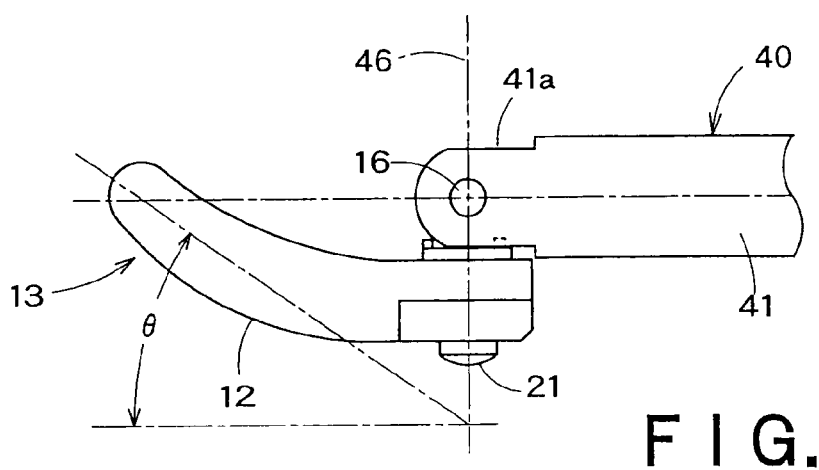
F I G. 14

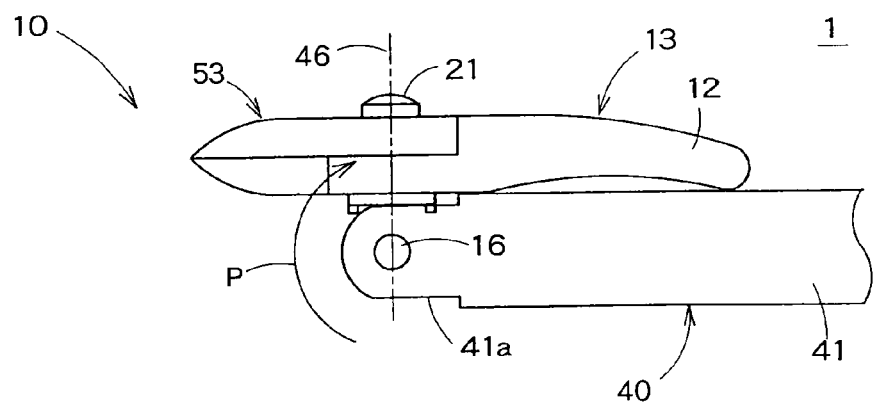
F I G. 18
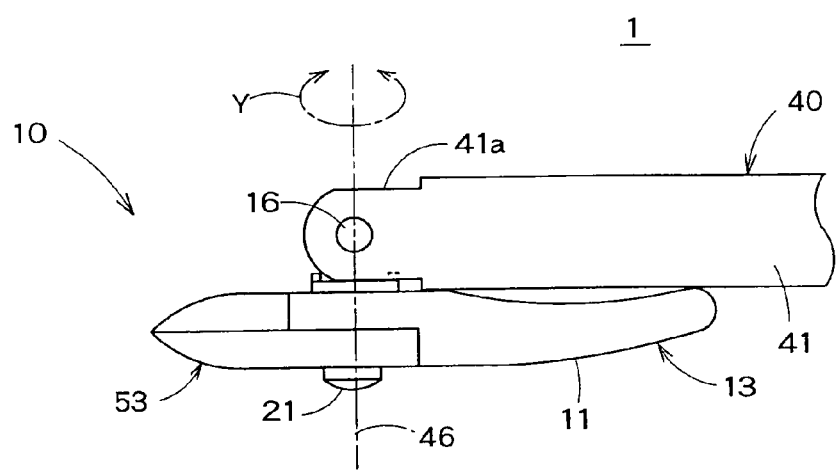
F I G. 19
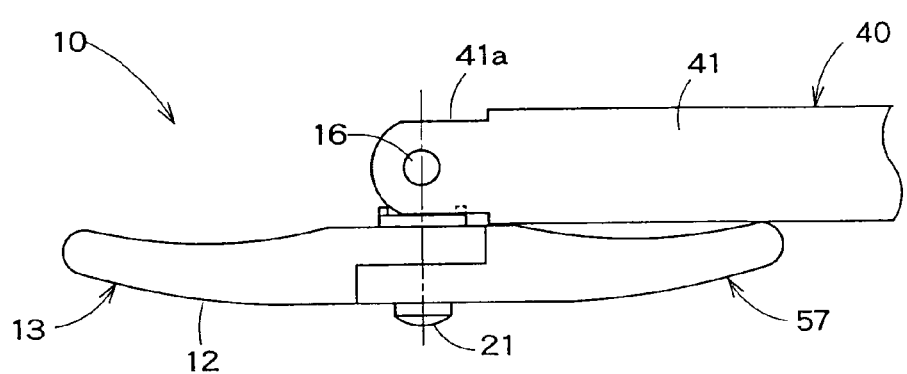
F I G. 20

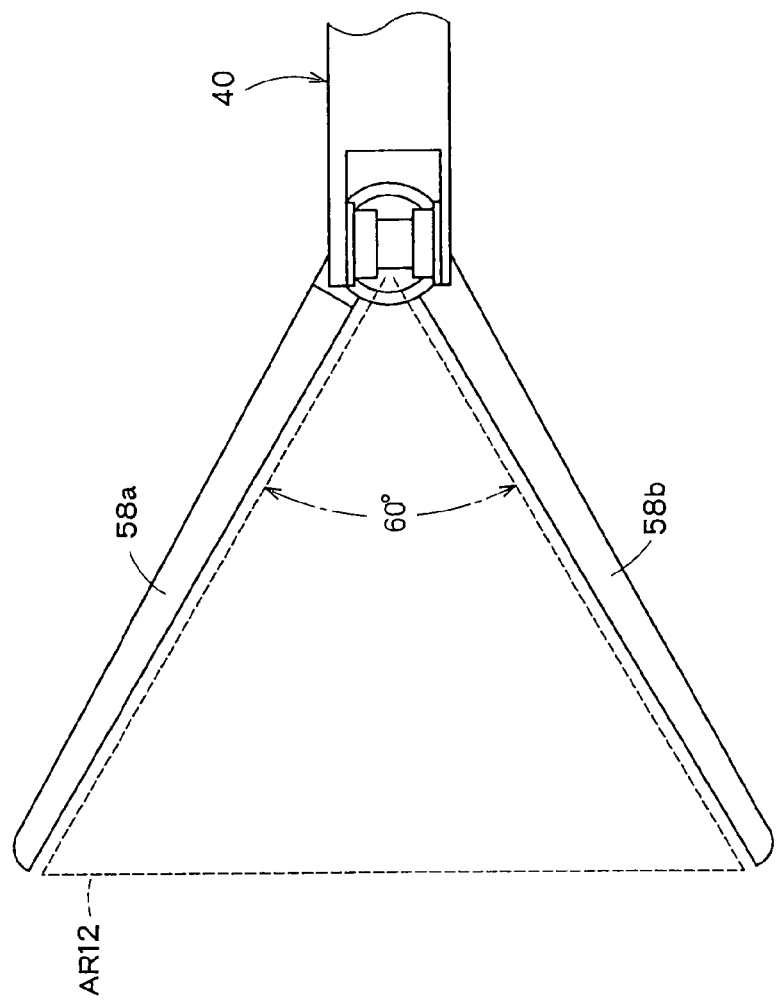
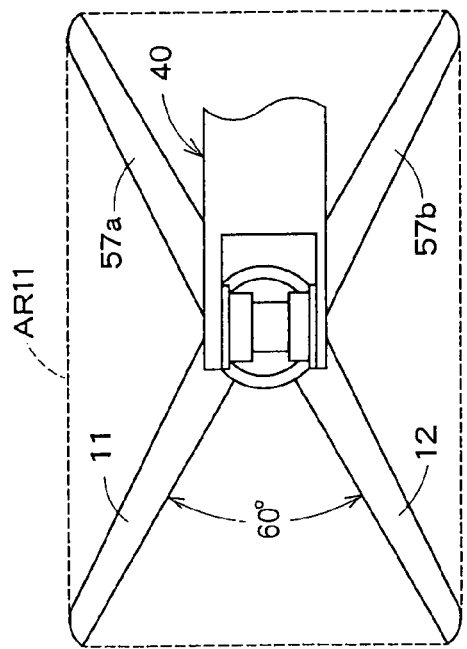
FIG. 23A
FIG. 23B

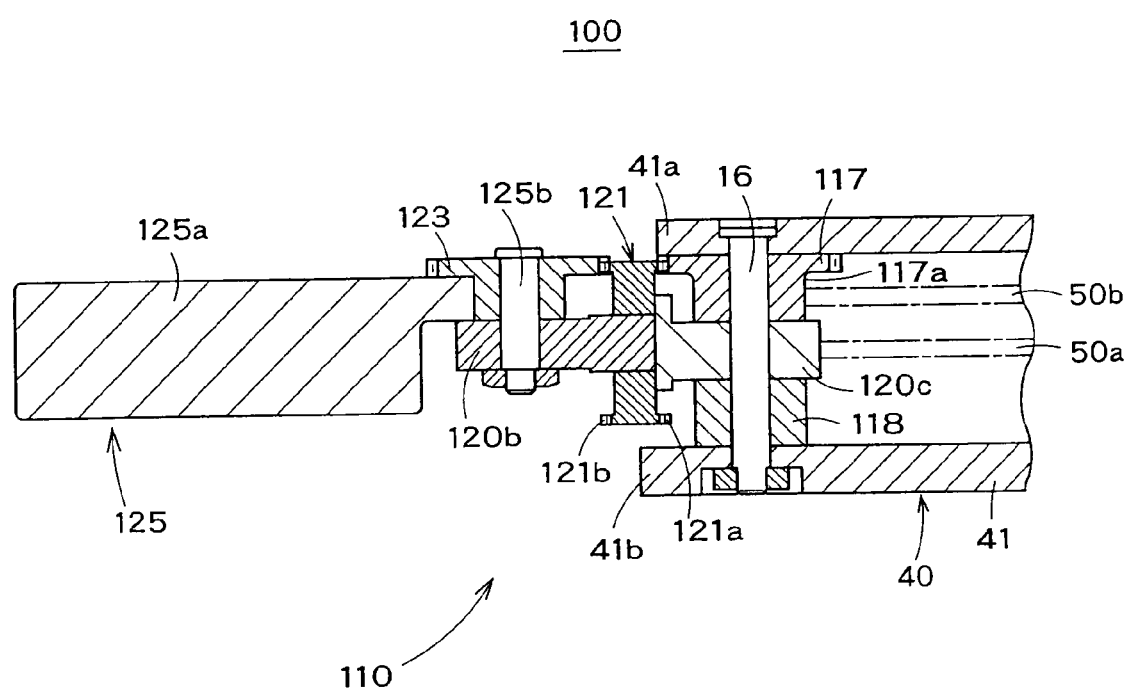
F I G. 27

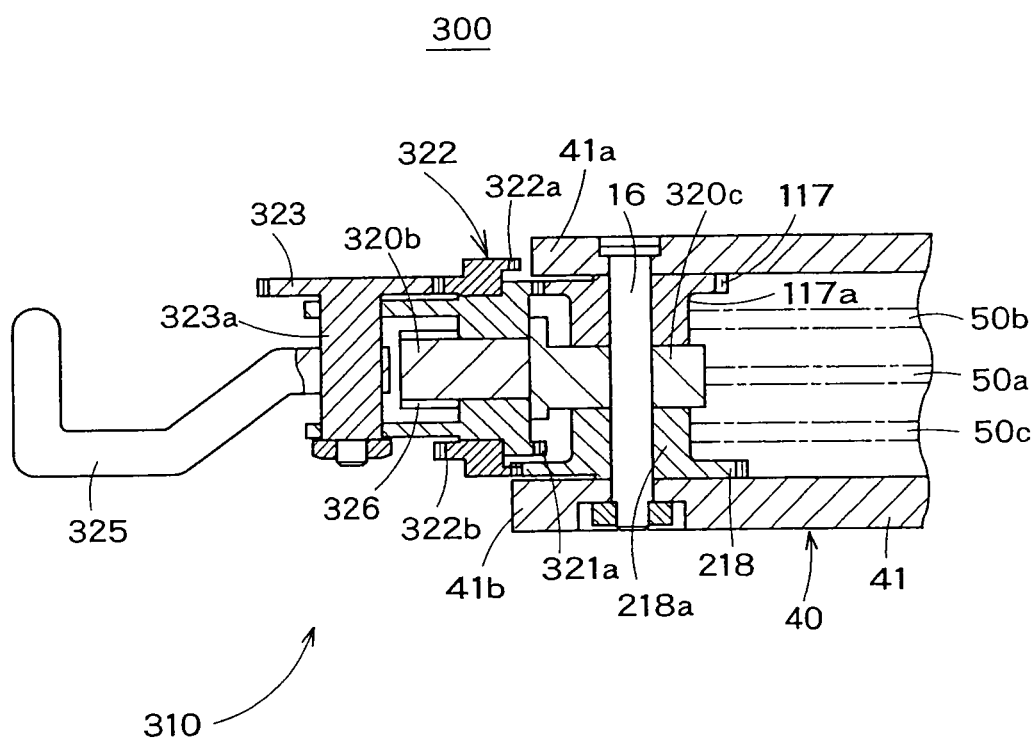
F I G. 33

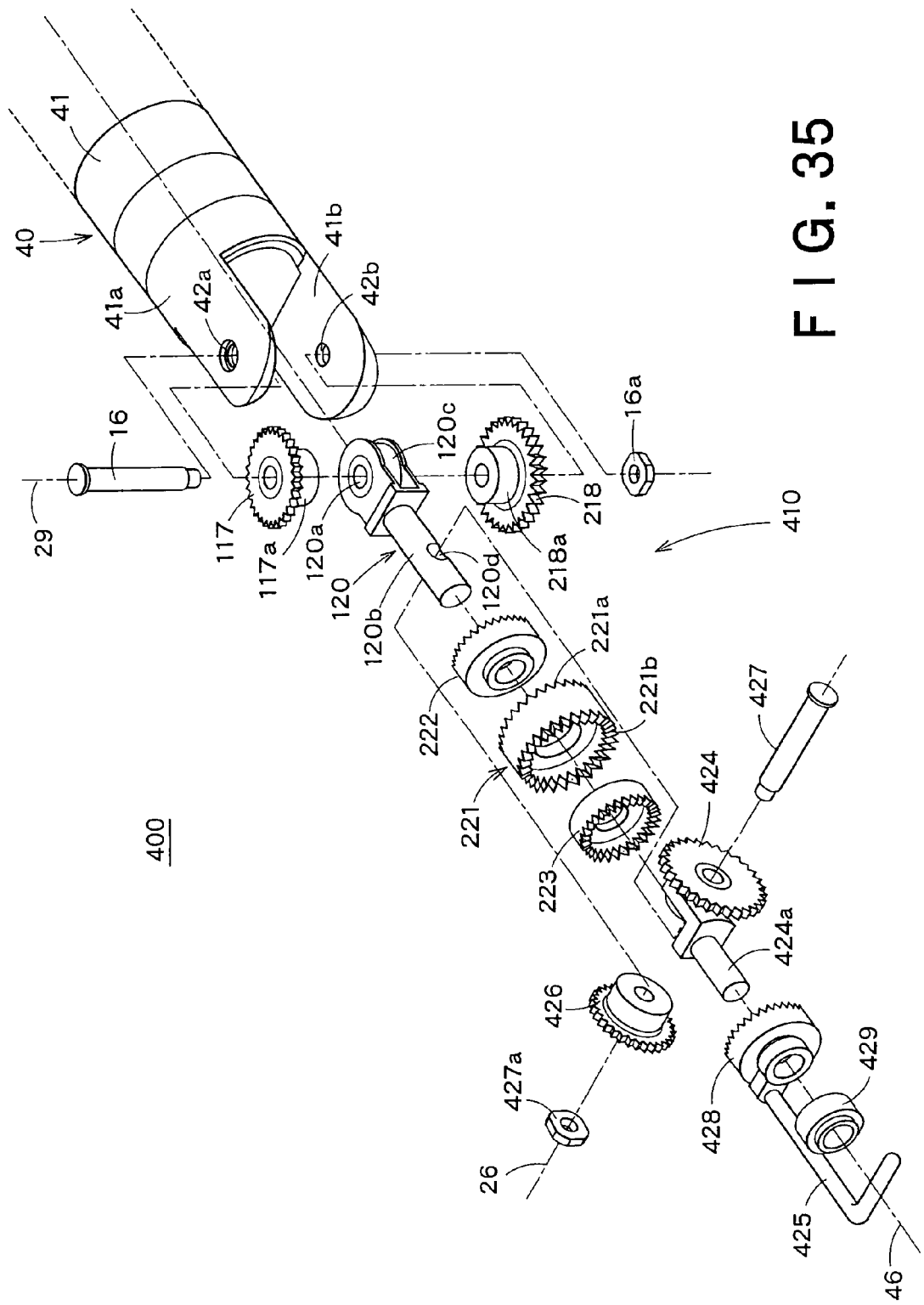
F I G. 35

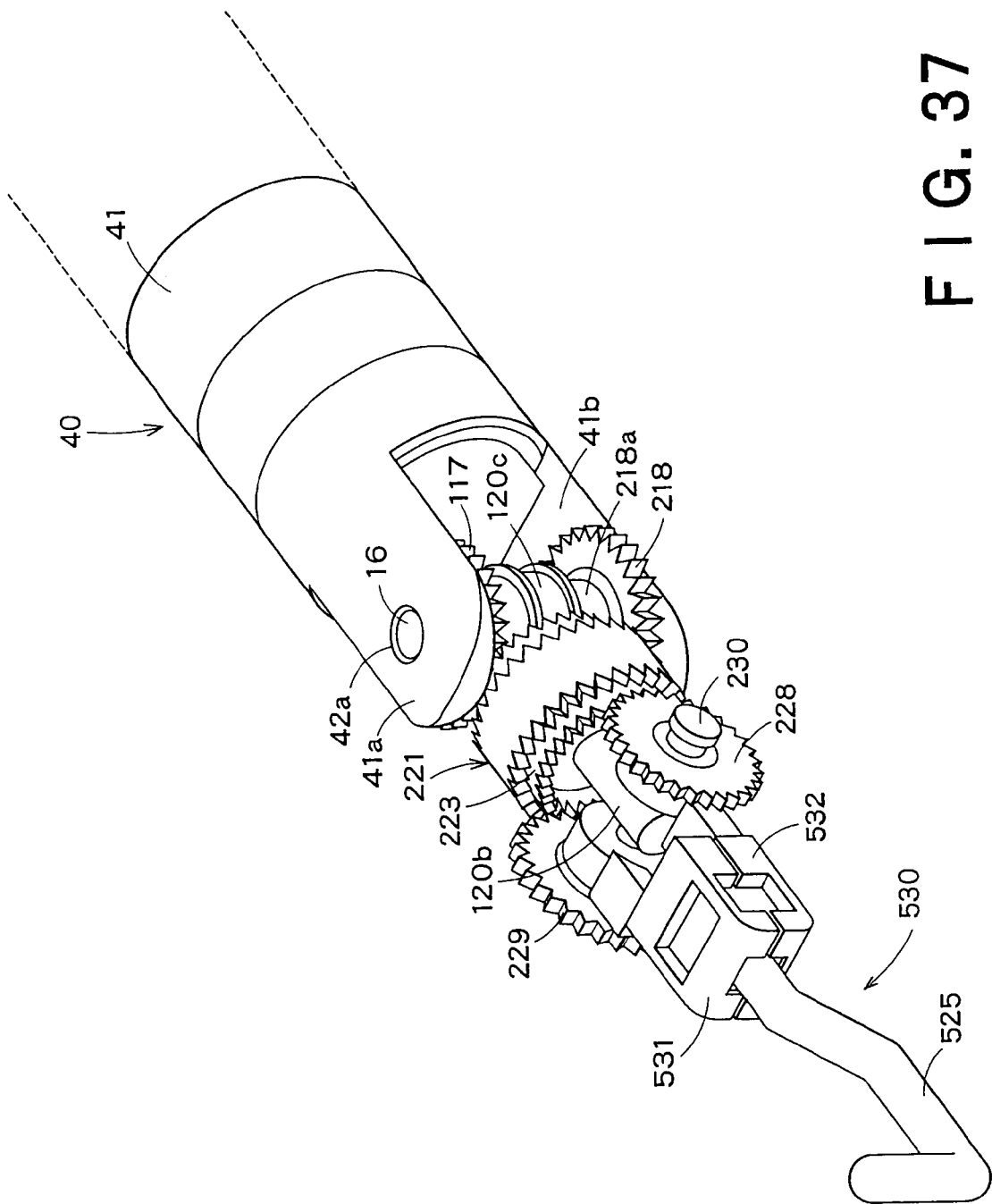
F I G. 37

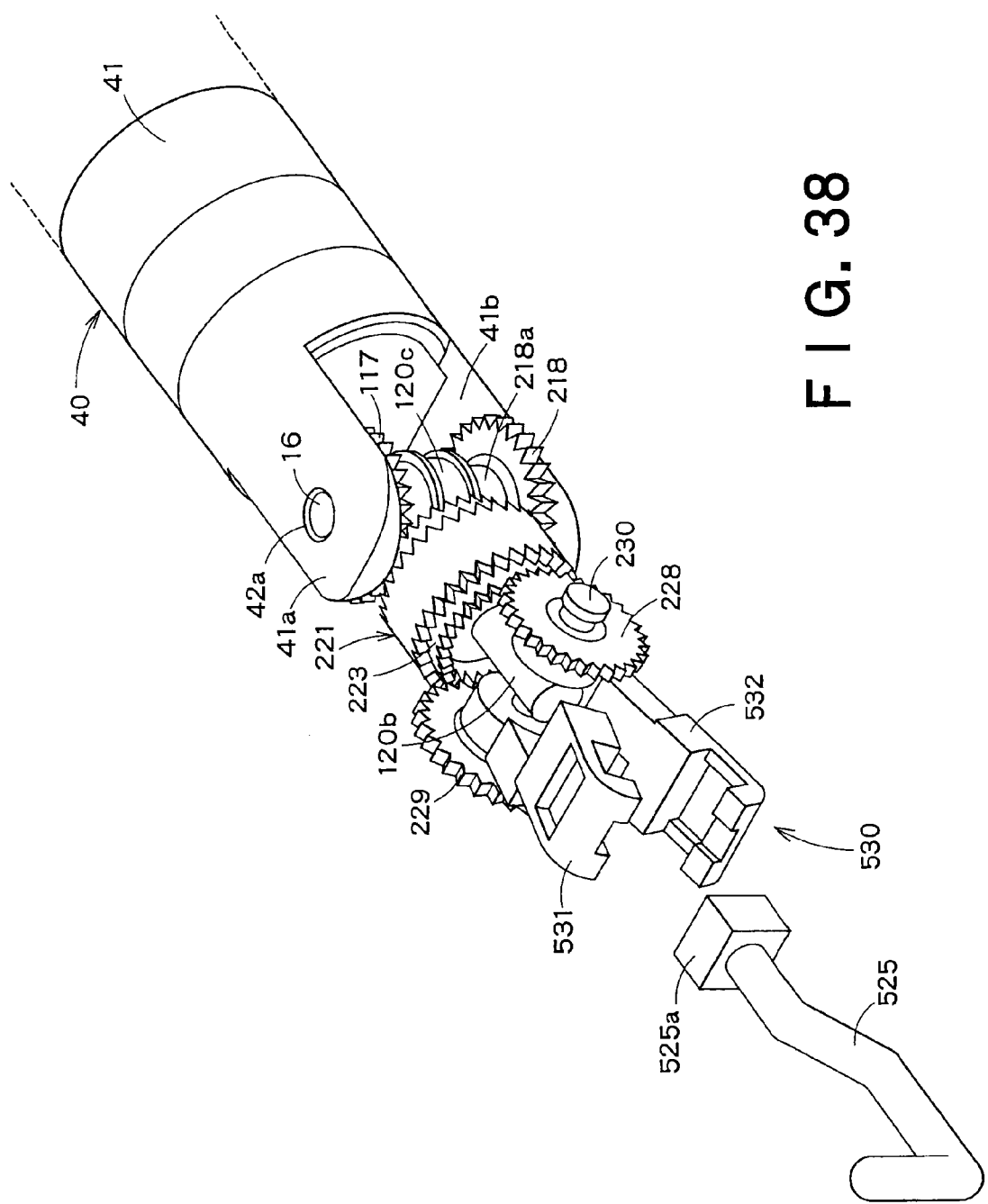
F I G. 38

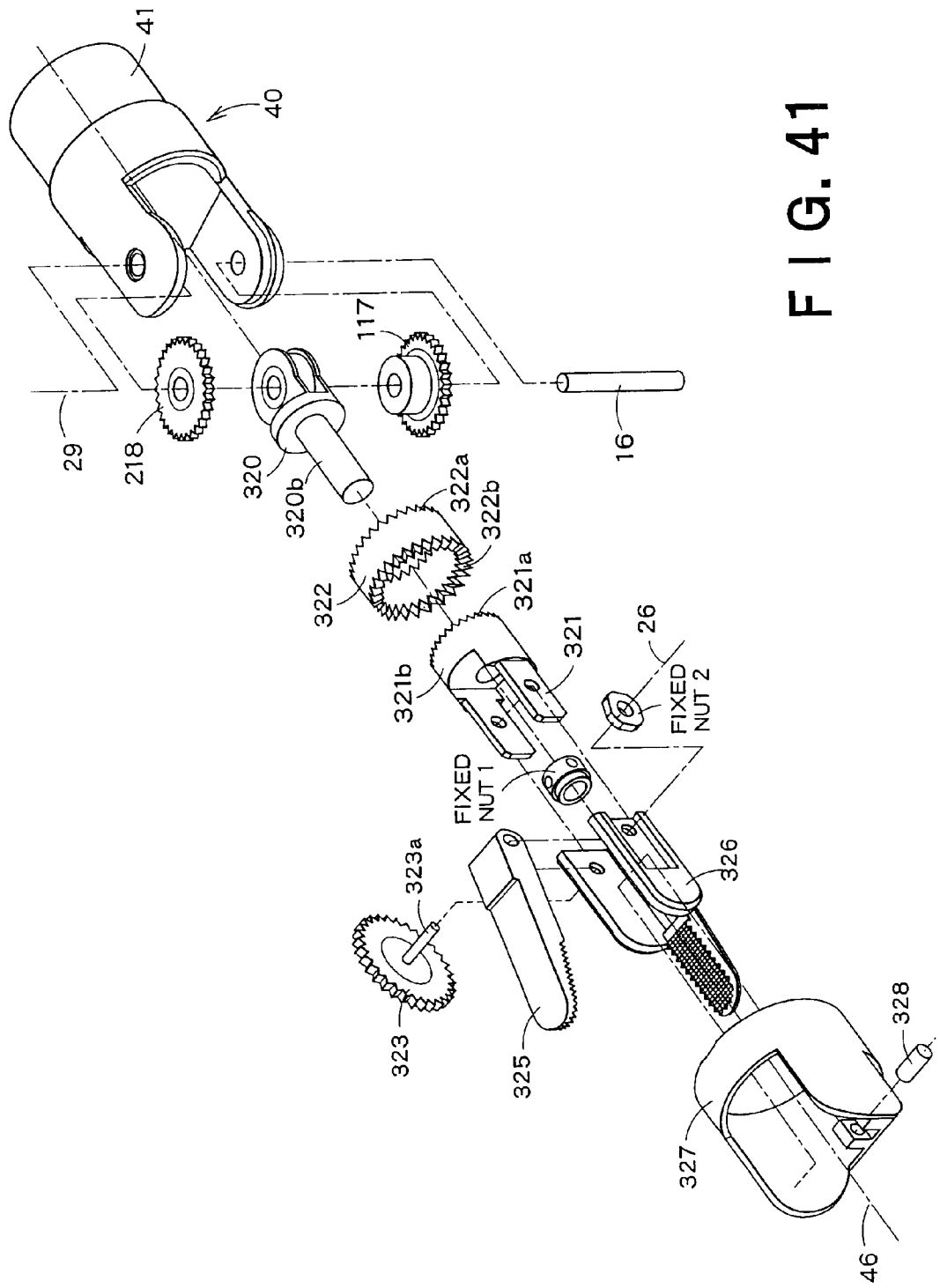
F I G. 41

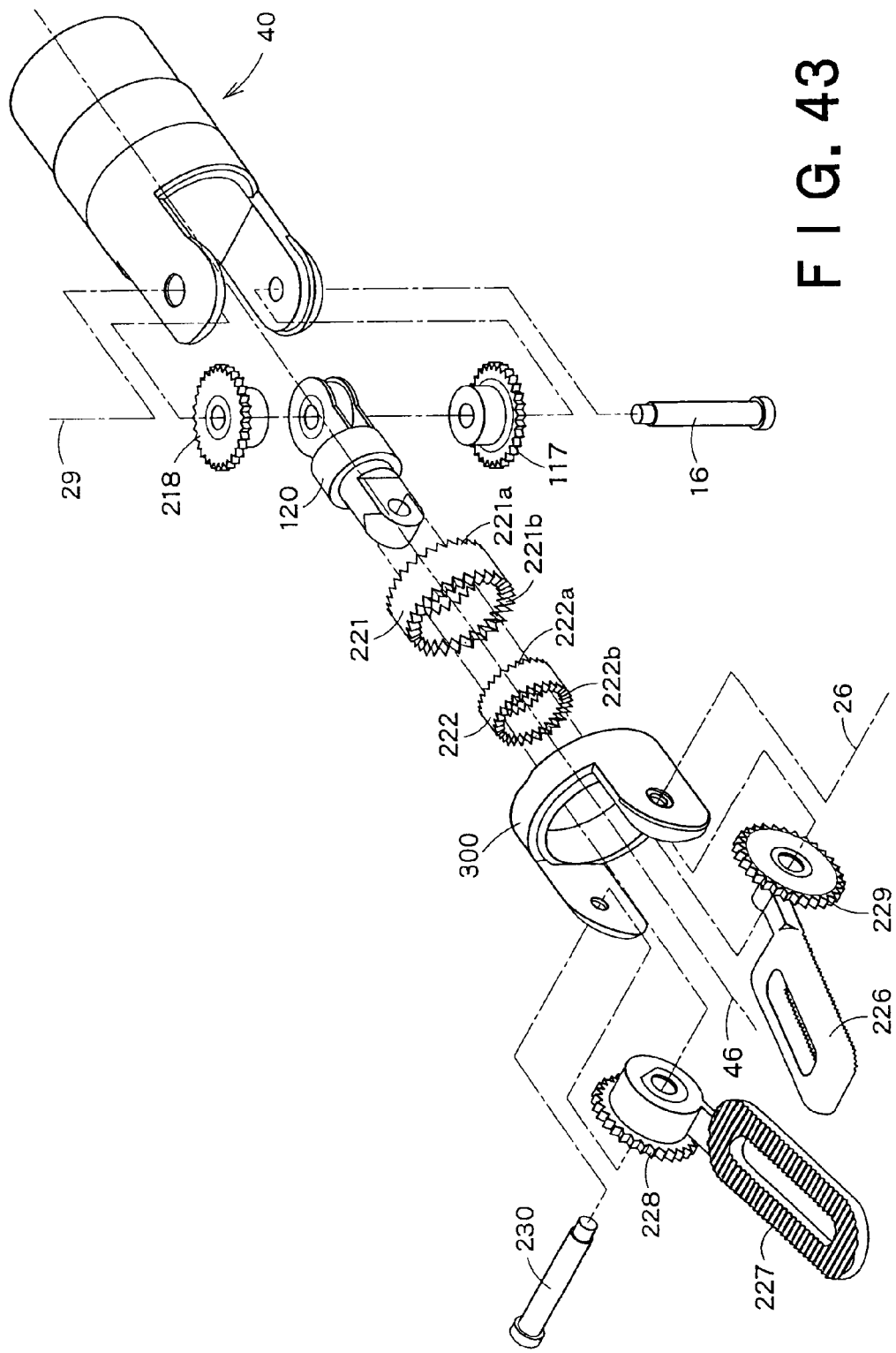
F I G. 43

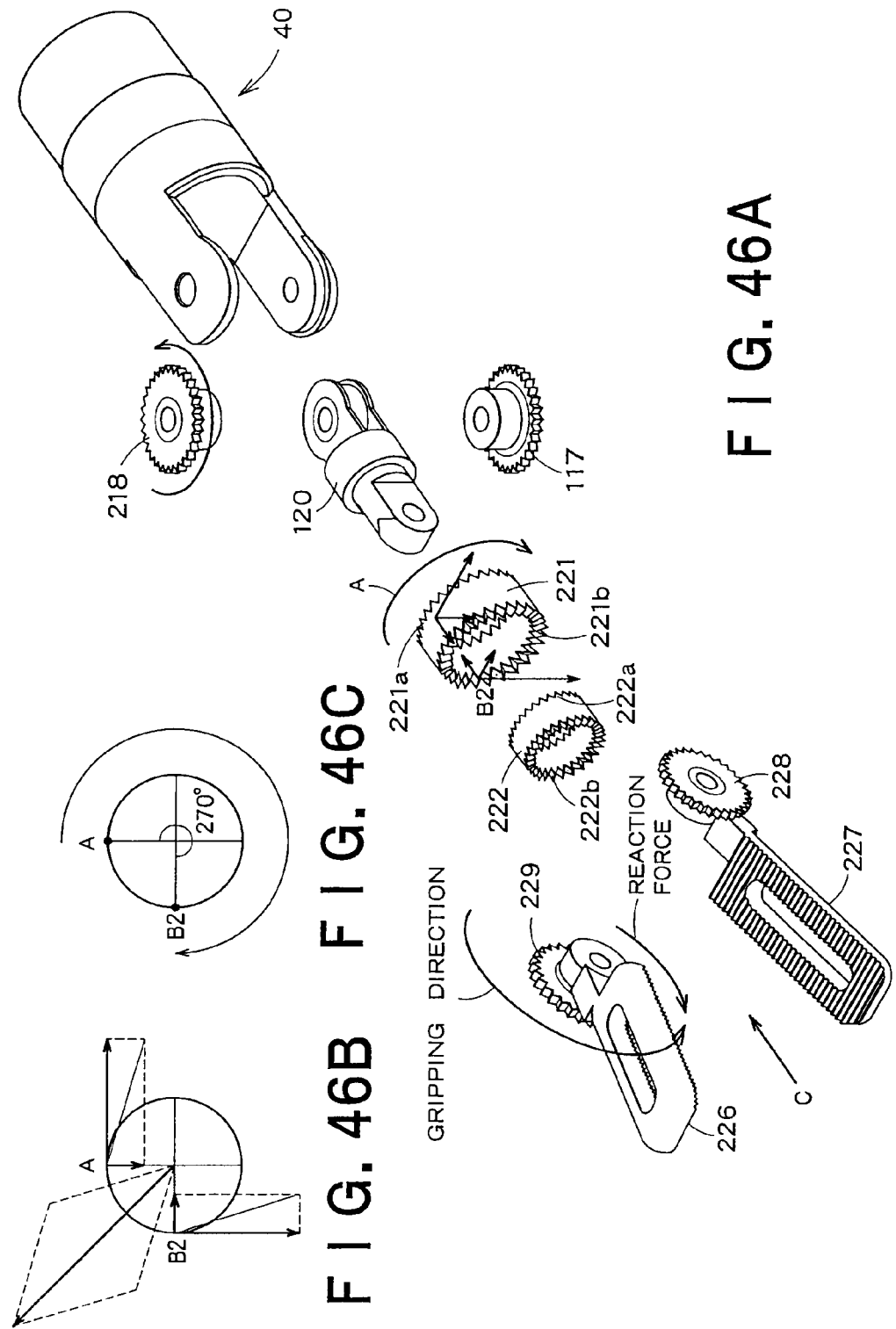

MANIPULATOR

CROSS REFERENCE TO RELATED APPLICATIONS

This application is a divisional application of application Ser. No. 11/390,458, filed Mar. 28, 2006, which is based upon and claims the benefit of priority from the prior Japanese Patent Application No. 2005-96115, filed on Mar. 29, 2005, the entire contents of each of which are incorporated herein by reference.

BACKGROUND OF THE INVENTION

1. Field of the Invention

The present invention relates to a manipulator which is used, for example, for use in laparoscopic surgeries.

2. Related Art

In laparoscopic surgeries such as gallbladder extirpation surgery, an operator makes a number of small holes in the patient's abdomen, attaches trocars to the holes, inserts an endoscope, a forceps, and the like into the abdomen via the trocars, and then treats the patient while viewing images from the endoscope via a monitor.

These surgeries involve no celiotomy and thus impose reduced burdens on patients. These surgeries also allow the patient to recover quickly after the operation, thus significantly reducing a period after the patient is hospitalized and before he or she leaves the hospital. The application of the laparoscopic surgery is expected to be extended.

As a manipulator for use in laparoscopic surgeries, the manipulator for applying robotics has been proposed (see Japanese Patent Laid-Open No. 2000-350735). The manipulator has a manipulating portion and an operating portion which are connected together via a cylindrical connecting portion. The operating portion operates at a predetermined degree of freedom in response to manipulations of the manipulating portion. The operating portion has, for example, a pair of plate members that sandwich an affected part. The pair of plate members is opened and closed in accordance with signals from the manipulating portion.

In terms of the degree of freedom of the operating portion, for example, a structure having the degree of freedom suitable for sutures and ligations has been proposed (see Japanese Patent Laid-Open No. 2002-102248). This manipulator can change position of the forceps along directions of a pitch axis, a roll axis, and a yaw axis.

A manipulator having a pitch axis joint and a yaw axis joint has been proposed (see Japanese Patent Laid-Open No. 2003-61969). This manipulator has a gripper that treats an affected part. The gripper can rotate around pitch axis joint and yaw axis joint.

The manipulator used to treat a narrow part such as laparoscopic surgeries is required to have a wide range of operation, good operability, a reduced number of parts, high strength, high credibility and high safety.

In terms of these characteristics, the conventional manipulators have wirings complicatedly disposed to improve the degree of freedom of the forceps. Therefore, there was a problem in which the structure is complicated.

SUMMARY OF THE INVENTION

The present invention has been made to solve the above technical problems. An object of the present invention is to provide a manipulator which has a treating portion with an increased degree of freedom and has a further simplified structure.

According to one embodiment of the present invention, a manipulator, comprising:
a treating portion;
a driving portion which are connected by a connecting portion;
a first pulley on which a first wire which passes through inside of the connecting portion and is driven by the driving portion is hung for rotation; and
a main shaft portion which rotatably supports the treating portion around a main shaft along a direction different from a first rotor axis that the first pulley rotates, one end portion of which is fixed to the first pulley.

According to one embodiment of the present invention, a manipulator, comprising:
a first rotor axis portion which crosses to a direction along a longitudinal direction of a connecting portion at a tip of which a treating portion is provided to treat a treatment target;
a main shaft portion which is rotatably supported in a direction around the first rotor axis portion and is provided in a direction crossing to the first rotor axis portion;
a first gear rotatably supported in the direction around the first rotor axis portion;
a second gear rotatably supported in the direction around the first rotor axis portion;
a third gear which engages with the first gear and is rotatably supported in a direction around the main shaft portion;
a fourth gear which engages with the second gear and is rotatably supported in a direction around the main shaft portion;
a first treating member which rotates with the third gear; and
a second treating member which rotates with the fourth gear.

According to one embodiment of the present invention, a manipulator, comprising:
a first rotor axis portion which crosses to a direction along a longitudinal direction of a connecting portion at a tip of which a treating portion is provided to treat a treatment target;
a main shaft portion which is rotatably supported in a direction around the first rotor axis portion and is provided in a direction crossing to the first rotor axis portion;
a treating member provided in the treating portion;
a first gear rotatably supported in the direction around the first rotor axis portion;
a second gear which engages with the first gear and is rotatably supported in a direction around the main shaft portion;
a third gear which coaxially rotates with the second gear;
a fourth gear which is provided to transmit rotation torque of the third gear to the treating member and engages with the third gear; and
a second rotor axis portion which is rotation center of the fourth gear and is arranged in a torsional relationship with the first rotor axis portion.

According to one embodiment of the present invention, a manipulator, comprising:
a first rotor axis portion which crosses to a direction along a longitudinal direction of a connecting portion at a tip of which a treating portion is provided to treat a treatment target;
a main shaft portion which is rotatably supported in a direction around the first rotor axis portion and is provided in a direction crossing to the first rotor axis portion;
a first treating member and a second treating member which are provided in the treating portion;

a first gear rotatably supported in the direction around the first rotor axis;

a second gear rotatably supported in the direction around the first rotor axis;

a third gear which engages with the first gear and is rotatably supported around the main shaft portion;

a fourth gear which engages with the second gear and is rotatably supported around the main shaft portion;

a fifth gear which coaxially rotates with the third gear;

a sixth gear which coaxially rotates with the fourth gear;

a seventh gear which is provided to transmit rotation torque of the fifth gear to the first treating member and engages with the fifth gear;

a eighth gear which provided to transmit rotation torque of the sixth gear to the second treating member and engages with the sixth gear; and a second rotor axis portion which is rotation center of the seventh gear and the eighth gear and is arranged in a torsional relationship with the first rotor axis portion.

According to one embodiment of the present invention, a manipulator, comprising:

a first rotor axis portion arranged orthogonal to a direction along a longitudinal direction of a connecting portion at a tip of which a treating portion is provided to treat a treatment target;

a main shaft portion which is rotatably supported in a direction around the first rotor axis portion and is provided in a direction crossing to the first rotor axis portion;

a first gear rotatably supported in a direction around the first rotor axis portion;

a second gear rotatably supported in a direction around the first rotor axis portion;

a third gear which engages with the first gear and is rotatably supported in a direction around the main shaft portion;

a fourth gear which engages with the second gear and is rotatably supported in the direction around the main shaft portion;

a second rotor axis portion which coaxially rotates with the third gear;

a fifth gear which coaxially rotates with the fourth gear;

a third rotor axis portion which rotates in the direction around the main shaft portion in conformity with rotation of the second rotor axis portion and is arranged from a torsional position to a parallel position with the first rotor axis portion;

a sixth gear which is rotatably supported in a direction around the third rotor axis portion and engages with the fifth gear; and a first treating member which rotates in the direction around the third rotor axis portion with the sixth gear and rotates in the direction around the main shaft portion with the third gear.

According to one embodiment of the present invention, a manipulator, comprising:

a first rotor axis portion arranged orthogonal to a direction along a longitudinal direction of a connecting portion at a tip of which a treating portion is provided to treat a treatment target;

a main shaft portion which is rotatably supported in a direction around the first rotor axis portion and is provided in a direction crossing to the first rotor axis portion;

a first gear rotatably supported in a direction around the first rotor axis portion;

a second gear rotatably supported in a direction around the first rotor axis portion;

a third gear which engages with the first gear and is rotatably supported in a direction around the main shaft portion;

a fourth gear which engages with the second gear and is rotatably supported in a direction around the main shaft portion;

a fifth gear which coaxially rotates with the third gear;

a sixth gear which coaxially rotates with the fourth gear;

a seventh gear which engages with the fifth gear;

a eighth gear which engages with the sixth gear;

a second rotor axis portion which is rotation center of the seventh gear and the eighth gear and is arranged in a torsional relationship with the first rotor axis portion;

a third rotor axis portion which rotates in a direction around the second rotor axis portion with the eighth gear;

a ninth gear which engages with the seventh gear and rotates in a direction around the third rotor axis portion; and a treating member which coaxially rotates with the ninth gear.

BRIEF DESCRIPTION OF THE DRAWINGS

FIG. 2 is a perspective view showing an operating portion of the manipulator of FIG. 1.

FIG. 3 is an exploded perspective view showing the operating portion of the manipulator of FIG. 1.

FIGS. 4A-4B are a cross-sectional view and an edge view showing the operating portion of the manipulator of FIG. 1.

FIG. 6 is an omitted line view showing a wire disposing state and arrangement of the driving motor.

FIG. 7 is an omitted line view showing a wire driving state of the manipulator of FIG. 1.

FIG. 10 is an edge view for operational explanation of the manipulator of FIG. 1.

FIG. 11 is an edge view for operational explanation of the manipulator of FIG. 1.

FIG. 12 is an edge view for operational explanation of the manipulator of FIG. 1.

FIG. 13 is an edge view showing curbed shape of the gripper of the manipulator of FIG. 1.

FIG. 14 is an edge view showing curbed shape of the gripper of the manipulator of FIG. 1.

FIG. 18 is an edge view for operational explanation of the gripper of the manipulator of FIG. 15.

FIG. 19 is an edge view for operational explanation of the gripper of the manipulator of FIG. 15.

FIG. 20 is an edge view showing a modified example of the manipulator of FIG. 15.

FIGS. 23A-23B are omitted line views showing the compressed area of the gripper of FIG. 20.

FIG. 27 is a cross-sectional view showing the operating portion of FIG. 25.

FIG. 33 is a cross sectional view showing the operating portion of FIG. 31.

FIG. 35 is an exploded perspective view showing the operating portion according to the sixth embodiment.

FIG. 37 is a perspective view showing the operating portion of the manipulator according to the other embodiment.

FIG. 38 is a perspective view showing the operating portion of the manipulator according to the other embodiment.

FIG. 41 is an exploded perspective view showing the operating portion of FIG. 40.

FIG. 43 is an exploded perspective view showing the operating portion of FIG. 42.

FIG. 46A is an exploded perspective view in the case where transmission path of torque is long, FIG. 46B is a view seen from the thrust direction (C direction) of the second gear member, and FIG. 46C is a view schematically showing force transmitting paths.

DETAILED DESCRIPTION OF THE INVENTION

Figure 1:
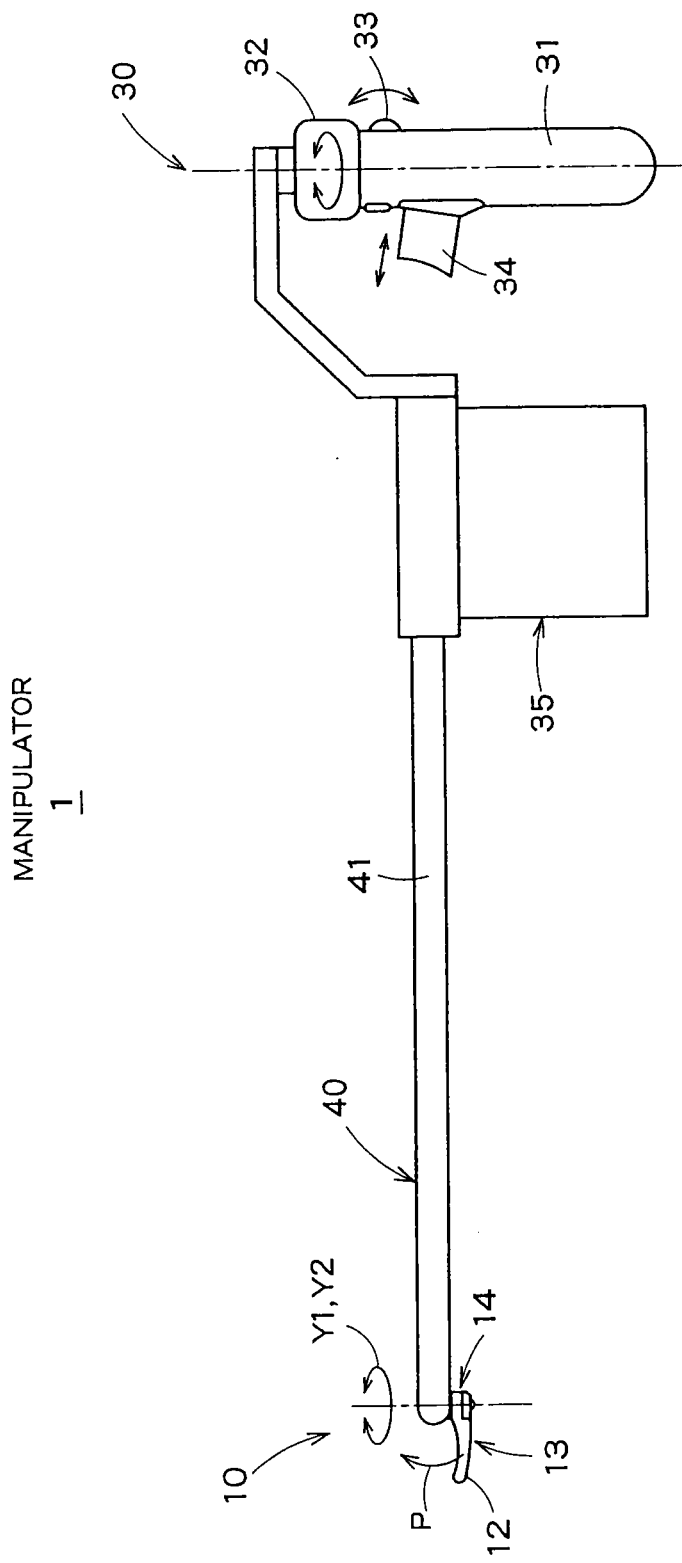
FIG. 1 is an edge view of a manipulator according to a first embodiment.

Embodiments of the present invention will be described below in detail with reference to the drawings. In the description of the drawings, the same components are denoted by the same reference numerals, and duplicate descriptions will be omitted. As a matter of convenience in the descriptions, a term of "orthogonal" denotes "substantially orthogonal". The orthogonal direction includes a relationship or a direction which crosses with angles having angle-difference which do not prevent use of the manipulator according to the present invention. The "cross" includes relationship or direction which crosses with an interval which does not cause a trouble, i.e. a torsional relationship or a torsional direction, when the manipulator according to the present embodiment is used.

First Embodiment

As shown in FIG. 1, a manipulator 1 according to a first embodiment of the present invention is used for, for example, laparoscopic surgeries, and includes an operating portion 10 that treats an affected part, a manipulating portion 30 that receives input manipulations controlling the operation of the operating portion 10, and a connecting portion 40 that connects the operating portion 10 and the manipulating portion 30 together.

As shown in FIGS. 2 and 3, the manipulator 1 includes a first rotor shaft 16 (rotor axis 29) which crosses to a direction along a longitudinal direction of the connecting portion 40 at a tip of which a treating portion (operating portion 10) is provided to treat a treatment target, a main shaft 20 supported rotatably in a direction around the first rotor shaft 16, which has a main shaft portion 20b arranged orthogonal to the first rotor shaft 16, a first gear 17 supported rotatably in the direction around the first rotor shaft 16, a second gear 18 supported rotatably in the direction around the first rotor shaft 16, a third gear 22 which orthogonally engages with the first gear 17 and is supported rotatably in a direction around the main shaft portion 20b at a position offset from the first rotor shaft 16, and a fourth gear 23 which orthogonally engages with the second gear 18 and is supported rotatably in the direction around the main shaft portion 20b at a position offset from the first rotor shaft 16. The manipulator 1 also includes a gripping forceps 13 having a first treating member 11 (gripper) which rotates with the third gear 22 and a second treating member 12 (gripper) which rotates with the fourth gear 23.

In the connecting portion 40, a pair of supporting portions 41a and 41b is formed at a tip of a cylindrical main body member 41 so as to be opposite each other by sandwiching a center axis of the connecting portion 40. Bearing holes 42a and 42b are formed in the supporting portions 41a and 41b, respectively.

A rotor shaft 16 is inserted through the bearing holes 42a and 42b to constitute a rotor axis 29 arranged orthogonal to the center axis of the connecting portion 40. The rotor shaft 16 is prevented by a nut 16a from slipping off from the bearing holes 42a and 42b. Instead of the nut 16a, a fixing washer may be used to fix the rotor shaft 16 to the bearing holes 42a and 42b. Alternatively, caulking may be used to fix the rotor shaft 16 directly to the bearing holes 42a and 42b. The gears 17 and 18 and the main shaft 20 are rotatably supported by the rotor shaft 16. A pulley 17a is provided integrally with the gear 17 and concentrically with rotation center of the gear 17. The gear 17 is rotated by driving a wire hung around the pulley 17a. A pulley 18a is provided integrally with the gear 18 and concentrically with rotation center of the gear 18. The gear 18 is rotated by driving a wire hung around the pulley 18a.

The main shaft 20 includes a bearing portion 20a rotatably supported by the rotor shaft 16 and the cylindrical main shaft portion 20b fixed to the bearing portion 20a so that its center axis is oriented in a radial direction. A pulley 20c is provided concentrically with the bearing portion 20a. The pulley 20c and the main shaft portion 20b are fixed to each other. Driving a wire hung around the pulley 20c enables the main shaft portion 20b to be rotated around the rotor shaft 16 in a pitch direction shown by arrow "P".

Wires are passed through the cylindrical main body member 41 of the connecting portion 40; the wires are hung between the pulleys 17a, 18a, and 20c and the driving portion 35. When the manipulating portion 30 manipulates the wires, the pulleys 17a, 18a and 20c are individually rotated around the center axis of the rotor shaft 16. In the present embodiment, the center axis of the rotor shaft 16 is called a pitch axis (rotor axis 29). The direction of rotating around the pitch axis is called a pitch direction.

A gear member 22 is rotatably supported around the main shaft portion 20b of the main shaft member 20. The gear member 22 includes a cylindrical bearing portion 22a rotatably supported around the main shaft portion 20b and a gear portion 22b which is integrated with the bearing portion 22a, arranged around the center axis of the bearing portion 22a, and oriented in the direction of an extension of the center axis.

The gear portion 22b engages with the gear 17 to convert rotation operation around the rotor shaft 16 into rotation operation in which the main shaft portion 20b (main shaft 46) orthogonal to the rotor shaft 16 is rotation center. A combination of the gears used for the case where the rotation axes are orthogonal to each other such as the rotor shaft 16 and the gear member 22 may be a combination of a spur gear (gear 17) and a face gear (gear portion 22b) shown in the present embodiment, or may be a combination of bevel gears.

A gear member 23 is rotatably supported around an outer peripheral surface portion of the bearing portion 22a of the gear member 22. The gear member 23 includes a cylindrical bearing portion 23a rotatably supported around the outer peripheral surface portion of the bearing portion 22a of the gear member 22 and a gear portion 23b which is integrated with the bearing portion 23a, arranged around the center axis of the bearing portion 23a and oriented in the direction of an extension of the center axis.

The gear portion 23b engages with the gear 18 to convert rotation operation around the rotor shaft 16 (rotor axis 29) into rotation operation of the bearing portion 23a in which the main shaft portion 20b (main shaft 46 and bearing portion 22a) orthogonal to the rotor shaft 16 is rotation center. A combination of the gears used for the case where the rotation axes are orthogonal to each other such as the rotor shaft 16 and the gear member 23 may be a spur gear (gear 18) and a face gear (gear portion 23b), as shown in the present embodiment, or may be a combination of bevel gears.

In such a way, the rotation in which the rotor shaft 16 is rotation center is converted into the direction of the rotation in which the main shaft portion 20b of the main shaft 20 orthogonal to the rotor shaft 16 is rotation center. Orthogonal relationship between the rotor shaft 16 and the main shaft portion 20 is established regardless of the position of the main shaft portion 20b in the pitch direction. Consequently, the gear members 22 and 23 can be rotated via the gears 17 and 18, respectively, regardless of the position of the main shaft portion 20b in the pitch direction.

The length L1 of bearing portion 22a of the gear member 22 is larger than the length L2 of bearing portion 23a of the gear member 23. The insertion of the bearing portion 22a of the gear member 22 into the gear member 23 results in the projection and exposure of a tip of the bearing portion 22a from the gear member 23. A planar D cut portion 22c is formed in the tip of the bearing portion 22a. An outer peripheral surface part including the D cut portion 22c is fitted into a fitting hole 11a in the gripper 11. The fitting hole 11a is formed in conformity to the shape of the outer peripheral surface part of the bearing portion 22a including the D cut portion 22c. This enables rotation of the gear member 22 to be reliably transmitted to the gripper 11. In the gripper 11, a planar treating portion 11c is integrated with a support portion 11b in which the fitting hole 11a is formed. A turn of the gear member 22 allows the treating portion 11c to be rotated in a yaw direction shown by arrow Y1.

A planar D cut portion 23c is formed in an outer peripheral surface part of bearing portion 23a of the gear member 23. The outer peripheral surface part including the D cut portion 23c is fitted into a fitting hole 12a in the gripper 12. The fitting hole 12a is formed in conformity to the shape of the outer peripheral surface part of the bearing portion 23a including the D cut portion 23c. This enables rotation of the gear member 23 to be reliably transmitted to the gripper 12. In the gripper 12, a planar treating portion 12c is integrated with a support portion 12b in which the fitting hole 12a is formed. Rotation of the gear member 23 allows the treating portion 12c to be rotated in a yaw direction shown by arrow Y2.

In the yaw directions Y1 and Y2, the grippers 11 and 12 rotate around the main shaft portion 20b of the main shaft member 20. The yaw directions Y1 and Y2 vary depending on rotation of the main shaft 20 around the pitch axis (rotor shaft 16).

The treating portions 11c and 12c of the grippers 11 and 12 are rotated in the yaw directions Y1 and Y2 in accordance with the rotations of the gear members 22 and 23. When the gear members 22 and 23 are rotated in directions different from each other, the treating portions 11c and 12c are rotated in an open direction or a close direction. When the gear members 22 and 23 are rotated in the same direction, the treating portions 11c and 12c are rotated in the same direction.

The gears 17 and 18, used to rotate the gear members 22 and 23, are arranged to engage with the gear members 22 and 23 at a position opposite to each other across the rotation center axis of the gear members 22 and 23. Thus, rotation of the gears 17 and 18 in the same direction enables the treating portions 11c and 12c of the grippers 11 and 12 to be rotated so as to be closed or opened. In contrast, rotation of the gears 17 and 18 in different directions enables the treating portions 11c and 12c of the grippers 11 and 12 to be rotated in the same direction (yaw operation).

Thus, the treating portions 11c and 12c of the grippers 11 and 12 can be opened or closed or rotated in the yaw direction by manipulating the wire hung around the pulley 17a of the gear 17 and the wire hung around the pulley 18a of the gear 18.

At a state in which the gear members 22 and 23 and grippers 11 and 12 are supported around the main shaft portion 20b of the main shaft member 20, a fixing member 21 is fixed to the tip of the main shaft portion 20b. This prevents the gear members 22 and 23 and grippers 11 and 12 from slipping off from the main shaft portion 20b and maintains the appropriate engagement of the gears.

As shown in FIG. 4A, wires 50a, 50b, and 50c are hung around the pulleys 20c, 17a, and 18a through an internal space of the cylindrical main body member 41 of the connecting portion 40. Manipulation of the wires 50a, 50b, and 50c enables the pulleys 20c, 17a, and 18a to be individually turned. That is, as shown in FIG. 4B, the main shaft 20 can be rotated in the pitch direction "P" by manipulating the wire 50a (FIG. 4A) to rotate the pulley 20c. The gripper 11 can be rotated in the yaw direction "Y1" by manipulating the wire 50b (FIG. 4A) to rotate the pulley 17a. The gripper 12 can be rotated in the yaw direction "Y2" by manipulating the wire 50c (FIG. 4A) to rotate the pulley 18a. In this case, since the driving mechanism causes a mechanism interference, the wires 50a, 50b, and 50c need to be manipulated taking interference components into account.

Figure 5:
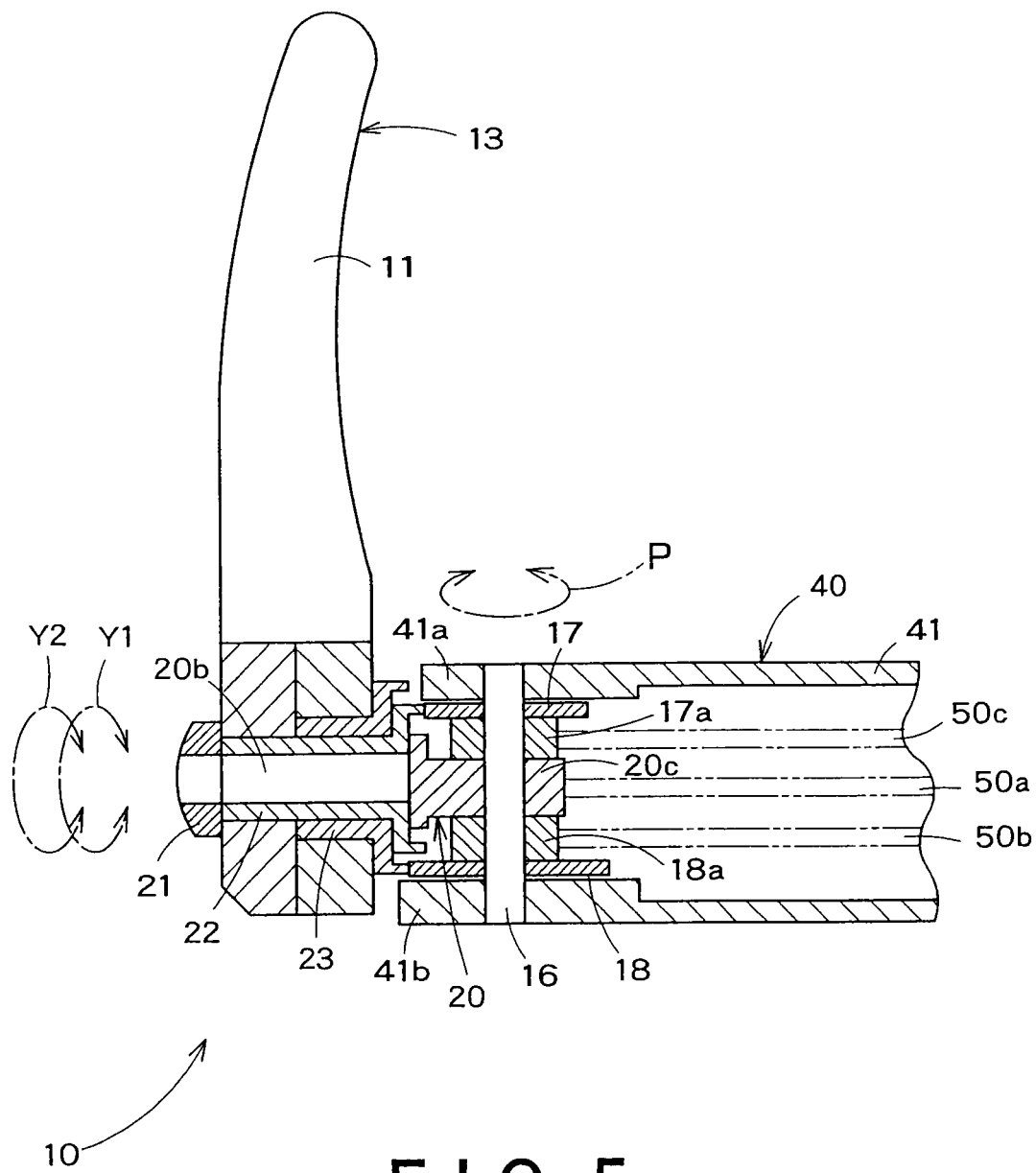
FIG. 5 is a cross-sectional view showing the operating portion of the manipulator of FIG. 1.

FIG. 5 shows that the main shaft portion 20b of the main shaft 20 is rotated in a direction around the pitch axis (rotor shaft 16) so that the main shaft portion 20b aligns with the extended direction of the center axis of the connecting portion 40. FIG. 5 also shows that the grippers 11 and 12 are rotated around the yaw axis (main shaft portion 20b). Thus, with the operating portion 10, the grippers 11 and 12 supported around the main shaft portion 20b can be rotated in the pitch direction by rotating the main shaft portion 20b of the main shaft 20 around the rotor shaft 16. The grippers 11 and 12 can be rotated in the yaw direction by rotating the grippers 11 and 12 supported around the main shaft portion 20b, in a direction around the main shaft portion 20b.

In FIG. 1, the connecting portion 40, having the operating portion 10 at one end, has the manipulating portion 30 at the other end. The manipulating portion 30 includes a manipulating lever 31 directly held by the operator, a yaw direction control manipulator 32 that controls the positions of the grippers 11 and 12, a pitch direction control manipulator 33, and a gripper opening and closing control manipulator 34.

The yaw direction control manipulator 32 includes a rotation manipulator and a rotational-position information output portion that outputs information indicative of the rotational position of the rotation manipulator. An arithmetic processing portion provided in an internal of the manipulating portion 30 or an external controller (not shown) calculates a manipulated amount based on rotation position information output by the yaw direction control manipulator 32, and generates control target values of the motors for controlling the positions of the grippers 11 and 12 in the yaw direction. The arithmetic processing portion also reads out information from an angle sensor that measures the operation angles of the motors controlling the positions in the yaw direction to compare the read-out information with a control target value, and calculates a motor driving instruction for eliminating the deviation. The arithmetic processing portion then outputs the calculated motor driving instruction to a driving portion 35.

The pitch direction control manipulator 33 includes a rotation manipulator and a rotational-position information output portion that outputs information indicative of the rotation position of the rotation manipulator. An arithmetic processing portion provided inside the manipulating portion 30 calculates a manipulated amount for the pitch direction control manipulator 33 on the basis of rotational-position information output by the pitch direction control manipulator 33, and generates control target values of the motors for controlling the positions of the grippers 11 and 12 based on the manipulated amount. The arithmetic processing portion also reads out information from an angle sensor that measures the operation angle of the motor for controlling the positions in the pitch direction. The arithmetic processing portion then compares the information with the control target value to calculate a motor driving instruction for eliminating the deviation. The arithmetic processing portion then outputs the calculated motor driving instruction to the driving portion 35. The arithmetic processing portion may be provided in the controller installed outside the manipulating portion 30.

The gripper opening and closing control manipulator 34 includes a trigger switch (volume) and a manipulation result output portion that outputs the manipulation result of the trigger switch. An arithmetic processing portion generates control target values of motors for controlling the opening and closing of the grippers 11 and 12 based on manipulation result information output by the gripper opening and closing control manipulator 34. The arithmetic processing portion also reads out information from the angle sensor that measures the operation angles of the motors for controlling the opening and closing of the grippers. The arithmetic processing portion then compares the information with the control target values to calculate a motor driving instruction for eliminating the deviation. The arithmetic processing portion then outputs the calculated motor driving instruction to the driving portion 35.

The driving portion 35 is provided between the connecting portion 40 and the manipulating portion 30 to drive the motor on the basis of the motor driving instruction by the manipulating portion 30. The driving portion 35 has two motors that individually control the grippers 11 and 12 in the yaw direction and one motor that controls the position of the main shaft 20 constituting a support for the grippers 11 and 12 in the pitch direction. The opening and closing of the grippers 11 and 12 is performed by cooperatively driving two motors for controlling the positions of the grippers 11 and 12 in the yaw direction.

In FIG. 6 where components corresponding to FIG. 2 are denoted by the same reference numerals, a motor 36a in the driving portion 35 has a driving pulley 37a around its rotating shaft. The wire 50a is hung between the driving pulley 37a and the pulley 20c of the main shaft 20 (FIG. 2) in the operating portion 10. This allows the pulley 20c to be driven by the driving pulley 37a. Rotation of the motor 36a enables the pulley 20c to be rotated via the driving pulley 37a and wire 50a. Since the main shaft portion 20b of the main shaft 20 is fixed to the pulley 20c, the main shaft portion 20b rotates in the pitch direction in conformity to rotation of the pulley 20c. Thus, manipulation of the pitch direction control manipulator 33 enables the pitch-wise position of the main shaft portion 20b of the main shaft 20 to be controlled on the basis of the direction and amount of the manipulation. In this case, since the driving mechanism causes a mechanism interference, the motors 36a, 36b and 36c need to be manipulated taking interference components into account.

The motor 36b in the driving portion 35 has a driving pulley 37b around its rotating shaft. The wire 50b is hung between the driving pulley 37b and the pulley 17a of the gear 17 in the operating portion 10. Therefore, the pulley 37a functions as a following pulley for the driving pulley 37b. Rotation of the motor 36b enables the pulley 17a to be rotated via the driving pulley 37b and wire 50b. The integration of the pulley 17a with the gear 17 allows the gear 17 to rotate in conformity to rotation of the pulley 17a. Rotation of the gear 17 causes the gripper 12 to be rotated in the yaw direction via the gear portion 22b engaged with the gear 17.

The motor 36c in the driving portion 35 has a driving pulley 37c around its rotating shaft. The wire 50b is hung between the driving pulley 37c and the pulley 18a of the gear 18 in the operating portion 10. Therefore, the pulley 18a functions as a following pulley for the driving pulley 37c. Rotation of the motor 36c enables the pulley 18a to be rotated via the driving pulley 37c and wire 50c. The integration of the pulley 18a with the gear 18 allows the gear 18 to rotate in conformity to rotation of the pulley 18a. A rotate of the gear 18 causes the gripper 11 to be rotated in the yaw direction via the gear portion 23b engaged with the gear 18.

Here, when the yaw direction control manipulator 32 in the manipulating portion 30 is manipulated, the arithmetic processing portion of the driving portion 30 drives the motors 36b and 36c in directions different from each other based on the manipulated direction. This causes the driving pulleys 37b and 37c, provided around the rotating shafts of the motors 36a and 36c, to be rotated in the opposite directions as shown in FIG. 7. As described above with reference to FIG. 2, the gears 17 and 18, used to rotate the gear members 22 and 23 (FIG. 2), are arranged to engage with the gear members 22 and 23 at the position opposite to each other by sandwiching the rotating center axis of the gear members 22 and 23. Accordingly, rotation of the pulleys 17a and 18a in the opposite directions enables the gear portions 22b and 23b to be rotated in the same direction. That is, the grippers 11 and 12 fixed to the gear members 22 and 23, respectively, can be rotated in the same yaw direction.

Figure 8:
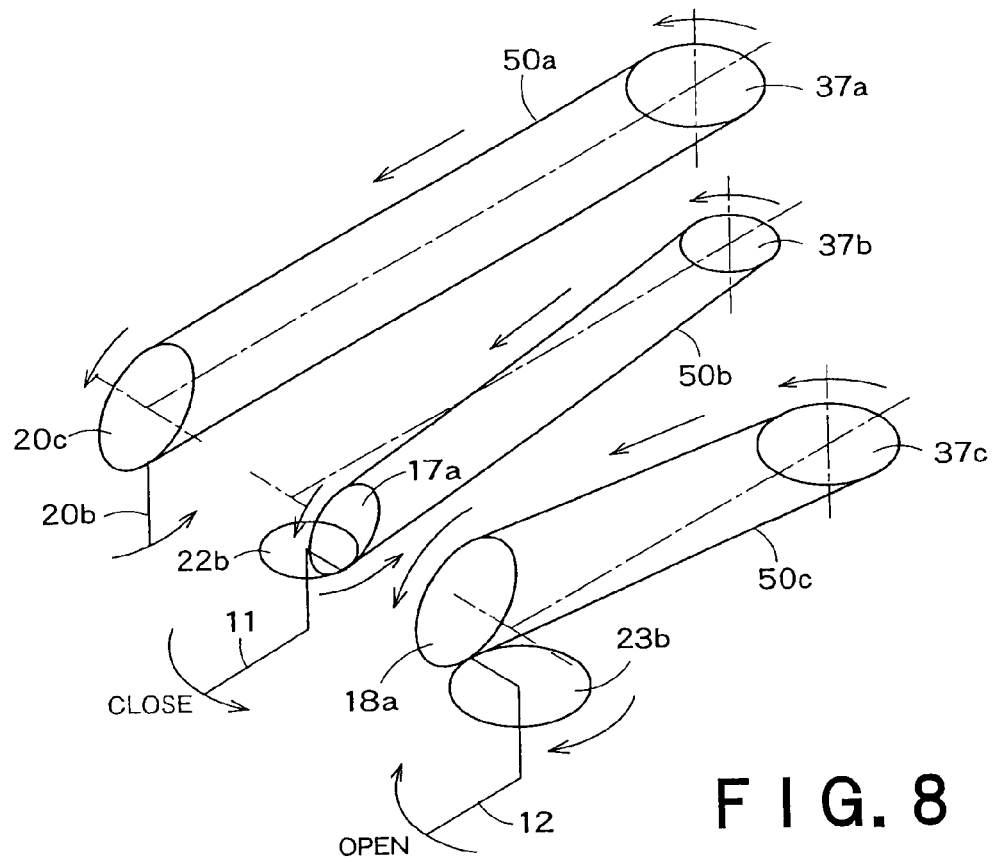
FIG. 8 is an omitted line view showing a wire driving state of the manipulator of FIG. 1.

In contrast, when the gripper opening and closing control manipulator 34 of the manipulating portion 30 is manipulated, the arithmetic processing portion of the driving portion 35 drives the motors 36b and 36c in the same direction based on the result of the manipulation. This causes the gear portions 22b and 23b to be rotated in different directions to enable the grippers 11 and 12 to be closed or opened as shown in FIG. 8.

The driving pulleys 37a, 37b and 37c are in a 90° torsional relationship with the driven pulleys 20c, 17a, and 18a. Therefore, it is possible to mount the relatively heavy motors 36a to 36c in an orthogonal direction (the rotating shafts are oriented in the orthogonal direction). For example, when the motors 36a to 36c are mounted in a horizontal direction (the rotating shafts are oriented in the horizontal direction), moments caused by their weights may act in the direction around the connecting portion 40 to degrade manipulability. In contrast, if the motors 36a to 36c are mounted in the orthogonal direction as shown in the present embodiment, a moment due to the motors 36a to 36c does not occur, and it is possible to prevent degradation of manipulability.

Figure 9:
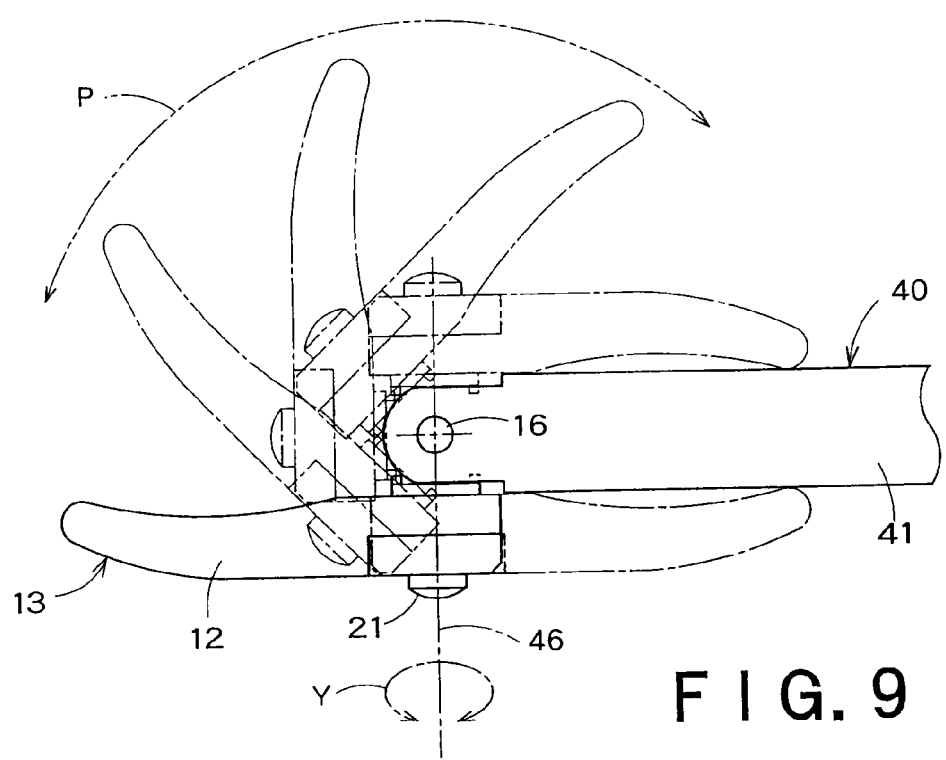
FIG. 9 is an edge view for operational explanation of the manipulator of FIG. 1.

With the manipulator 1 configured as described above, when the pitch direction control manipulator 33 of the manipulating portion 30 (FIG. 1) is manipulated, the grippers 11 and 12 provided at the tip of the main body member 41 of the connecting portion 40 is rotated in the pitch direction "P" centering around the pitch axis (rotor shaft 16), as shown in FIG. 9.

The grippers 11 and 12 are supported at a position offset from the pitch axis (rotor shaft 16) so as to be rotatable in the yaw direction "Y" with respect to the main shaft portion 20b of the main shaft member 20 which is the rotating center axis in the yaw direction "Y". Therefore, it is possible to rotate the grippers 11 and 12 without being interfered with the main body member 41 of the connecting portion 40 as shown in FIG. 9. In particular, as shown by a solid line in FIG. 9, it is possible to rotate the grippers 11 and 12 without being interfered with the main body member 41 of the connecting portion 40 in a state orthogonal to the center axis of the main body member 41 of the connecting portion 40 by 360 degree in the yaw direction.

Therefore, it is possible to control the positions of the grippers 11 and 12 provided at the tip of the connecting portion 10 so as to direct the grippers 11 and 12 from their tips toward the connecting portion 40 as shown in FIG. 10. In this way, By enabling the grippers 11 and 12 to be directed toward the connecting portion 40, it is possible to significantly widen the operating range of the grippers 11 and 12. The operator can thus treat the affected part not only from its front but also by applying the grippers 11 and 12 to the affected part from its rear. The grippers 11 and 12 can also be rotated through 180° around the center axis of the connecting portion 40. This eliminates the need to rotate the grippers through 180° in the pitch direction.

Manipulation of the gripper opening and closing control manipulator 34 of the manipulating portion 30 (FIG. 1) causes the grippers 11 and 12 to be rotated in the direction around the yaw axis (main shaft portion 20b of the main shaft member 20) in the opposite directions so as to be opened or closed as shown in FIG. 11. The grippers 11 and 12 can be rotated around the yaw axis through 360° and can thus be opened and closed to an arbitrary angle. For example, as shown in FIG. 11, the grippers 11 and 12 oriented toward the center axis of the connecting portion 40 can be opened so that each of the grippers 11 and 12 is rotated through 90° (for both grippers 11 and 12, 180°). Furthermore, for example, as shown in FIG. 12, the closed grippers 11 and 12 already rotated through 90° in the yaw axis direction can be opened or closed. In this way, by opening or closing the grippers 11 and 12 already rotated in the yaw direction, it is possible to perform a gripping operation so that the orientation of the operating portion 10 can be varied in the yaw direction. Moreover, the grippers 11 and 12 already rotated in the pitch direction can be opened or closed.

The operator attaches trocars to a number of small holes made in the patient's abdomen. The operator then inserts the manipulator 1, an endoscope, and the like into the abdomen via the trocars and then treats the affected part. The position of tip (operating portion 10) of the manipulator 1 is limited to a movable range around the trocar. However, the grippers 11 and 12 at the tip (operating portion 10) can not only rotate in the pitch direction "P" and yaw directions Y1 and Y2 and perform a gripping operation but can also be rotated through 360° in the yaw direction to treat the affected part from various directions.

To achieve rotating operations in directions around the pitch and yaw axes and a gripping operation, the gear 17, the gear members 22 and 23, and the main shaft 20 are used to change the rotating direction. This allows each of the wires 50a, 50b, and 50c to be most simply disposed using the corresponding pair of pulleys, the pulley 20c, 17a, or 18a and the corresponding driving pulley. Consequently, only tension and unidirectional bending load are applied to each of the wires 50a, 50b, and 50c. This structure can thus suppress a decrease in the strength of the wires compared to complicatedly disposed wires. It also enables the use of wires of much smaller diameters. It can also simplify a manufacture process and a maintenance operation compared to complicatedly disposed wires.

Furthermore, the main shaft portion 20b of the main shaft member 20 rotated in the pitch direction "P", supports the gear members 22 and 23 for rotating in the yaw directions Y1 and Y2, and the grippers 11 and 12. This structure can thus reduce the number of parts required and the weight of the manipulator, and can simplify its configuration compared to support means composed of separate parts.

By eliminating the number of parts in this way, for example, even when there is a limitation to the outer diameter of the manipulator, without downsizing each parts, while holding the strength of each parts, or by enhancing the strength with increase of the size of each parts, it is possible to provide the operating portion 10 in a limited space at the tip of the connecting portion 40, thereby sufficiently ensuring transmission torque and the strength. It is possible to simplify assembly operations by avoiding miniaturization of each parts. Furthermore, it is possible to thicken the support portions 41a and 41b without changing the outer diameter of the connecting portion 40. This enables the improvement of strength of the operating portion 10.

When the longitudinal direction of the grippers 11 and 12 is within the range of ±45° from the direction orthogonal to the yaw axis 46 (main shaft portion 20b of the main shaft member 20), the grippers 11 and 12 can more easily grip the object to be treated. For example, the object to be treated can be more easily gripped by setting the angle θ between the direction orthogonal to the yaw axis 46 (main shaft portion 20b of the main shaft member 20) and the grippers 11 and 12, to be 45° as shown in FIG. 13.

As shown in FIG. 14, the tips of the grippers 11 and 12 are bent so as to overlap the center axis of main body member 41 of the connecting portion 40. Therefore, when the manipulator 1 is rotated around the main body member 41 of the connecting portion 40 (in a roll direction), the tips of the grippers 11 and 12 rotate in the roll direction while overlapping an extension of center axis of the main body member 41. This enables the tips of the grippers 11 and 12 to be easily located.

Second Embodiment

Figure 15:
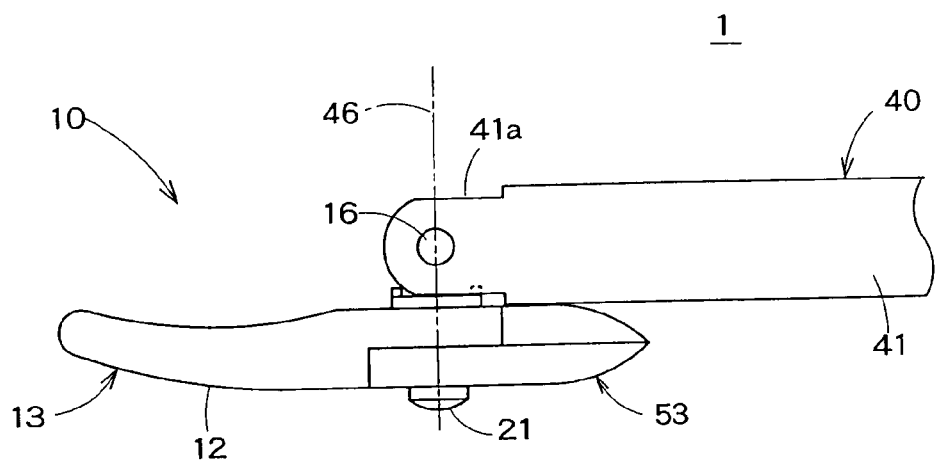
FIG. 15 is an edge view showing the operating portion of the manipulator according to the second embodiment.

A manipulator 1 according to a second embodiment of the present invention includes a gripping forceps 13 serving as a first treating tool portion and a scissor forceps 53 serving as a second treating tool portion in the operating portion 10, as shown in FIG. 15 where components corresponding to those in FIG. 3 are shown by the same reference numerals.

Figure 16:
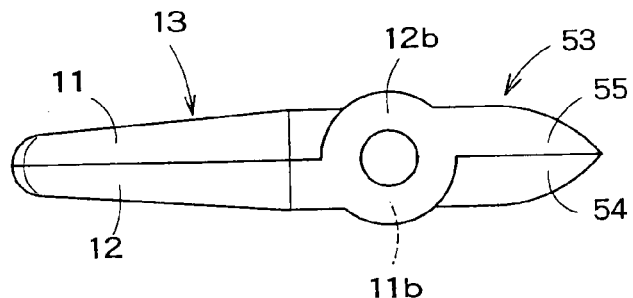
FIG. 16 is a plan view showing the gripper of the manipulator of FIG. 15.
Figure 17:
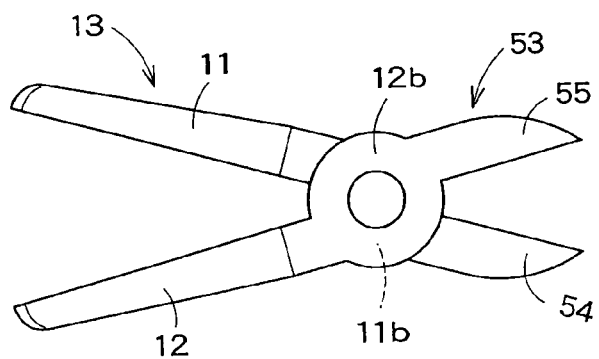
FIG. 17 is a plan view showing the gripper of the manipulator of FIG. 15.

As shown in FIGS. 16 and 17, the scissor forceps 53 are provided opposite to the gripping forceps 13 by sandwiching the support portions 11b and 12b. A cutting edge portion 54 of the scissor forceps 53 is integrated with the gripper 11. A cutting edge portion 55 of the scissor forceps 53 is integrated with the gripper 12. This enables the scissor forceps 53 to be opened or closed by rotating the gears 17 and 18 to open or close the grippers 11 and 12.

With the manipulator 1 configured as described above, the gripping forceps 13 and the scissor forceps 53 can be switched by rotating the two types of forceps in the pitch direction "P". For example, as shown in FIG. 15, at a state that the longitudinal directions of the gripping forceps 13 and the scissor forceps 53 are in parallel to the longitudinal direction of the connecting portion 40, and the gripping forceps 13 projects from the tip of the connecting portion 40, if the gripping forceps 13 and the scissor forceps 53 are rotated by 180° in the pitch direction "P", the gripping forceps 13 is replaced with the scissor forceps 53 and the scissor forceps 53 is projected from the tip of the connecting portion 40 as shown in FIG. 18.

Furthermore, in the state shown in FIG. 15, by rotating the gripping forceps 13 and scissor forceps 53 by 180° in the yaw direction "Y", the gripping forceps 13 is replaced with the scissor forceps 53, and the scissor forceps 53 is projected from the tip of the connecting portion 40 as shown in FIG. 19.

Thus, with the manipulator 1 according to the present embodiment, the two types of forceps (gripping forceps 13 and scissor forceps 53) can be switched simply by rotating the forceps in the pitch direction "P" or yaw direction "Y" with the manipulator 1 remaining inserted into the abdomen. For example, a suturing and ligating operation is performed after a manipulator with a pointer and the manipulator 1 with the gripping forceps 13 and scissor forceps 53 are inserted into the abdomen. Then, the gripping forceps 13 is changed to the scissor forceps 53 without the need to take the manipulator 1 out of the abdomen. The scissor forceps 53 can then be used to cut the suture.

The type of the forceps can thus be changed without the need to take the manipulator 1 out of the abdomen. This enables a reduction in the number of insertions and removals of the manipulator 1 into and from the abdomen.

In the description of the present embodiment, the operating portion 10 is provided with the two types of forceps (gripping forceps 13 and scissor forceps 53). However, forceps of the same type can be symmetrically arranged to increase a compressed area for a compressed operation. The compressed operation refers to an operation of pressing the organs in the vicinity of the affected part in order to, for example, provide an operation area.

Size of the compressed area for the compressed operation can be increased by using a longer forceps to press the organs. Accordingly, when the operating portion 10 is provided with the gripping forceps 13 and a gripping forceps 57 configured similarly to the gripping forceps 13 in the operating portion 10 as shown in FIG. 20, the use of these two forceps (gripping forceps 13 and 57) increases the compressed area owing to their total length L3 compared to the use of one forceps.

Figure 21:
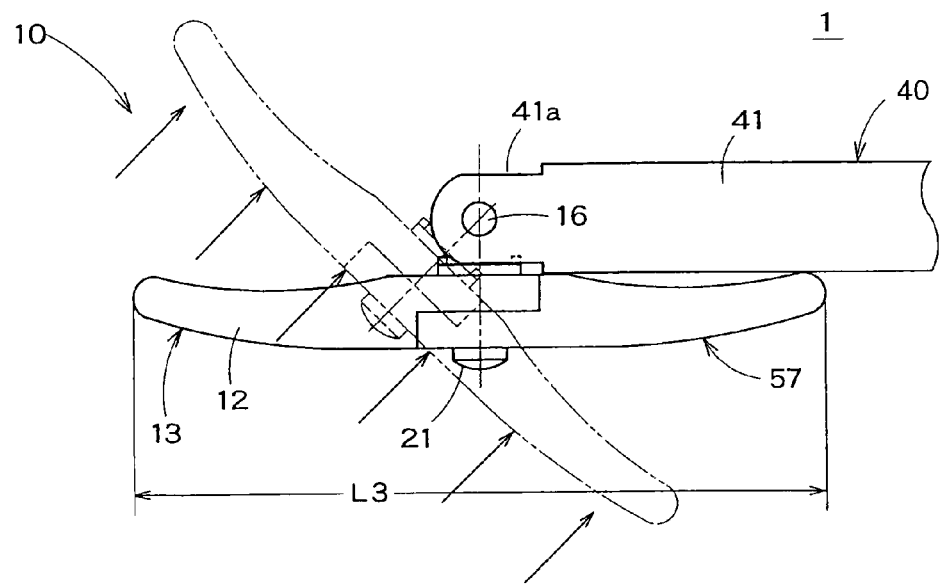
FIG. 21 is an edge view for operational explanation of the gripper of FIG. 20.

As shown in FIG. 21, by rotating the gripping forceps 13 and 57 in the pitch direction to locate them in an compressed operation area, it is possible to perform an compressed operation over the total length L3 of the two gripping forceps 13 and 57.

Figure 22:
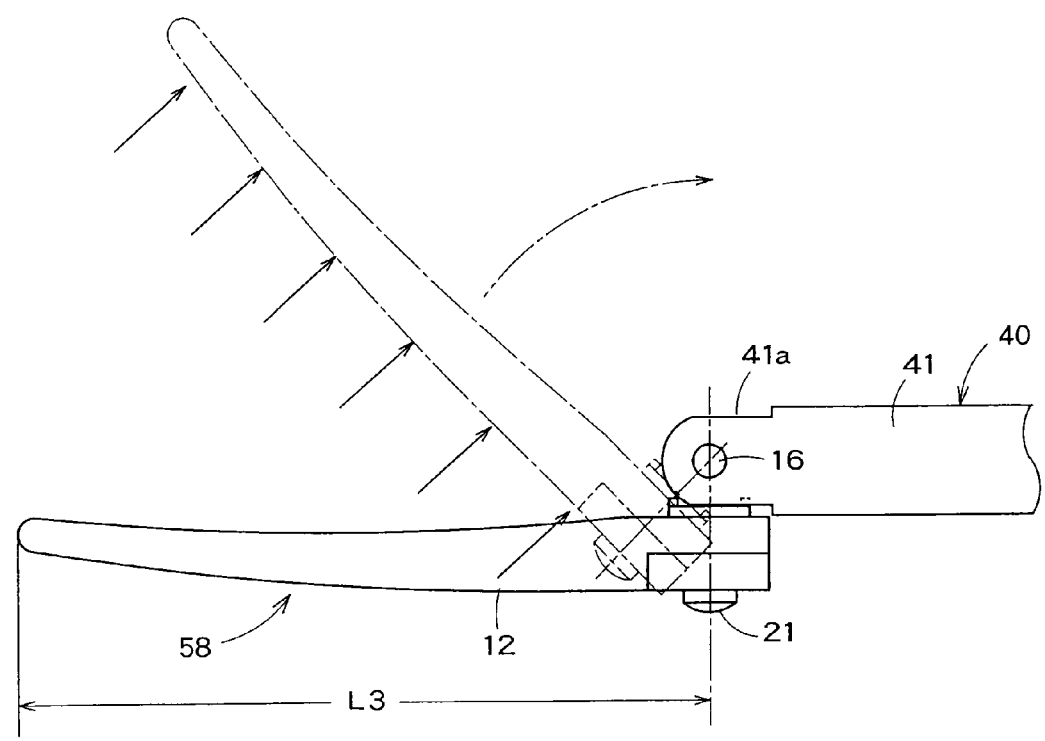
FIG. 22 is an edge view showing a compared example of the gripper.

In the manipulator 1 in accordance with the present embodiment, the two forceps (gripping forceps 13 and 57) are arranged symmetrically with respect to the main shaft portion 20b in order to obtain the length L3. This enables a marked reduction in a moment-induced load imposed on the pitch axis. In contrast, if one forceps 58 has the increased length (L3) and is supported at one end as shown in FIG. 22, an excessive moment-induced load is imposed in a direction around the pitch axis (rotor shaft 16). Such an excessive load acts as a large load for the driving system, resulting in an increase in the size of the driving motor and thus in the weight of the manipulator, degradation of manipulability, a decrease in the strength of the driving system, or damage to the driving system. In contrast, the present embodiment can avoid imposing an excessive moment-induced load on the pitch axis, thus preventing a heavy load from being imposed on the driving system. This makes it possible to avoid an increase in the size of the driving motor and thus in the weight of the manipulator, degradation of manipulability, a decrease in the strength of the driving system, or damage to the driving system.

Figure 24B:
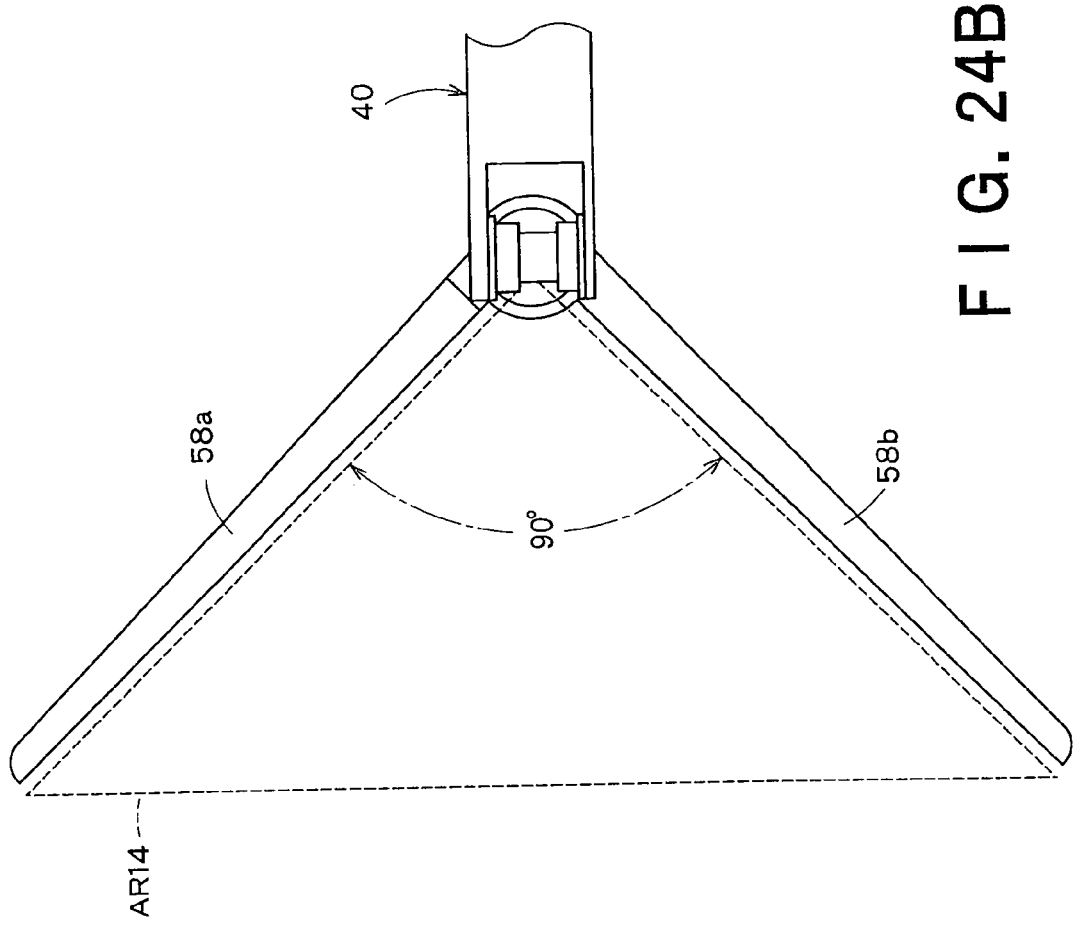
FIGS. 24A-24B are omitted line views showing the compressed area of FIG. 20.
Figure 24A:
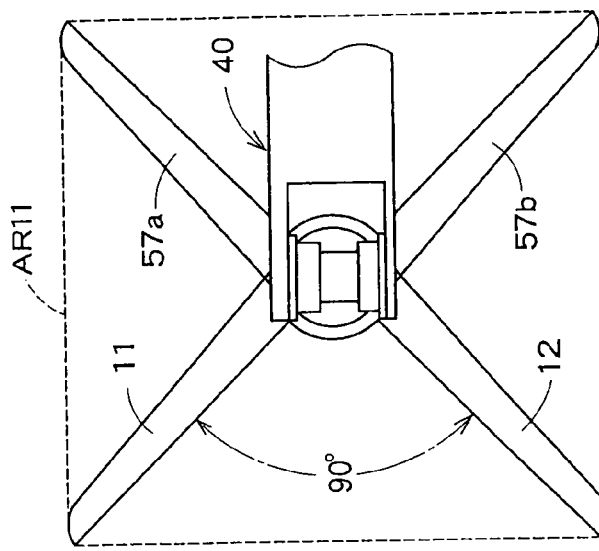

FIG. 23 shows an compressed area AR11 (FIG. 23A) obtained in accordance with the present embodiment if the gripping forceps 13 (11 and 12) and 57 are opened at an angle of aperture of 60° and an compressed area AR12 (FIG. 23B) obtained if only the gripping forceps 58 (grippers 58a and 58b) is opened at an angle of aperture of 60□. FIG. 24 shows an compressed area AR13 (FIG. 24A) obtained in accordance with the present embodiment if the gripping forceps 13 (11 and 12) and 57 are opened at an angle of aperture of 90° and an compressed area AR14 (FIG. 24B) obtained if only the gripping forceps 58 (grippers 58a and 58b) is opened at an angle of aperture of 90°. As shown in FIGS. 23 and 24, the manipulator 1 in accordance with the present embodiment can press a rectangular or square compressed area on its diagonals using its center as a support point, thus performing a stable compressed operation (FIGS. 23A and 24A). In contrast, the one forceps 58 supported at its end presses a triangular area on only two sides of it, resulting in an unstable compressed operation (FIGS. 23B and 24B).

Third Embodiment

Figure 25:
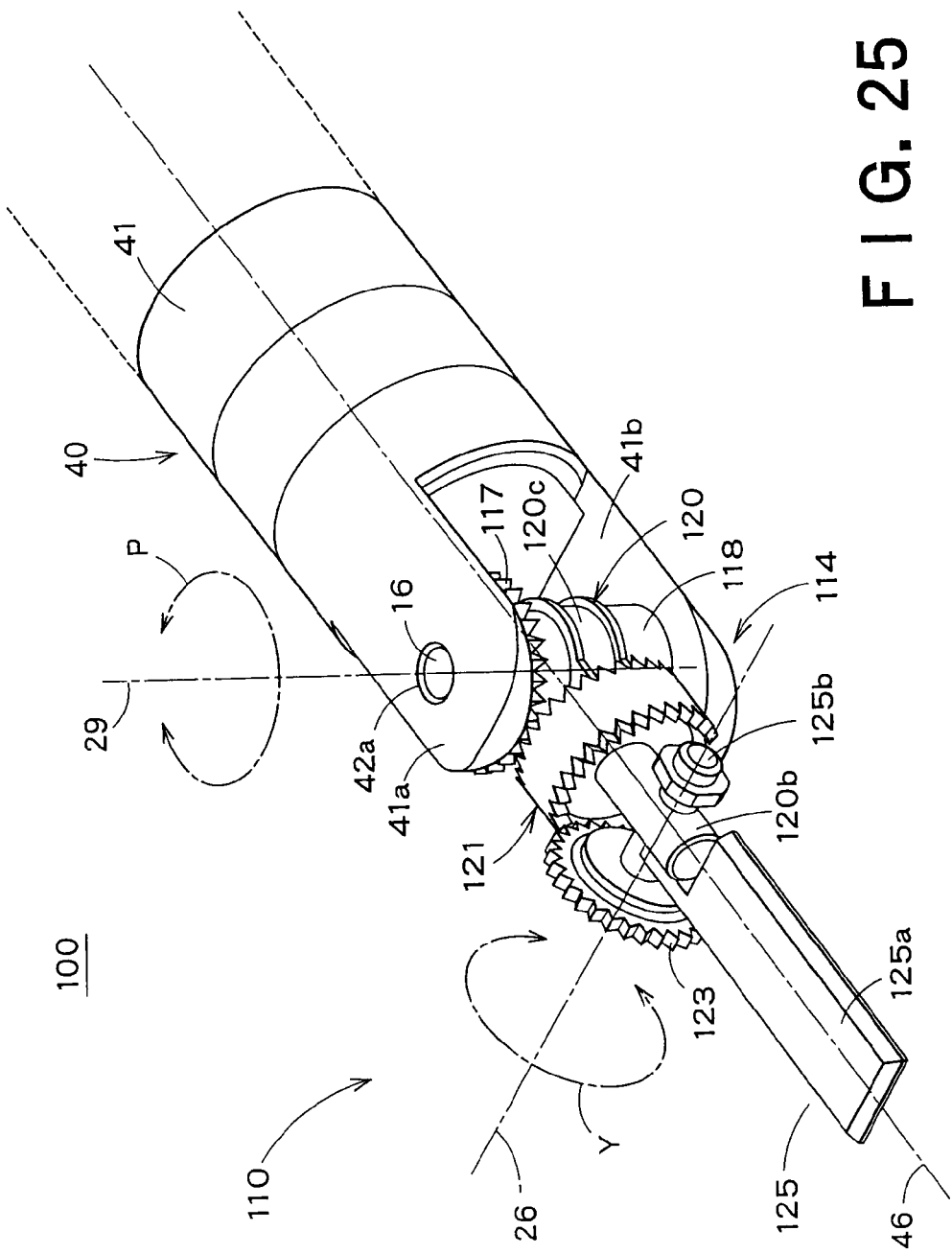
FIG. 25 is a perspective view showing an operating portion of the manipulator according to the third embodiment.
Figure 26:
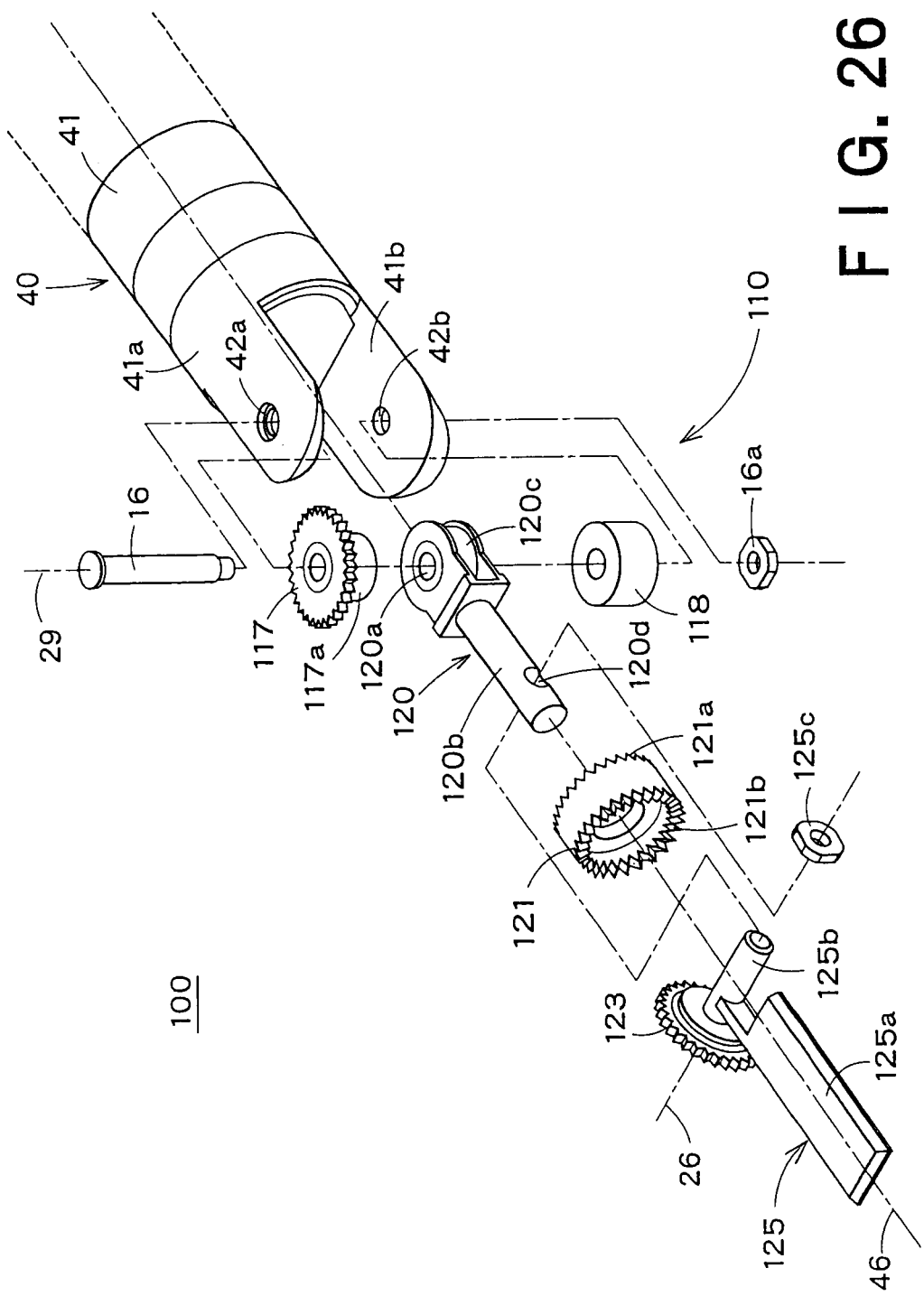
FIG. 26 is an exploded perspective view showing the operating portion of FIG. 25.

A manipulator 100 in accordance with a third embodiment of the present invention is shown in FIGS. 25, 26 and 27 where components corresponding to those in FIGS. 2, 3, and 4 are denoted by the same reference numerals. The manipulator 100 includes the first rotor shaft 16 (rotor axis 29) arranged orthogonal to a direction extending along the longitudinal direction of the connecting portion 40 at a tip of which a treating portion is provided to treat a treatment target, a main shaft 120 which is rotatably supported around the rotor shaft 16 and has a main shaft portion 120b (main axis 46) orthogonal to the rotor shaft 16, a first gear 117 rotatably supported around the first rotor shaft 16, a second gear 121a which engages with the first gear 117 at a state orthogonal to the first gear 117 and is rotatably supported in a direction around the main shaft portion 120b, a third gear 121b which rotates coaxially and together with the second gear 121a, a fourth gear 123 that engages with the third gear 121b at a state orthogonal to the third gear 121b, a second rotor shaft 125b which is in rotation center of the fourth gear 123 and located in a torsional relationship with the first rotor shaft 16, and a treating member 125 which rotates around the second rotor shaft 125b (rotor axis 26) together with the fourth gear 123. That is, the manipulator 100 includes the treating portion 125 that can rotate around the rotor axis 29 in the pitch direction (rotor shaft 16) and the rotor axis 26 in the yaw direction (rotor shaft member 125) so as to change its own position with two degrees of freedom. In this case, since yaw and pitch can be considered to be based on initial positions, there is no problem even in the case where the rotor axis 29 in the yaw direction (rotor shaft 16) and the rotor axis 26 in the pitch direction (rotor shaft 125b) are provided. The cross-sectional view shown in FIG. 27 illustrates the first rotor shaft 16 and the second rotor shaft 125b arranged in torsional relationship by modifying them in parallel positions for convenience of explanation.

That is, the manipulator 100 includes the rotor shaft 16 constituting the rotor axis 29 (pitch axis) arranged orthogonal to the longitudinal direction (center axis direction) of the connecting portion 40, the gear 117 arranged rotatably in the direction of the rotor axis 29, the main shaft 120 supported rotatably in the direction around the rotor axis 29, the gear member 121 having the gear 121a engaging with the gear 117 and the gear 121b formed coaxially and back to back with the gear 121a, and the gear 123 engaging with the gear 121b at a state orthogonal to the gear 121b. The rotor shaft member 125b, serving as a rotating center axis for the gear 123, constitutes the rotor axis 26, and is in torsional relationship with the rotor axis 29. The rotor axis 29 (rotor shaft 16) and rotor axis 26 (rotor shaft member 125b) are offset from each other.

As shown in FIGS. 25, 26, and 27, an operating portion 110 of the manipulator 100 according to the present embodiment includes the treating portion 125 that treats an affected area and a support portion 114 that supports the treating portion 125 so as to be able to change the position at two degrees of freedom.

The gear 117 and the main shaft 120 are rotatably supported on the rotor shaft 16, supported in the cylindrical main body member 41 of the connecting member 40. The rotor shaft 16 is provided with a spacer 118 that regulates the longitudinal positions of the gear 117 and the rotor shaft 16 of the main shaft 120.

A pulley 117a is integrated with the gear 117 concentrically with the rotating center of the gear 117. The gear 117 is rotated by driving the wire 50b (FIG. 27) hung around the pulley 117a.

The main shaft 120 includes a bearing portion 120a rotatably supported around the rotor shaft 16 and the cylindrical main shaft portion 120b fixed to the bearing portion 120a so that its center axis is oriented in the radial direction. A pulley 120c is provided concentrically with the bearing portion 120a. The pulley 120c and the main shaft portion 120b are fixed together. By driving the wire 50a (FIG. 27) hung around the pulley 120c, the main shaft portion 120b can be rotated around the rotor shaft 16 (rotor axis 29) in the pitch direction shown by arrow "P".

The wires hung between the pulleys 117a and 120c and the driving portion 35 (FIG. 1) are passed through the cylindrical main body portion 41 of the connecting portion 40. By manipulating the wires by the manipulating portion 30, it is possible to individually rotate the pulleys 117a and 120c in the direction around the rotor shaft 16.

The gear member 121 is rotatably supported around the main shaft portion 120b of the main shaft 120. The gear member 121 includes the gears 121a and 121b arranged around the main shaft portion 120b and oriented in the extended direction of the center axis of the main shaft portion 120b. The gears 121a and 121b are arranged coaxially and formed in both end faces of the gear member 121, respectively.

The gear 121a engages with the gear 117 at right angle. Therefore, rotation operation centering the rotor shaft 16 is converted into rotation operation centering the main shaft portion 120b orthogonal to the center axis of the rotor shaft 16.

The gear 123 engages with the gear 121b of the gear member 121 in an orthogonal state. The rotor shaft member 125b, constituting the rotating center axis of the gear 123, is rotatably supported in a through-hole 120d formed in the main shaft portion 120b of the main shaft 120. The rotor shaft member 125b is prevented by a nut 125c from slipping out of the through-hole 120d. In this way, a rotating operation of the gear 121b in the direction around the main shaft portion 120b is converted into a rotating operation centering the rotor shaft member 125b (rotor axis 26) in the yaw direction "Y". The rotor shaft member 125b turns in conformity to a rotating operation of the gear 123. A planar metallic treating member 125a is fixed to the rotor shaft member 125b and turns in the yaw direction "Y" in conformity to a rotating operation of the rotor shaft member 125b.

Thus, in accordance with rotation of the pulley 117a by the wire 50b, the gear member 121, gear 123, and rotor shaft member 125b rotate. This enables the treating member 125a to be rotated in the yaw direction "Y".

When the pulley 120c is rotated by the wire 50a, in accordance with the rotation, the main shaft portion 120b of the main shaft 120 is rotated in the pitch direction "P". This enables the treating member 125a engaged with the main shaft 120b via the rotor shaft member 125b to be rotated in the pitch direction "P".

The wire 50a can be driven by the motor through manipulation of the pitch direction control manipulator 33 of the manipulating portion 30, described above with reference to FIG. 1. The wire 50b can be driven by the motor through manipulation of the yaw direction control manipulator 32.

Electricity is conducted through the treating member 125a via the main body member 41 of the connecting portion 40 formed of metal. This allows the treating member 125a to be used as an electric scalpel.

With the manipulator 100 in accordance with the present embodiment, if only the pulley 120c of the main shaft 120 is rotated by driving only the wire 50a, the gear member 121 relatively rotates in the direction around the main shaft portion 120b unless the gear 117 is moved. To avoid such mechanism interference, rotating angles are set as shown by:

$$\theta a = \theta 1 + \theta 2$$

$$\theta b = \theta 1$$

where θ1 denotes the rotating angle in the direction around the rotor shaft 16 (rotor axis 29), θ2 denotes the rotating angle in the direction around the rotor shaft member 125b (rotor axis 26), θa denotes the rotating angle of the gear 117, θb denotes the rotating angle of the main shaft portion 120b, the gears 117 and 123 have the same number of teeth, and the gears 121a and 121b have the same number of teeth. Taking the mechanism interference into account, the driving portion 35 (FIG. 1) controllably drives the wires 50a and 50b on the basis of manipulation instructions from the manipulating portion 30. The arrangements for the mechanism interference are similar to those in the other embodiments and thus will not be described in these embodiments.

In the manipulator 100 described above, the treating member 125a can change its position between two degrees of freedom, that is, between a rotating operation in the direction around the rotor axis 29 (rotor shaft 16) and a rotating operation in the direction around the rotor axis 26 (rotor shaft member 125b). A rotating operation in the direction around the main axis 46 can also be performed by rotating the entire manipulator 100 in the direction around the main body member 41 of the connecting portion 40. This requires only two driving motors for the wires 50a and 50b.

To achieve an a rotating operation in the direction around the rotor axis 29 and a rotating operation in the direction around the rotor axis 26, the rotating direction is changed using the gear 117, the gear member 121, the gear 123, and the main shaft 120. This allows each of the wires 50a and 50b to be most simply disposed using the corresponding pair of pulleys, the pulley 120c or 117a and the corresponding driving pulley. Consequently, tension and unidirectional bending load are applied to each of the wires 50a and 50b. This structure can thus suppress a decrease in the strength of the wires compared to complicatedly disposed wires. It also enables the use of wires of much smaller diameters. It can also simplify the manufacture process and the maintenance operation compared to complicatedly disposed wires.

The gears 117, 123, 121a, and 121b may have an arbitrary combination of the numbers of teeth. By providing the gears 117 and 123 with the same number of teeth and providing the gears 121a and 121b of the gear member 121 with the same number of teeth, it is possible to use the same parts or machining tools, thus simplifying the manufacture process.

A reduction in the number of teeth in the gears 121b and 123 allows the size of the operating portion 110 to be reduced. The combination of the numbers of teeth is similar to those in the other embodiments and thus will be omitted in these embodiments.

The main shaft portion 120b of the main shaft 120 for rotating in the pitch direction "P" supports both of the gear member 121 for rotating in the yaw direction "Y" and the treating member 125a. Therefore, as compared with the case where these supporting members are composed of separate parts, it is possible to reduce the number of parts, thereby realizing light-weight and simplified configuration.

Furthermore, by reducing the number of parts in this way, even when there is a limitation to the outer diameter of the manipulator, without downsizing each parts, while holding the strength of each parts, or by enhancing the strength with increase of the size of each parts, it is possible to provide the operating portion 110 in a limited space at the tip of the connecting portion 40, thereby sufficiently ensuring transmission torque and the strength. It is possible to simplify assembly operations by avoiding miniaturization of each parts.

In the present embodiment, the planar treating member 125a is used as the treating portion 125. However, the present invention is not limited to this. Various shapes such as an L shape may be used for the treating portion 125. Furthermore, the main body member 41, main shaft 120, and rotor shaft 16 can be utilized to make the relevant components including the treating portion 125 conductive. In this case, for example, an insulating portion may be provided around the outer peripheral part of the main body member 41. The treating portion 125 may be adapted for various applications instead of being composed of an electric scalpel; the treating portion 125 may be used to press, draw, or cut the affected part. The treating portions may also be detachable from the gear 123 and thus replaceable or may have its orientation arbitrarily varied.

Fourth Embodiment

Figure 28:
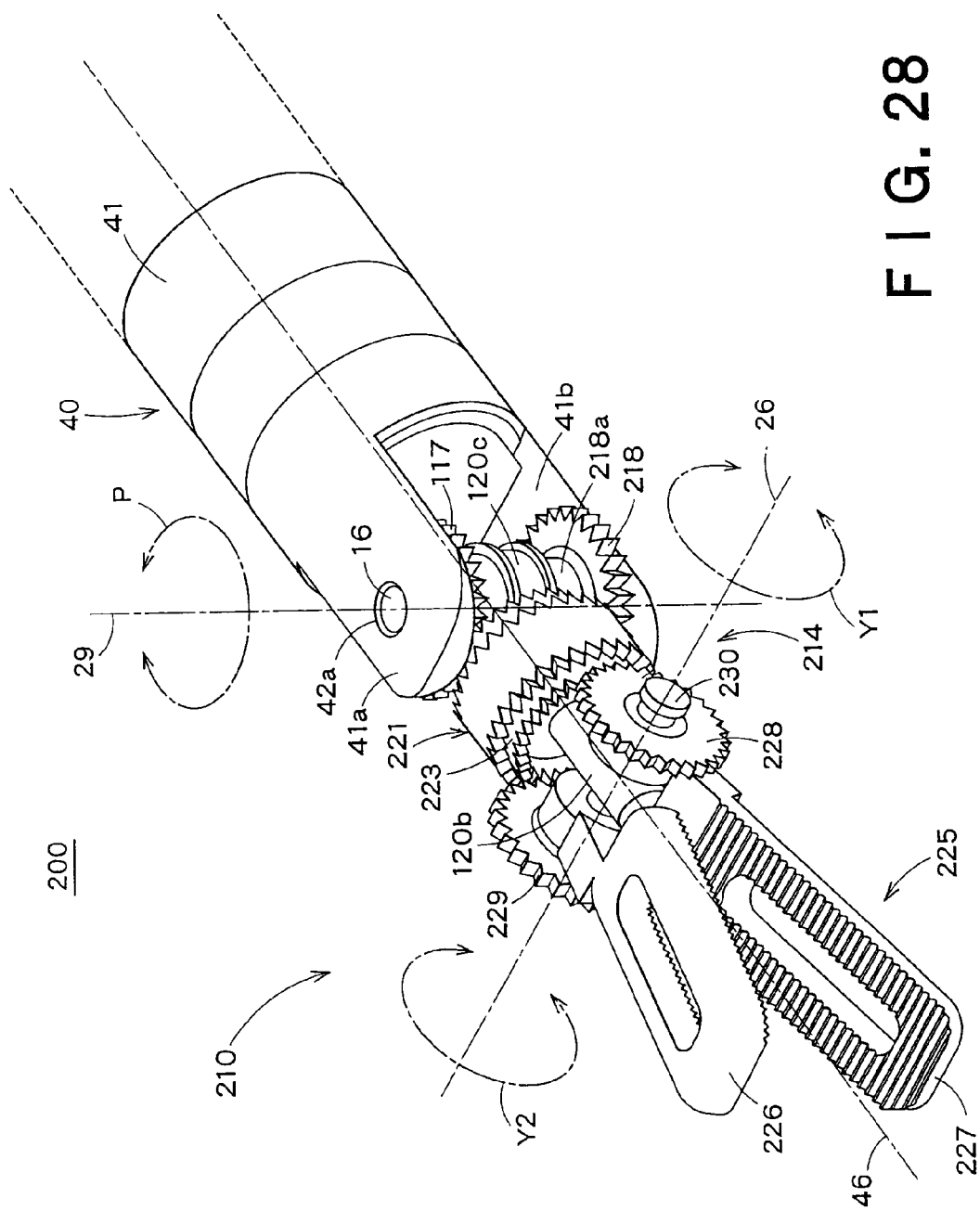
FIG. 28 is a perspective view showing the operating portion of the manipulator according to the fourth embodiment.
Figure 29:
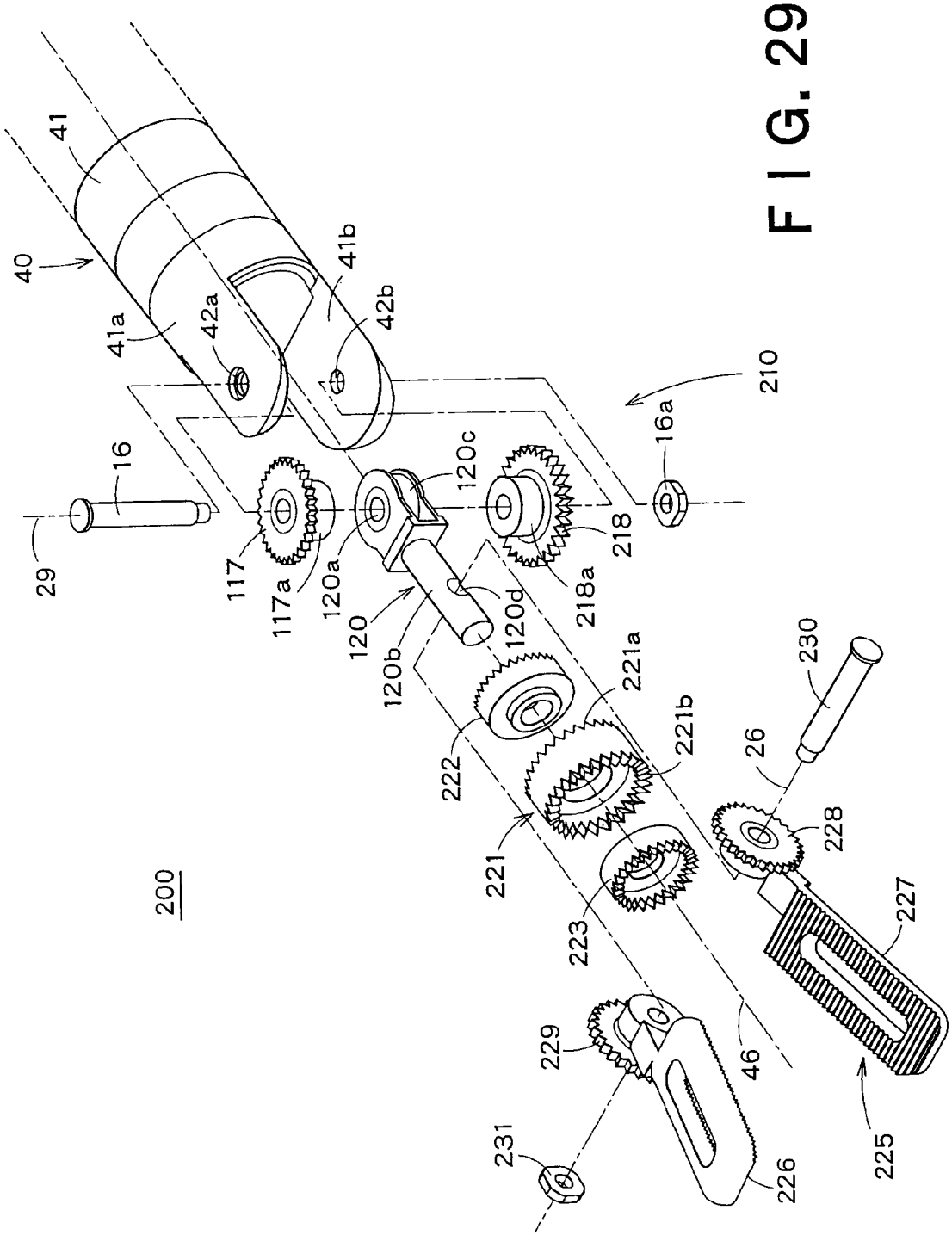
FIG. 29 is an exploded perspective view showing the operating portion of FIG. 28.
Figure 30:
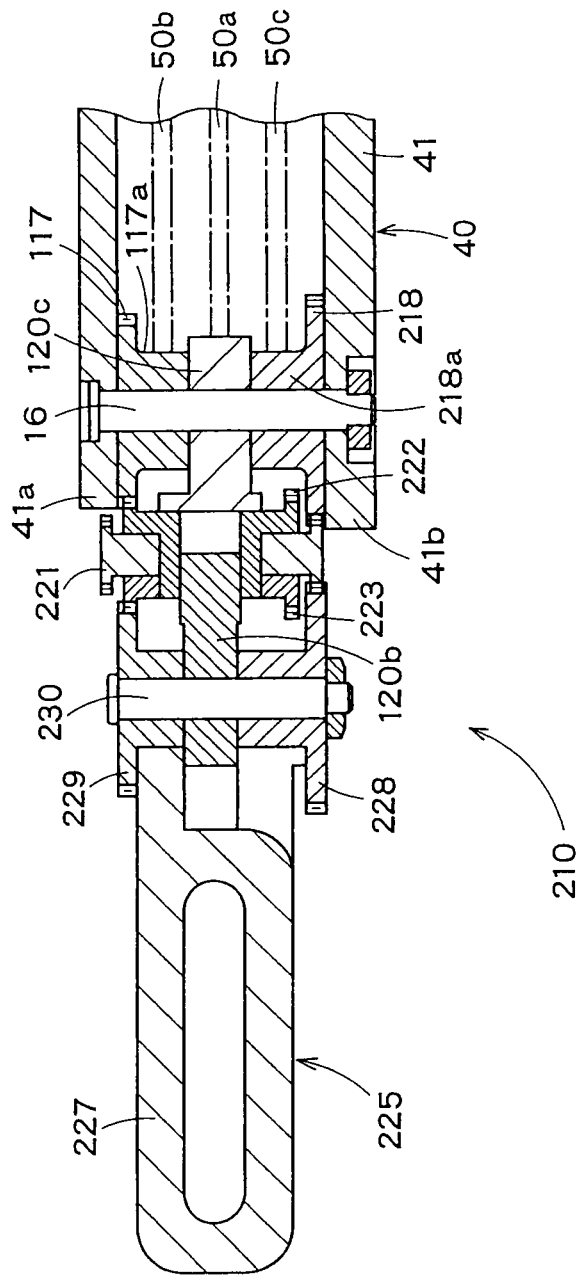
FIG. 30 is a cross-sectional view showing the operating portion of FIG. 28.

A manipulator 200 in accordance with a fourth embodiment of the present invention is shown in FIGS. 28, 29, and 30 where components corresponding to those in FIGS. 25, 26, and 27 are denoted by the same reference numerals. The manipulator 200 includes the first rotor shaft 16 (rotor axis 29) arranged orthogonal to the direction along the longitudinal direction of the connecting portion 40 at the tip of which a treating portion 225 is provided to treat a treatment target, the main shaft 120 which is rotatably supported in the direction around the rotor shaft 16 and has the main shaft portion 120b arranged orthogonal to the rotor shaft 16, the first gear 117 rotatably supported in the direction around the first rotor shaft 16, a second gear 218 rotatably supported in the direction around the first rotor shaft 16, a third gear 222 which engages with the first gear 117 at right angle and is rotatably supported in the direction around the main shaft portion 120b, a fourth gear 221a which engages with the second gear 218 at right angle and which is rotatably supported in the direction around the main shaft portion 120b, a fifth gear 223 which rotates coaxially and together with the third gear 222, a sixth gear 221b which rotates coaxially and together with the fourth gear 221a, a seventh gear 229 engaging with the fifth gear 223 at right angle, an eighth gear 228 engaging with the sixth gear 221b at right angle, a second rotor shaft 230 around which the seventh gear 229 and the eighth gear 228 rotate and which is located in a torsional relationship with the first rotor shaft 16, a first treating member 226 which rotates around the second rotor shaft 230 (rotor axis 26) together with the seventh gear 229, and a second treating member 227 which rotates around the second rotor shaft 230 together with the eighth gear 228. That is, the manipulator 200 includes the treating portion 225 that can rotate around the rotor axis 29 (rotor shaft 16) and the rotor axis 26 (rotor shaft 230) so as to change its own position between two degrees of freedom. The treating portion 225 can also perform a gripping operation by rotating around the rotor axis 26 (rotor shaft 230) so as to be opened or closed. The cross-sectional view shown in FIG. 30 illustrates the first rotor shaft 16 and the second rotor shaft 230 arranged in torsional relationship by modifying them in parallel positions for convenience of explanation.

That is, the manipulator 200 includes the rotor shaft 16 constituting the rotor shaft 29 (pitch axis) arranged orthogonal to the longitudinal direction (center axis direction) of the connecting portion 40, the two gears 117 and 218 arranged so as to be rotatable in the direction around the rotor shaft corresponding to the rotor axis 29, the main shaft 120 rotatably supported in the direction around the rotor shaft corresponding to the rotor axis 29, the gear 222 engaging with the gear 117 at right angle, the gear 223 provided coaxially and back to back with the gear 222 and rotating integrally with the gear 222, the gear 228 engaging with the gear 223 at right angle, the gear 221a engaging with the gear 218 while crossing the gear 218 at right angle, the gear 221b provided coaxially and back to back with the gear 221a and rotating integrally with the gear 221a, the gear 228 engaging with the gear 221b at right angle, the treating member 227 rotating in the direction around the rotor axis 26 integrally with the gear 228, and the treating member 226 rotating in the direction around the rotor axis 26 integrally with the gear 229. The rotor shaft 230, serving as a rotating center axis for the gears 228 and 229, constitutes the rotor axis 26 and is in a torsional or parallel relationship with the rotor axis 29. The rotor axis 29 (rotor shaft 16) and rotor axis 26 (rotor shaft member 230) are offset from each other.

As shown in FIGS. 28, 29, and 30, the operating portion 210 of the manipulator 200 in accordance with the present embodiment includes the treating portion 225 that treats the affected part and a support portion 214 that supports the treating portion 225 so that the treating portion 225 can change its position between the two degrees of freedom and perform a gripping operation.

The gears 117 and 218 and the main shaft 120 are rotatably supported on the rotor shaft 16, supported in the cylindrical main body member 41 of the connecting portion 40.

The pulley 117a is integrated with the gear 117 concentrically with the rotating center of the gear 117. The gear 117 is rotated by driving the wire 50b (FIG. 30) hung around the pulley 117a. The pulley 218a is integrated with the gear 218 concentrically with the rotating center of the gear 218. The gear 218 is rotated by driving the wire 50c (FIG. 30) hung around the pulley 218a.

The main shaft 120 includes the bearing portion 120a rotatably supported around the rotor shaft 16 and the cylindrical main shaft portion 120b fixed to the bearing portion 120a so that its center axis is oriented in the radial direction. The pulley 120c is provided concentrically with the bearing portion 120a. The pulley 120c and the main shaft portion 120b are fixed together. By driving the wire 50a (FIG. 30) hung around the pulley 120c, the main shaft portion 120b can be rotated around the rotor shaft 16 (rotor axis 29) in the pitch direction shown by arrow "P".

The wires 50a, 50b, and 50c hung between the pulleys 117a, 218a, and 120c and the manipulating portion 30 (FIG. 1) are passed through the cylindrical main body portion 41 of the connecting portion 40. By using the manipulating portion 30 to manipulate the wires, the pulleys 117a, 218a, and 120c can be individually rotated around the rotor shaft 16.

The gears 222 and 223 and the gear member 221 are rotatably supported around the main shaft portion 120b of the main shaft 120c. The gears 222 and 223 rotate integrally around the main shaft portion 120c. The gear 222 engages with the gear 117 at right angle. Therefore, rotation operation centering the rotor shaft 16 is converted into rotation operation centering the main shaft portion 120b orthogonal to the center axis of the rotation shaft 16.

The gear member 221 includes the gears 221a and 221b arranged around the main shaft portion 120b and oriented in the extended direction of the center axis of the main shaft portion 120b. The gears 221a and 221b are coaxially arranged at both end faces of the gear member 221.

The gear 221a engages with the gear 218 at right angle. Therefore, rotation operation centering the rotor shaft 16 is converted into rotation operation centering the main shaft portion 120b orthogonal to the rotor shaft 16.

The gear 229 engages with the gear 223 at right angle. The gear 229 is rotatably supported around the rotor shaft 230, which is supported in the through-hole 120d formed in the main shaft portion 120b of the main shaft 120. The rotor shaft 230 is prevented by a nut 231 from slipping out of the through-hole 120d. A rotating operation of the gear 223 in the direction around the main shaft portion 120b is converted into a rotating operation around the rotor shaft 230 (rotor axis 26) in the yaw direction "Y1". The treating member 226 is fixed to the gear 229 and turns integrally with the gear 229 in the yaw direction "Y1".

The gear 228 engages with the gear 221b at right angle. The gear 228 is rotatably supported around the rotor shaft 230. A rotating operation of the gear 221b around the main shaft portion 120b is thus converted into a rotating operation around the rotor shaft 230 (rotor axis 26) in the yaw direction "Y2". The treating member 227 is fixed to the gear 228 and turns integrally with the gear 228 in the yaw direction "Y2".

Thus, rotating the pulley 117a via the wire 50b causes the gears 117, 222, 223, and 229 to be correspondingly turned. This enables the treating member 226 to be rotated in the yaw direction "Y1".

When the wire 50c rotates the pulley 218a, the gear member 221, and the gear 228 can be correspondingly rotated. This enables the treating member 227 to be rotated in the yaw direction "Y2".

When the wire 50a rotates the pulley 120c, the main shaft portion 120b of the main shaft 120 can be rotated in the pitch direction "P". This enables the treating members 226 and 227 engaged with the main shaft 120b via the rotor shaft 230 to be rotated in the pitch direction "P".

The wire 50a can be driven by the motor through manipulation of the pitch direction control manipulator 33 of the manipulating portion 30, described above with reference to FIG. 1. The wires 50b and 50c can be driven by the motor through manipulation of the yaw direction control manipulator 32. The wires 50b and 50c can also be driven by the motor using the gripper opening and closing control manipulator 34.

When the gears 117 and 218 are rotated in the same direction via the wires 50b and 50c, the gears 222 and 223 and the gear member 221 rotate in an opposite direction. The gears 228 and 229 thus rotate in the same direction. Therefore, the treating members 226 and 227 rotate in the same yaw direction. The treating members 226 and 227 of the treating portion 125 perform a yaw operation in the same direction while remaining closed or open.

When the gears 117 and 218 are rotated in the opposite directions via the wires 50b and 50c, the gears 222 and 223 and the gear member 221 rotate in the same direction. The gears 228 and 229 thus rotate in the opposite directions. Therefore, the treating members 226 and 227 rotate in an opposite yaw directions. The treating members 226 and 227 of the treating portion 125 perform a gripping operation in the direction in which the treating members 226 and 227 are closed or opened.

The manipulator 200 in accordance with the present embodiment also causes the mechanism interference described above in the third embodiment. Thus, taking the mechanism interference into account, the driving portion 35 (FIG. 1) controllably drives the wires 50a, 50b, and 50c on the basis of manipulation instructions from the manipulating portion 30.

In the manipulator 200 described above, the treating members 226 and 227 can change their positions between two degrees of freedom, that is, between a rotating operation in the direction around the rotor axis 29 (rotor shaft 16) and a rotating operation in the direction around the rotor axis 26 (rotor shaft 230). A rotating operation around the roll axis can also be performed by rotating the entire manipulator 200 in the direction around the main body member 41 of the connecting portion 40.

To achieve an a rotating operation in the direction around the rotor axis 29 and a rotating operation in the direction around the rotor axis 26, the rotating direction is changed using the gears 117, 218, 222, and 223, the gear member 221, the gears 228 and 229, and the main shaft 120. This allows each of the wires 50a, 50b, and 50c to be most simply disposed using the corresponding pair of pulleys, the pulley 120c, 117a, or 218a and the corresponding driving pulley. Consequently, tension and unidirectional bending load are applied to each of the wires 50a, 50b, and 50c. This structure can thus suppress a decrease in the strength of the wires compared to complicatedly disposed wires. It also enables the use of wires of much smaller diameters. It can also simplify the manufacture process compared to complicatedly disposed wires.

Furthermore, the main shaft portion 120b of the main shaft 120, rotating in the pitch direction "P", supports both the gear member 221, enabling turns in the yaw direction "Y", and the treating members 226 and 227. This structure can thus reduce the number of parts required and the weight of the manipulator and simplify its configuration compared to support means composed of separate parts.

By reducing the number of the number of parts, even when there is a limitation to the outer diameter of the manipulator, without downsizing each parts, while holding the strength of each parts, or by enhancing the strength with increase of the size of each parts, it is possible to provide the operating portion 110 in a limited space at the tip of the connecting portion 40, thereby sufficiently ensuring transmission torque and the strength. It is possible to simplify assembly operations by avoiding miniaturization of each parts.

Fifth Embodiment

Figure 31:
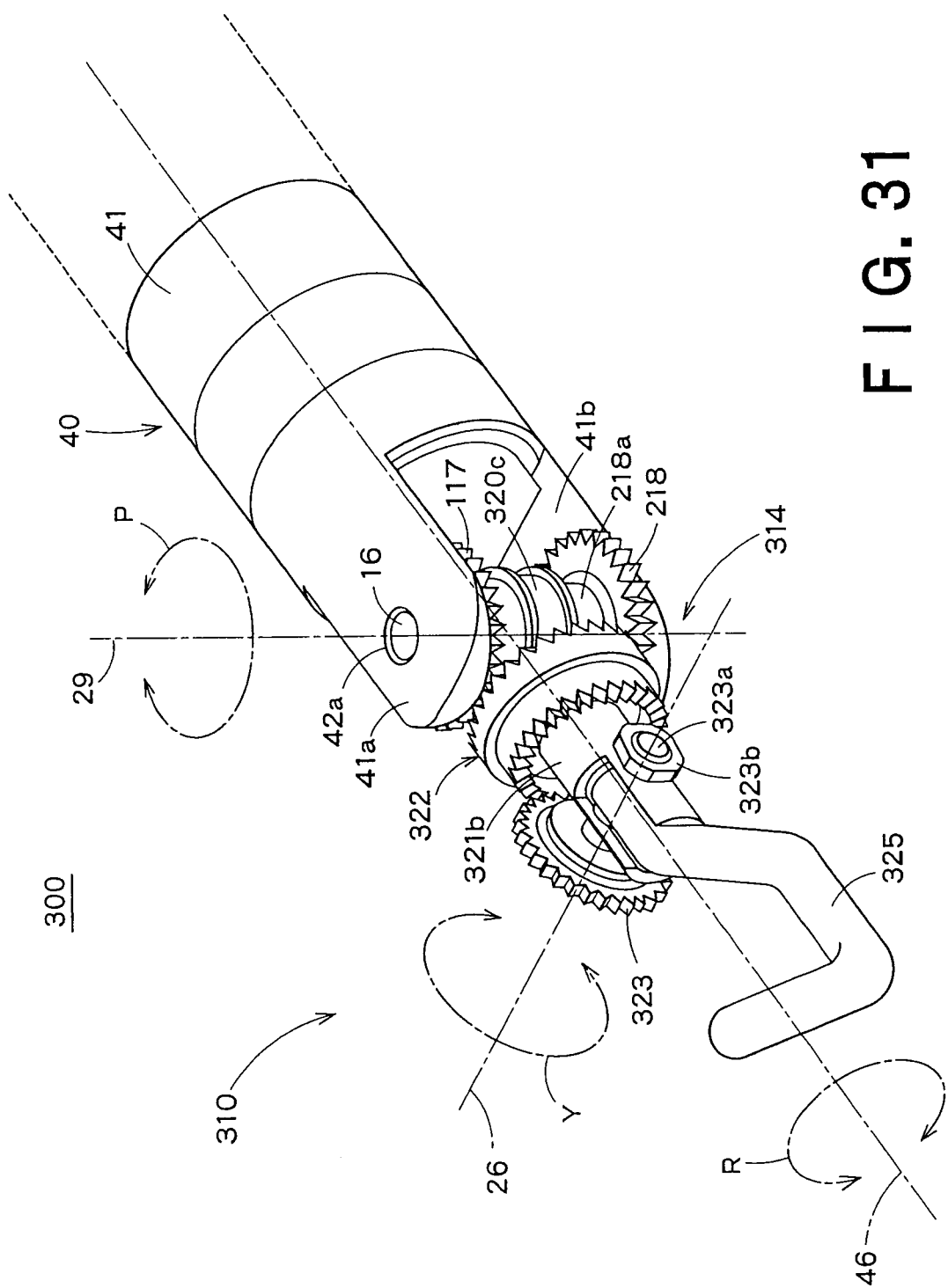
FIG. 31 is a perspective view showing the operating portion of the manipulator according to the fifth embodiment.
Figure 32:
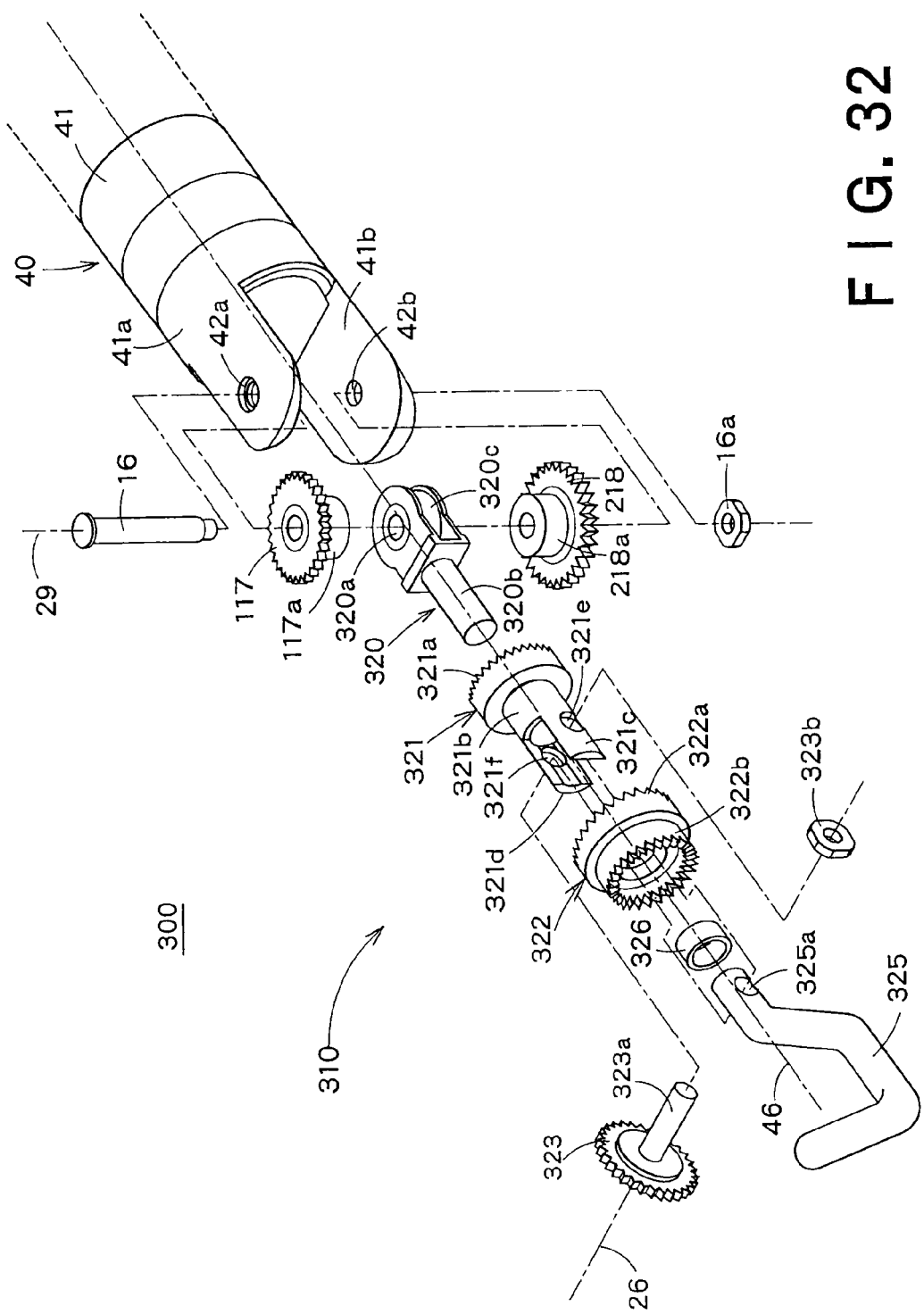
FIG. 32 is an exploded perspective view showing the operating portion of FIG. 31.

A manipulator 300 according to a fifth embodiment of the present invention is shown in FIGS. 31, 32, and 33 where components corresponding to those in FIGS. 28, 29, and 30 are denoted by the same reference numerals. The manipulator 300 includes the first rotor shaft 16 (rotor axis 29) arranged orthogonal to the direction along the longitudinal direction of the connecting portion 40 at a tip of which a treating portion 325 is provided to treat a treatment target, a main shaft member 320 which is rotatably supported around the first rotor shaft 16 and has a main shaft portion 320b arranged orthogonal to the first rotor shaft 16, the first gear 117 rotatably supported in the direction around the first rotor shaft 16, the second gear 218 rotatably supported in the direction around the first rotor shaft 16, a third gear 321a which engages with the first gear 117 at right angle and is rotatably supported in the direction around the main shaft portion 320b (main axis 46), a fourth gear 322a which engages with the second gear 218 at right angle and is rotatably supported in the direction around the main shaft portion 320b, a second rotor shaft 321b when rotates coaxially and together with the third gear 321a, a fifth gear 322b which rotates coaxially and together with the fourth gear 322a, a third rotor shaft 323a which crosses the second rotor shaft 321b at right angle and rotates in the direction around the main shaft portion 320b in conformity to rotation of the second rotor shaft 321b, the third rotor shaft 323a being located so as to be rotatable from a torsional position to a parallel position with respect to the first rotor shaft 16, a sixth gear 323 which is rotatably supported around the third rotor shaft 323a (rotor axis 26) and engages with the fifth gear 322b at right angle, and a treating member 325 which rotates around the third rotor shaft 323a together with the sixth gear 323. That is, the manipulator 300 includes the treating portion 325 which can rotate around the rotor axis 29 in the pitch direction, the rotor axis 26 in the yaw direction, and the main axis 46 in the roll direction so as to change its own position among three degrees of freedom.

That is, the manipulator 300 includes the rotor shaft 16 constituting the rotor shaft (rotor axis 29) arranged orthogonal to the longitudinal direction (center axis direction) of the connecting portion 40, the two gears 117 and 218 arranged so as to be rotatable in the direction around the rotor axis 29, the main shaft 320 rotatably supported in the direction around the rotor axis 29, the gear 321a engaging with the gear 117 at right angle, the bearing portion 321b rotating integrally with the gear 321a, the gear 322a engaging with the gear 218 at right angle, the gear 322b provided coaxially and back to back with the gear 322a and rotating integrally with the gear 322a, the gear 323 which engages with the gear 322b at right angle, and the treating member 325 which rotates around the rotor axis 26 integrally with the gear 323. The rotor shaft member 323a, serving as a rotating center axis for the gear 323, constitutes the rotor axis 26 and is in a torsional or parallel relationship with the rotor axis 29.

As shown in FIGS. 31, 32, and 33, the operating portion 310 of the manipulator 300 in accordance with the present embodiment includes the treating portion 325 which treats the affected part and a support portion 314 which supports the treating portion 325 so that the treating portion 325 can change its position among the three degrees of freedom.

The gears 117 and 218 and the main shaft 120 are rotatably supported on the rotor shaft 16, supported in the cylindrical main body member 41 of the connecting member 40.

The pulley 117a is integrated with the gear 117 concentrically with the rotating center of the gear 117. The gear 117 is rotated by driving the wire 50b (FIG. 33) hung around the pulley 117a. The pulley 218a is integrated with the gear 218 concentrically with the rotating center of the gear 218. The gear 218 is rotated by driving the wire 50c (FIG. 33) hung around the pulley 218a.

The main shaft member 320 includes a bearing portion 320a rotatably supported around the rotor shaft 16 and a cylindrical main shaft portion 320b fixed to the bearing portion 320a so that its center axis is oriented in the radial direction. A pulley 320c is provided concentrically with the bearing portion 320a. The pulley 320c and the main shaft portion 320b are fixed together. By driving the wire 50a (FIG. 33) hung around the pulley 320c, the main shaft portion 320b can be rotated around the rotor shaft 16 (rotor axis 29) in the pitch direction shown by arrow "P".

The wires 50a, 50b, and 50c hung between the pulleys 117a, 218a, and 320c and the manipulating portion 35 (FIG. 1) are passed through the cylindrical main body portion 41 of the connecting portion 40. When the manipulating portion 30 manipulates these wires, the pulleys 117a, 218a, and 320c can be individually rotated in the direction around the rotor shaft 16.

A roll member 321 integrating the gear 321a and the bearing portion 321b, and a gear member 322 are rotatably supported around the main shaft portion 320b of the main shaft member 320. The gear 321a engages with the gear 117 at right angle. Therefore, rotation operation centering the rotor shaft 16 is converted into rotation operation centering the main shaft portion 320b orthogonal to the rotation shaft 16. The cylindrical bearing portion 321b of the roll member 321, integrated with the gear 321a, is rotatably supported in the direction around the main shaft portion 320b of the main shaft member 320 (rotated around the main axis 46 in the roll direction "R"). A pair of support portions 321c and 321d is formed on the bearing portion 321b so that the support portions 321c and 321d are arranged opposite to each other. Through-holes 321e and 321f are formed in the support portions 321c and 321d, respectively. The rotor shaft member 323a of the gear 323 is rotatably inserted through the through-holes 321e and 321f. The rotor shaft member 323a is prevented by a nut 323b from slipping out of the through-holes 321e and 321f. The rotor shaft member 323a is fitted into a fitting hole 325a in the treating member 325. The roll member 321 is prevented by the nut 326 from slipping out of the main shaft portion 320b.

Thus, when the roll member 321 rotates in the roll direction "R" in conformity to a rotating operation of the gear 117, the rotor shaft member 323a and the treating member 325 fitted into the rotor shaft member 323a correspondingly rotates in the roll direction "R".

On the other hand, the gear 322a engages with the gear 218 at right angle. Therefore, rotation operation in the pitch direction centering the rotor shaft 16 is converted into rotation operation centering the main shaft portion 320b orthogonal to the rotor shaft 16.

The gear 323 engages with the gear 322b formed on an opposite face of the gear 322a at right angle. The gear 323 is integrated with the rotor shaft member 323a, which is supported in the through-holes 321e and 321f in the roll member 321. Rotating operation of the gear 322b in the direction around the main shaft portion 320b is converted into rotating operation around the rotor shaft member 323a (rotor axis 26) in the yaw direction "Y". The treating member 325 is fittingly fixed to the rotor shaft member 323a and rotates integrally with the gear 323 in the yaw direction "Y".

In this way, when the wire 50b rotates the pulley 117a, in accordance with the rotation, the gears 117 and 321a and roll member 321 are rotated, thereby rotating the treating member 325 in the roll direction "R".

When the wire 50c rotates the pulley 218a, in accordance with the rotation, the gear 218, the gear member 322 and the gear 323 are rotated, thereby rotating the treating member 325 in the yaw direction "Y".

When the wire 50a rotates the pulley 320c, in accordance with the rotation, it is possible to rotate the main shaft portion 320b of the main shaft 320. As a result, it is possible to rotate the treating member 325 engaged with the main shaft 320b via the roll member 321 in the pitch direction "P".

The treating member 325 is composed of a metallic L-shaped hook and can treat the affected part by the treatment such as push or hanging for the affected part. Electricity can be conducted through the treating member 325 via the main body member 41 of the connecting portion 40 made of metal. This enables the treating member 325 to be used as an electric scalpel.

The wire 50a can be driven by the motor through manipulation of the pitch direction control manipulator 33 of the manipulating portion 30, described above with reference to FIG. 1. The wire 50c can be driven by the motor through manipulation of the yaw direction control manipulator 32. The wire 50b can be driven by the motor using a roll direction control manipulator (not shown) provided in the manipulating portion 30.

The manipulator 300 in accordance with the present embodiment also causes the mechanism interference described above in the third embodiment. Thus, taking the mechanism interference into account, the driving portion 35 (FIG. 1) controllably drives the wires 50a, 50b, and 50c on the basis of manipulation instructions from the manipulating portion 30.

In the manipulator 300 described above, the treating member 325 can change its position among the three degrees of freedom, that is, among a rotating operation in the direction around the rotor axis 29 (rotor shaft 16), a rotating operation in the direction around the rotor axis 26 (rotor shaft member 323a), and a rotating operation in the direction around the main axis 46 (main shaft portion 320b).

To achieve an a rotating operation in the direction around the rotor axis 29, a rotating operation around the rotor axis 26, and a rotating operation in the direction around the main axis 46, rotating direction is converted using the gears 117, 218, and 321a, the gear member 322, the gear 323, the roll member 321, and the main shaft member 320. This allows each of the wires 50a, 50b, and 50c to be most simply disposed using the corresponding pair of pulleys, the pulley 120c, 117a, or 218a and the corresponding driving pulley. Consequently, tension and unidirectional bending load are applied to each of the wires 50a, 50b, and 50c. This structure can thus suppress a decrease in the strength of the wires compared to complicatedly disposed wires. It also enables the use of wires of much smaller diameters. It can also simplify the manufacture process compared to complicatedly disposed wires.

Furthermore, the main shaft portion 320b of the main shaft member 320 which rotates in the pitch direction "P", supports both of the gear member 322 for rotating the treating member 325 in the yaw direction and the roll member 321 for rotating the treating member 325 in the yaw direction "Y". Therefore, compared with the case where each of support members is composed of separate parts, it is possible to reduce the number of parts, thereby realizing light-weight and simplified configuration.

By reducing the number of parts in this way, even when there is a limitation to the outer diameter of the manipulator, without downsizing each parts, while holding the strength of each parts, or by enhancing the strength with increase of the size of each parts, it is possible to provide the operating portion 110 in a limited space at the tip of the connecting portion 40, thereby sufficiently ensuring transmission torque and the strength. It is possible to simplify assembly operations by avoiding miniaturization of each parts.

The present embodiment uses the treating member 325 composed of an L-shaped hook. However, the present invention is not limited to this. The treating member 325 may have any of various shapes. For example, it may be shaped like a flat plate. The treating portion 325 may be adapted for various applications instead of being composed of an electric scalpel. For example, the treating portion 325 may be used for pushing, pulling, or cutting the affected part. The treating portions may also be detachable from the bearing member 323a and thus replaceable or may have its orientation arbitrarily varied.

Sixth Embodiment

Figure 34:
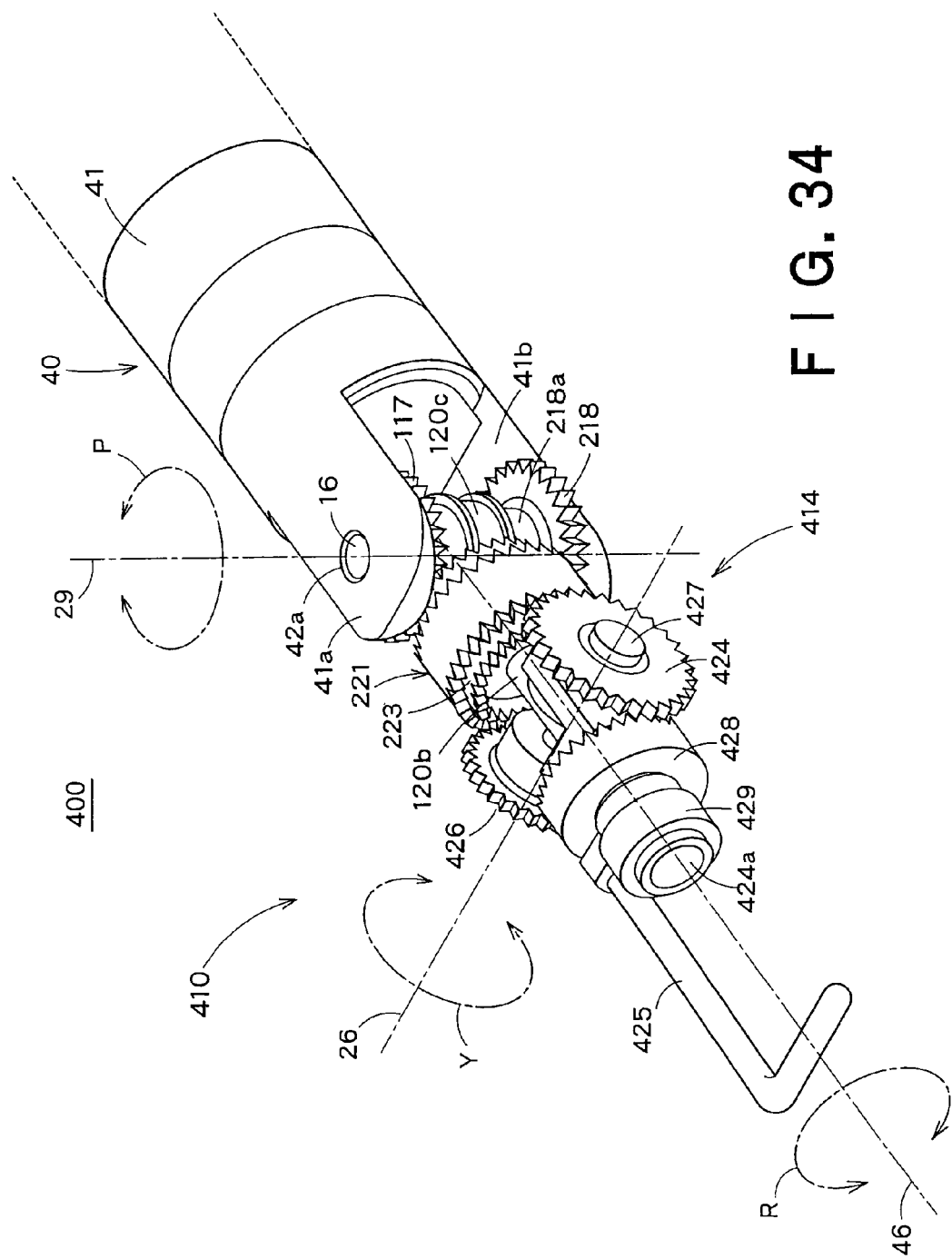
FIG. 34 is a perspective view showing the operating portion of the manipulator according to the sixth embodiment.
Figure 36:
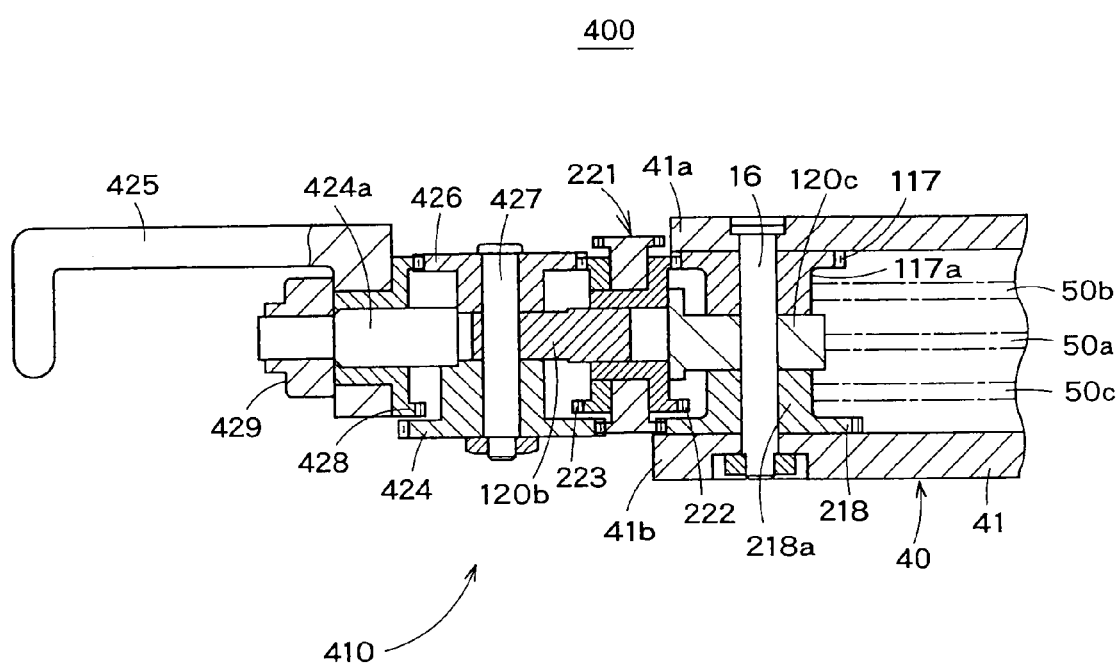
FIG. 36 is a cross-sectional view showing the operating portion of FIG. 34.

A manipulator 400 according to a sixth embodiment of the present invention is shown in FIGS. 34, 35, and 36 where components corresponding to those in FIGS. 28, 29, and 30 are denoted by the same reference numerals. The manipulator 400 includes the first rotor shaft 16 arranged orthogonal to the direction along the longitudinal direction of the connecting portion 40 at a tip of which a treating portion 425 is provided to treat the treatment target, the main shaft 120 which is rotatably supported in the direction around the first rotor shaft 16 (rotor axis 29) and has a main shaft portion 120b arranged orthogonal to the first rotor shaft 16, the first gear 117 rotatably supported in the direction around the first rotor shaft 16, the second gear 218 rotatably supported in the direction around the first rotor shaft 16, the third gear 222 which engages with the first gear 117 at right angle and is rotatably supported in the direction around the main shaft portion 120b, the fourth gear 221a which engages with the second gear 218 at right angle and is rotatably supported in the direction around the main shaft portion 120b, the fifth gear 223 which rotates coaxially and together with the third gear 222, the sixth gear 221b which rotates coaxially and together with the fourth gear 221a, a seventh gear 426 which engages with the fifth gear 223 at right angle, a second rotor shaft 427 which is rotation center of the seventh gear 426 and is located in a torsional relationship with the first rotor shaft 16, an eighth gear 424 which engages with the sixth gear 221b at right angle and rotates around the second rotor shaft 427 (rotor axis 26), a third rotor shaft 424a which crosses the second rotor shaft 427 at right angle and rotates in the direction around the second rotor shaft 427 together with the eighth gear 424, a ninth gear 428 which engages with the seventh gear 426 at right angle and rotates in the direction around the third rotor shaft 424a (main axis 46), and a treating member 425 which rotates in the direction around the third rotor shaft 424a together with the ninth gear 428. That is, the manipulator 400 includes the treating portion 425 that can rotate around the rotor axis 29, the rotor axis 26, and the main axis 46 so as to change its own position among three degrees of freedom. The cross-sectional view shown in FIG. 36 illustrates the first rotor shaft 16 and the second rotor shaft 427 arranged in torsional relationship by modifying them in parallel positions for convenience of explanation.

That is, the manipulator 400 includes the rotor shaft 16 constituting the rotor shaft (rotor axis 29) arranged orthogonal to the longitudinal direction (center axis direction) of the connecting portion 40, the two gears 117 and 218 arranged so as to be rotatable around the rotor shaft corresponding to the rotor axis 29, the main shaft 120 rotatably supported in the direction around the rotor shaft corresponding to the rotor axis 29, the gear 222 engaging with the gear 117 at right angle, the gear 223 provided coaxially and back to back with the gear 222 and rotating integrally with the gear 222, the gear 426 engaging with the gear 223 at right angle, the gear 428 which engages with the gear 426 and rotates in the direction around the main axis 46, the treating member 425 which is fixed to the gear 428 and rotates in the roll direction "R" together with the gear 428, the gear 221a which engages with the gear 218 at right angle, the gear 221b which is provided coaxially and back to back with the gear 221a and rotates integrally with the gear 221a, the gear 424 which engages with the gear 221b at right angle, and the treating member 425 which rotates around the rotor axis 26 integrally with the gear 424. The rotor shaft member 427, serving as a rotating center axis for the gears 426 and 424, constitutes the rotor axis 26 and is in a torsional or parallel relationship with the rotor axis 29. The rotor axis 29 (rotor shaft 16) and the rotor axis 26 (rotor shaft member 427) are offset from each other.

As shown in FIGS. 34, 35, and 36, the operating portion 410 of the manipulator 400 in accordance with the present embodiment includes the treating portion 425 which treats the affected part and a support portion 414 which supports the treating portion 425 so that the treating portion 425 can change its position among the three degrees of freedom.

The gears 117 and 218 and the main shaft 120 are rotatably supported on the rotor shaft 16 supported in the cylindrical main body member 41 of the connecting member 40.

The pulley 117a is integrated with the gear 117 concentrically with the rotating center of the gear 117. The gear 117 is rotated by driving the wire 50b (FIG. 36) hung around the pulley 117a. The pulley 218a is integrated with the gear 218 concentrically with the rotating center of the gear 218. The gear 218 is rotated by driving the wire 50c (FIG. 36) hung around the pulley 218a.

The main shaft 120 includes a bearing portion 120a rotatably supported around the rotor shaft 16 and the cylindrical main shaft portion 120b fixed to the bearing portion 120a so that its center axis is oriented in the radial direction. The pulley 120c is provided concentrically with the bearing portion 120a. The pulley 120c and the main shaft portion 120b are fixed together. By driving the wire 50a (FIG. 36) hung around the pulley 120c, the main shaft portion 120b can be rotated in the pitch direction shown in arrow "P" by centering the rotor shaft 16 (rotor axis 29).

The wires 50a, 50b, and 50c hung between the pulleys 117a, 218a, and 120c and the driving portion 35 (FIG. 1) are passed through the cylindrical main body portion 41 of the connecting portion 40. When the manipulating portion 30 manipulates these wires, the pulleys 117a, 218a, and 120c can be individually rotated around the rotor shaft 16.

The gears 222 and 223 and the gear member 221 are rotatably supported around the main shaft portion 120b of the main shaft 120. The gears 222 and 223 rotate integrally around the main shaft portion 120c. The gear 222 engages with the gear 117 at right angle. This converts a rotating operation around the rotor shaft 16 into a rotating operation centering the main shaft portion 120b orthogonal to the rotor shaft 16.

The gear member 221 includes the gears 221a and 221b arranged around the main shaft portion 120b and oriented in the direction an extension of center axis of the main shaft portion 120b. The gear member 221 has the gears 221a and 221b coaxially arranged on both end faces.

The gear 221a engages with the gear 218 at right angle. A rotating operation around the rotor shaft 16 in the pitch direction "P" is converted into a rotating operation in the roll direction "R" centering the main shaft portion 120b orthogonal to the rotor shaft 16.

The gear 424 engages with the gear 221b formed on a face opposite to the gear 221a at right angle. The gear 424 is rotatably supported around the rotor shaft member 427 constituting the rotor axis 26. The rotor shaft member 427 is supported in the thorough-hole 120d, formed in the main shaft portion 120b of the main shaft 120. The rotor shaft member 427 is prevented by a nut 427a from slipping out of the through-hole 120d. A rotating operation of the gear 221b around the main shaft portion 120b is thus converted into a rotating operation around the rotor shaft member 427 (rotor axis 26) in the yaw direction "Y".

The rotor shaft member 424a arranged orthogonal to the rotor axis 26 is fixed to the gear 424. The gear 428 is rotatably supported around the rotor shaft 424a. The gear 428 is prevented by a fixing member 429 from slipping off from the rotor shaft member 424a. The gear 428 thus maintains an appropriate engagement.

The gear 426 engages with the gear 223 at right angle. The gear 426 is rotatably supported around the rotor shaft member 427. The gear 428 engages with the gear 426 at right angle. A rotating operation of the gear 223 in the roll direction "R" is thus transmitted as a rotating operation of the gear 428 in the roll direction "R". The treating portion 425 is fixed to the gear 428. This causes the treating member 425 to be rotated integrally with the gear 428 in the roll direction "R".

Therefore, when the wire 50b rotates the pulley 117a, in accordance with the rotation, the gears 222, 223, 426 and 428 can be rotated, thereby rotating the treating member 425 in the roll direction "R".

When the wire 50c rotates the pulley 218a, in accordance with the rotation, the gear member 221, and the gear 424 rotates. This causes the rotor shaft member 424a to be rotated around the rotor shaft member 427 in the yaw direction "Y". Therefore, it is possible to rotate the treating member 425 supported to the rotor shaft 424a in the yaw direction.

When the wire 50a rotates the pulley 120c, in accordance with the rotation, it is possible to rotate the main shaft portion 120b of the main shaft 120 in the pitch direction "P". As a result, it is possible to rotate the treating member 425 engaged with the main shaft portion 120b via the rotor shaft 424a in the pitch direction.

The treating member 425 is composed of a metallic L-shaped hook and can treat the affected part; the treating member 425 can push or hang the affected part. Electricity can be conducted through the treating member 425 via the main body member 41 of the connecting portion 40 made of metal. This enables the treating member 425 to be used as an electric scalpel.

The wire 50a can be driven by the motor through manipulation of the pitch direction control manipulator 33 of the manipulating portion 30, as described above with reference to FIG. 1. The wire 50c can be driven by the motor through manipulation of the yaw direction control manipulator 32. The wire 50b can be driven by the motor using the roll direction control manipulator (not shown) provided in the manipulating portion 30.

The manipulator 400 in accordance with the present embodiment also causes the mechanism interference described above in the third embodiment. Thus, taking the mechanism interference into account, the driving portion 35 (FIG. 1) controllably drives the wires 50a, 50b, and 50c on the basis of manipulation instructions from the manipulating portion 30.

In the manipulator 400 described above, the treating member 425 can change its position among the three degrees of freedom, that is, among a rotating operation in the direction around the rotor axis 29 (rotor shaft 16), a rotating operation around the rotor axis 26 (rotor shaft member 427), and a rotating operation around the main axis 46 (rotor shaft 120b).

To achieve an a rotating operation around the rotor axis 29, a rotating operation in the direction around the rotor axis 26, and a rotating operation in the direction around the main axis 46, the rotating direction is converted using the gears 117, 218, and 222, the gear member 221, the gears 223, 424, 426, and 428, the main shaft 120, and the rotor shaft member 424a. This allows each of the wires 50a, 50b, and 50c to be most simply disposed using the corresponding pair of pulleys, the pulley 120c, 117a, or 218a and the corresponding driving pulley. Consequently, tension and unidirectional bending load are applied to each of the wires 50a, 50b, and 50c. This structure can thus suppress a decrease in the strength of the wires compared to complicatedly disposed wires. It also enables the use of wires of much smaller diameters. It can also simplify the manufacture process compared to complicatedly disposed wires.

Furthermore, the main shaft portion 120b of the main shaft 120 which rotates in the pitch direction "P", supports the gear 424 for rotating the treating member 425 in the yaw direction "Y", the rotor shaft member 424a, and the gears 426 and 428 for rotating the treating member 425 in the roll direction "R". Therefore, compared with the case where each of support members is composed of separate parts, it is possible to reduce the number of parts, thereby realizing light-weight and simplified configuration.

By reducing the number of parts in this way, even when there is a limitation to the outer diameter of the manipulator, without downsizing each parts, while holding the strength of each parts, or by enhancing the strength with increase of the size of each parts, it is possible to provide the operating portion 110 in a limited space at the tip of the connecting portion 40, thereby sufficiently ensuring transmission torque and the strength. It is possible to simplify assembly operations by avoiding miniaturization of each parts.

With the manipulator 300 according to the fifth embodiment described above in FIGS. 31 to 33, if the rotor axis 29 (rotor shaft 16) is parallel to the rotor axis 26 (rotor shaft member 323a), rotation operation in orthogonal direction becomes difficult due to a singular position. In contrast, with the manipulator 400 according to the present embodiment, the main axis 46 (rotor shaft 424a) is located in the rotor shaft member 424a, serving as a tip shaft. This makes it possible to avoid a singular configuration and thus degradation of manipulability.

The present embodiment uses the treating member 425 composed of an L-shaped hook. However, the present invention is not limited to this. The treating member 425 may have any of various shapes. For example, it may be shaped like a flat plate. The treating portion 425 may be adapted for various applications instead of being composed of an electric scalpel. The treating portion 425 may be used for pushing, pulling, or cutting the affected part. The treating portions may also be detachable from the rotor shaft member 424a for replacement or may have its orientation arbitrarily varied.

Figure 39:
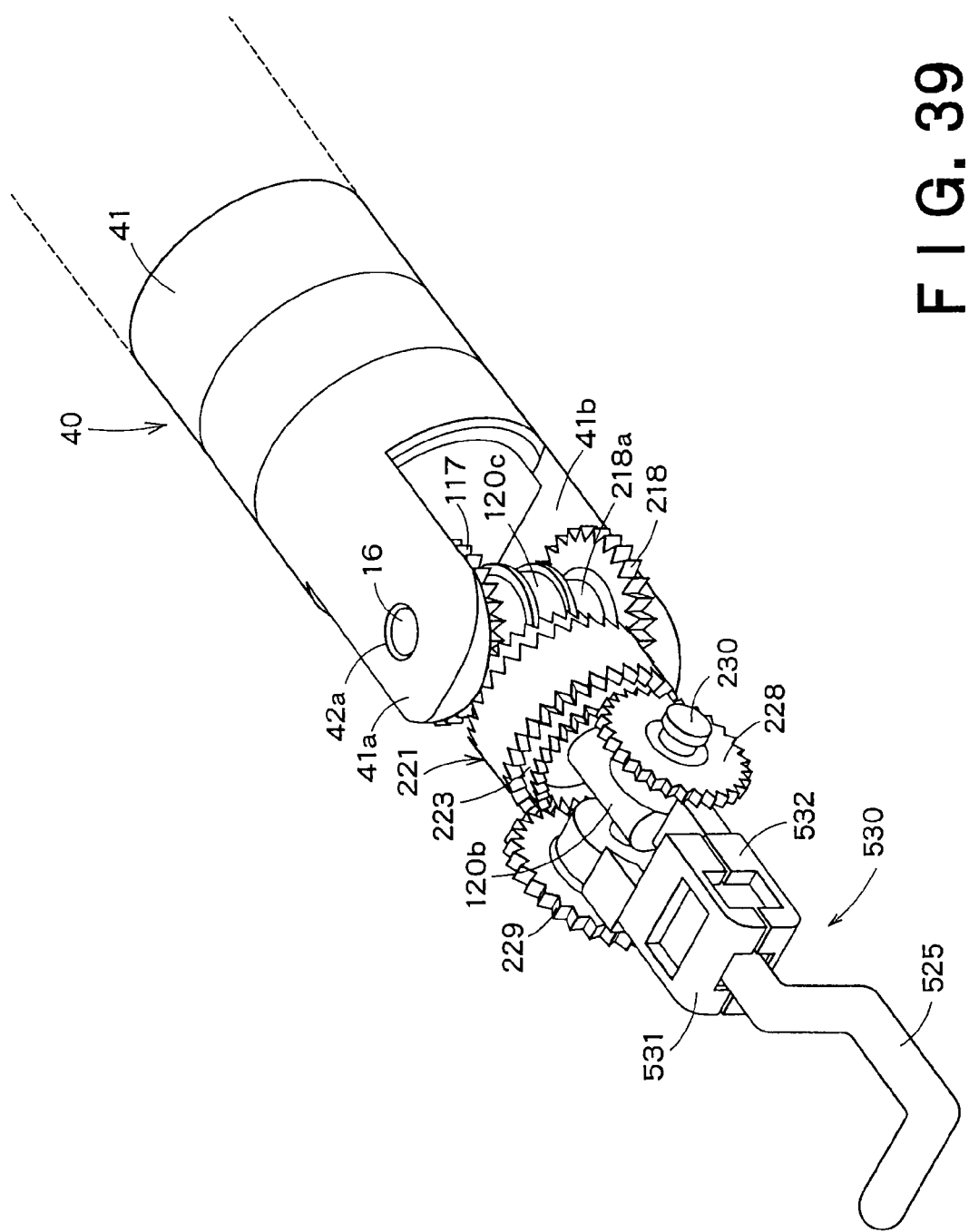
FIG. 39 is a perspective view showing the operating portion of the manipulator according to the other embodiment.

In the description of the above embodiments, the treating members (grippers) are fixed to the gear or the like. However, the present invention is not limited to this. For example, as shown in FIGS. 37 to 39 where components corresponding to those in FIGS. 28 to 30 are denoted by the same reference numerals, a gripping portion 530 (gripping portions 531 and 532) opened and closed by the gears 228 and 229 may be used to grip a gripped portion 525a of a treating portion 525. This makes it possible to easily change the orientation of the treating member 525 and to easily replace the treating portion with any of various others with different shapes. In this case, the initial position of the treating member 525 can be easily changed. An operation can thus be started with the treating portion gripped in a direction in which the treating portion can be appropriately manipulated. This significantly improves manipulability. Furthermore, it is possible to easily exchange the treating member tainted by the operation with a new treating member.

Seventh Embodiment

A seventh embodiment is a variation of the fifth embodiment in which the structure of the treating member is different from that in the fifth embodiment.

Figure 40:
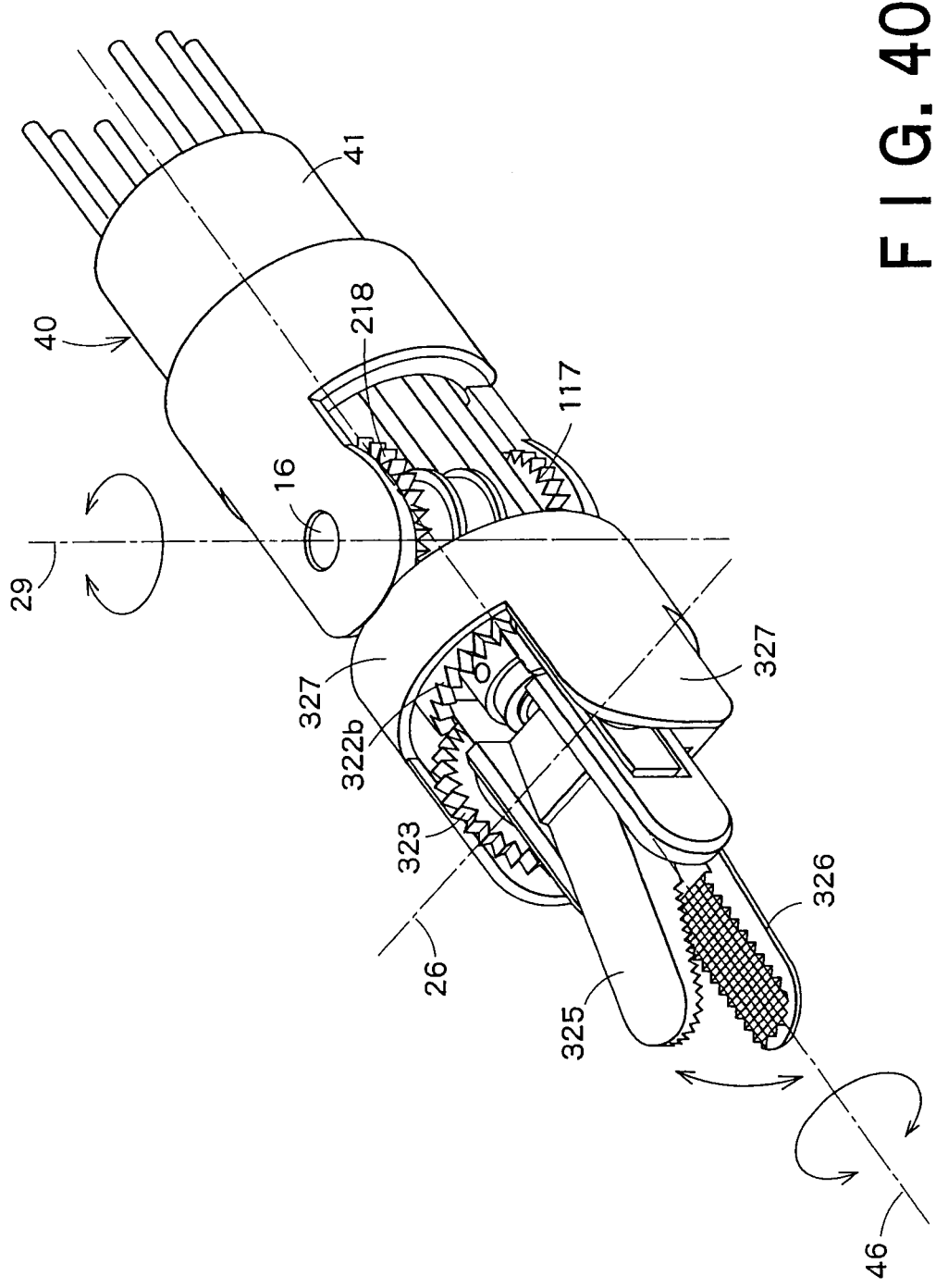
FIG. 40 is a perspective view showing the operating portion according to the seventh embodiment of the present invention.

FIG. 40 is a perspective view showing an operating portion of a manipulator in accordance with the seventh embodiment of the present invention. FIG. 41 is an exploded perspective view showing the operating portion of FIG. 40. The manipulator in FIG. 40 includes the connecting portion 40 at a tip of which the first treating portion 325 and a second treating portion 326 are provided to treat a treatment target, and which treats the treatment target, the first rotor shaft 16 arranged orthogonal to the direction along the longitudinal direction of the connecting portion 40, the main shaft member 320 which is rotatably supported around the first rotor shaft 16 (rotor axis 29) and has the main shaft portion 320b orthogonal to the first rotor shaft 16, the first gear 117 rotatably supported in the direction around the first rotor shaft 16, and the second gear 218 rotatably supported in the direction around the first rotor shaft 16.

The manipulator in FIG. 40 also includes the third gear 321a which engages with the first gear 117 at right angle and is rotatably supported around the main shaft portion 320b, the fourth gear 322a which engages with the second gear 218 at right angle and is rotatably supported around the main shaft portion 320b, the second rotor shaft 321b which rotates coaxially and together with the third gear 321a, and the fifth gear 322b which rotates coaxially and together with the fourth gear 322a.

The manipulator in FIG. 40 further includes the third rotor shaft 323a which crosses the second rotor shaft 321b (main axis 46) at right angle and rotates around the main shaft portion 320b in conformity to rotation of the second rotor shaft 321b. The third rotor shaft 323a is located so as to be rotatable from a torsional position to a parallel position with respect to the first rotor shaft 29.

The manipulator in FIG. 40 further includes the sixth gear 323 which is rotatably supported in the direction around the third rotor shaft 323*a* and engages with the fifth gear 322*b* at right angle, the first treating member 325 which rotates in the direction around the second rotor shaft 321*b* and also rotates in the direction around the third rotor shaft 323*a* together with the sixth gear 323, and the second treating member 326 which rotates in conformity to the third gear 321*a* and second rotor shaft 321*b*.

The first treating member 325 and second treating member 326 constitute a pair of treating members. The first treating member 325 rotates in the direction around the third rotor shaft 323*a* so as to constitute a gripping mechanism which is opened and closed relative to the second treating member 326.

In this way, the manipulator 300 in FIG. 40 includes the treating portions 325 and 326 having the opening and closing mechanism (gripping mechanism: grippers) which can change its own position between two degrees of freedom using the rotor axis 29 (rotor shaft 16) and the main axis 46 (main shaft member 321*b*) as rotating centers.

A fixed nut 1 is fixed to a threaded portion at the tip of the main shaft member 320*b* to restrict the positions in the axis direction of the third gear 321*a* and the main shaft member 320*b* of the second rotor shaft 321*b*. A fixed nut 2 restricts the positions in the axis direction of the third rotor axis 323*a* and the third rotor axis 323*a* of the sixth gear 323.

A cover 327 minimizes the exposure of the gears and is fixed to the bottom of the second treating member 326 using a cover fixing pin 328. The cover 327 rotates in the direction around the second rotor shaft 321*b* (main axis 46) in conformity to the second treating member 326.

Eighth Embodiment

An eighth embodiment integrates a plurality of gears together to reduce the size of the manipulator and the number of parts required.

Figure 42:
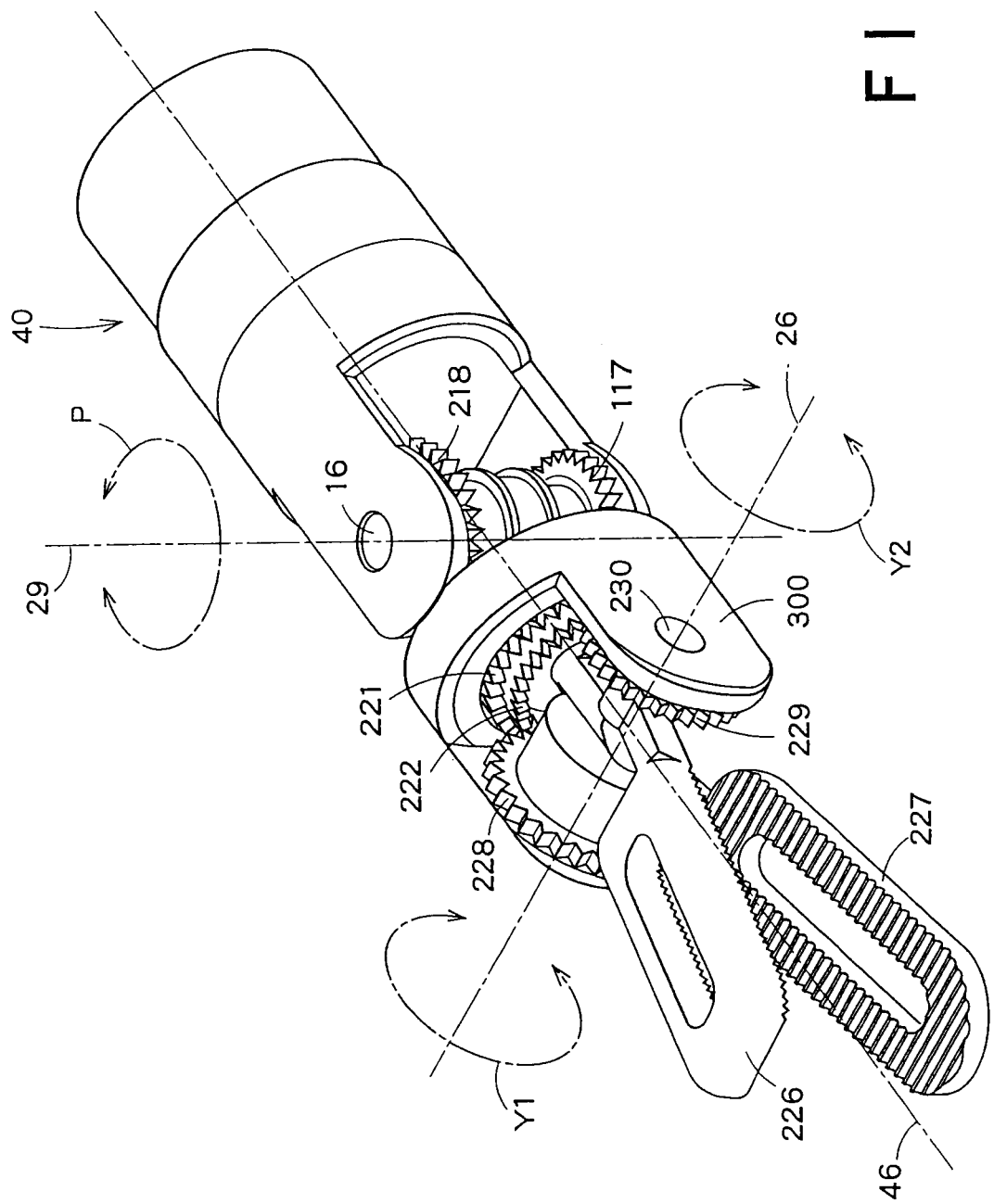
FIG. 42 is a perspective view showing the operating portion of the manipulator according to the eighth embodiment of the present invention.
Figure 44:
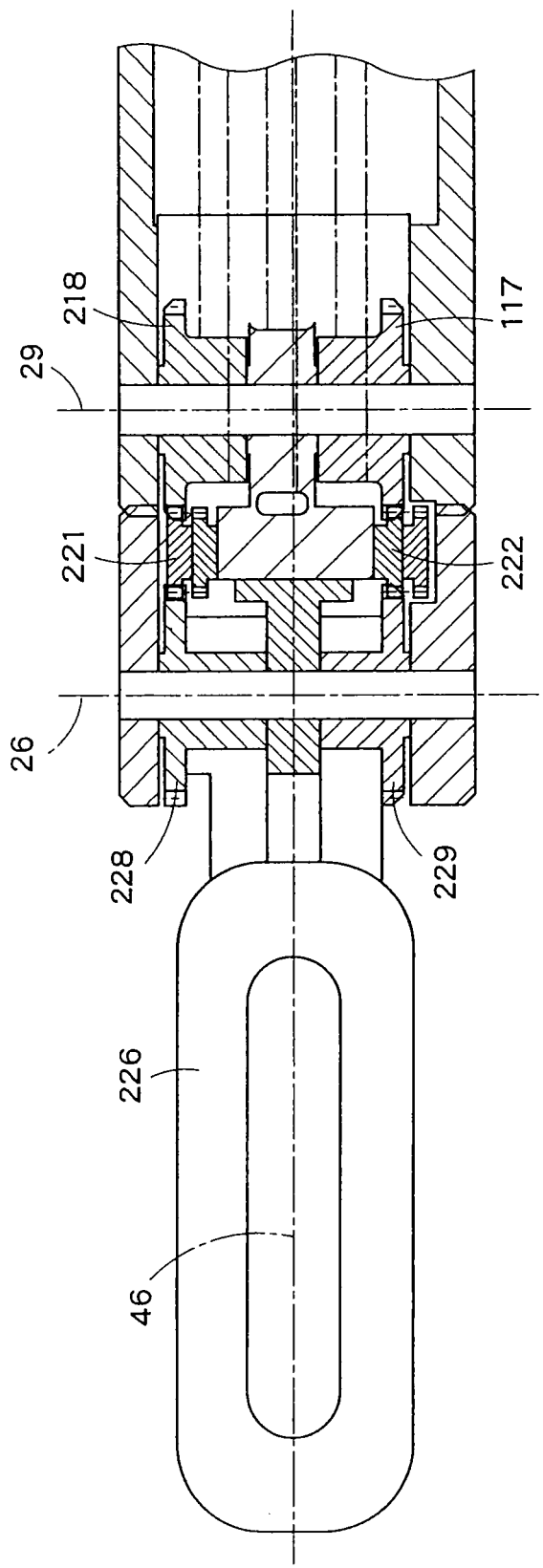
FIG. 44 is a cross-sectional view showing the operating portion.

FIG. 42 is a perspective view showing an operating portion of a manipulator according to an eighth embodiment of the present invention. FIG. 43 is an exploded perspective view showing the operating portion of FIG. 42. FIG. 44 is a sectional view showing the operating portion. The manipulator of the present embodiment has a mechanism similar to that of the manipulator shown in FIGS. 28 to 30. Accordingly, members common to FIGS. 28 to 30 are denoted by the same reference numerals. Differences from the manipulator shown in FIGS. 28 to 30 will be mainly described below. The cross-sectional view shown in FIG. 44 illustrates the first rotor shaft 16 and the second rotor shaft 230 arranged in torsional relationship by modifying them in parallel positions for convenience of explanation.

The manipulator according to the present embodiment includes the first rotor shaft 16 which crosses to the direction along the longitudinal direction of the connecting portion 40 at a tip of which the first and second treating portions 226 and 227 is provided, the main shaft 120 rotatably supported in the direction around the first rotor shaft 16 (rotor axis 29) orthogonal to the first rotor shaft 16, the first gear 117 rotatably supported in the direction around the first rotor shaft 16, the second gear 218 rotatably supported in the direction around the first rotor shaft 16, a third gear 222*a* which engages with the first gear 117 at right angle and is rotatably supported in the direction around the main shaft 120, the fourth gear 221*a* which engages with the second gear 218 at right angle and is rotatably supported around the main shaft 120, a fifth gear 222*b* which is integrated with the third gear 222*a* and rotates coaxially and together with the third gear 222*a*, a sixth gear 221*b* which is integrated with the fourth gear 221*a* and rotates coaxially and together with the fourth gear 221*a*, the seventh gear 229 which engages with the fifth gear 222*b* at right angle, the eighth gear 228 which engages with the sixth gear 221*b* at right angle, the second rotor shaft 230 which is rotation center of the seventh gear 229 and the eighth gear 228, and is located in a torsional relationship with the first rotor shaft 16, the first treating member 226 which rotates in the direction around the second rotor shaft 230 (rotation axis 26) together with the seventh gear 229, and the second treating member 227 which rotates in the direction around the second rotor shaft 230 together with the eighth gear 228.

The first gear member 222 having the third gear 222*a* and the fifth gear 222*b* has the same rotating axis as that of the second gear member 221 having the fourth gear 221*a* and the sixth gear 221*b*. The first gear member 222 and the second gear member 221 are arranged so as to overlap in the radial direction.

In the case of the structure of FIG. 29, the gear 222 has to be combined with the gear 223. Therefore, in order to stably combine them, the structure requires the parts to be precisely machined. For example, the "D" hole in the gear 222 and the "D" cut in the gear 223 need to be very precisely formed.

In contrast, in the present embodiment, the first gear member 221 on which the third gear 222*a* and the fifth gear 222*b* are integrally formed, and the second gear member 222 on which the fourth gear 221*a* and the sixth gear 221*b* are integrally formed. Therefore, adjustment of backlash in this area is principally unnecessary. The gear members 221 and 222 also have simple cylindrical shapes except the gear portions, thereby simplifying manufacturing and assembly.

Ninth Embodiment

In the manipulator shown in FIGS. 42 to 44, the first gear 117 and second gear 218 which rotate in the direction around the first rotor shaft 29, may be formed using the same pitch circle diameter. The seventh gear 229 and eighth gear 228 may also be formed using the same pitch circle diameter.

Generally, a module "m" is defined as a value obtained by dividing the pitch circle diameter "d" of a gear by the number "z" of teeth, i.e. m=d/z. The module is used to represent the size of the gear. The module is used as an important reference in selecting a gear or designing a gear mechanism. The larger the value of the module is, the larger the size of teeth is. A pair of engaged gears does not function appropriately unless the gears have the same tooth size (that is, the same module).

In order to equalize the pitch circle diameter of two gears, values obtained by multiplying the module by the number of teeth have to be equal. For example, a pair of the number of teeth may be equal, and the modules may be equal. It is unnecessary that the modules are equal and the number of teeth is also equal. However, if the number of teeth is equal, the same gears can be used, thereby reducing cost of manufacturing.

In FIG. 43, if a pair of the number of teeth are equal and the modules are also equal, it is possible to conform center points of the pitch circles in the third gear 222*a* and the fourth gear 221*a*, and to conform center points of the pitch circles in the fifth gear 222*b* and the sixth gear 221*b*. Therefore, it is possible to shorten a length in the axis direction of the third gear 222*a* and the fifth gear 222*b*, and to shorten a length in the axis direction of the fourth gear 221*a* and the sixth gear 221*b*.

As a result, it is possible to shorten a distance between the rotor axis 26 in the yaw direction and the rotor axis 29 in the pitch direction, it is possible to reduce the offset amount, and it is possible to obtain almost ideal location relationship in which the rotor axis 26 is orthogonal to the rotor axis 29. Therefore, it is possible to easily guide the treating member such as the first and second treating portions 226 and 227 in an intermediate direction between the rotor axis 26 and the rotor axis 27.

Furthermore, since it is possible to reduce the offset amount, it is possible to reduce a burden of a joint torque in the rotor axis 29 for a load around the rotor axis 29 due to an external force acting on the treating portion.

Furthermore, the first gear 117 is beveled so as to prevent its tip from interfering with the fourth gear 221a. The second gear 218 need not be beveled in terms of the interference. However, if the second gear 218 is also beveled, the number of parts required and costs can be reduced because the same gear can be used for both the first gear 117 and the second gear 218.

The modularization described above in the ninth embodiment is applicable not only to the manipulator in FIGS. 42 and 43 but also to all the other embodiments.

Tenth Embodiment

For example, in the case of the manipulator in FIG. 43, transmission efficiency varies depending on the position where the first gear 117 and third gear 222 are engaged and the position where the fifth gear 222b and seventh gear 229 are engaged. Likewise, transmission efficiency varies depending on the position where the second gear 218 and fourth gear 221 are engaged and the position where the sixth gear 221b and eighth gear 228 are engaged. Thus, a tenth embodiment adjusts the gear engagement position so as to improve the transmission efficiency.

Figures 45A, 45B, 45C:
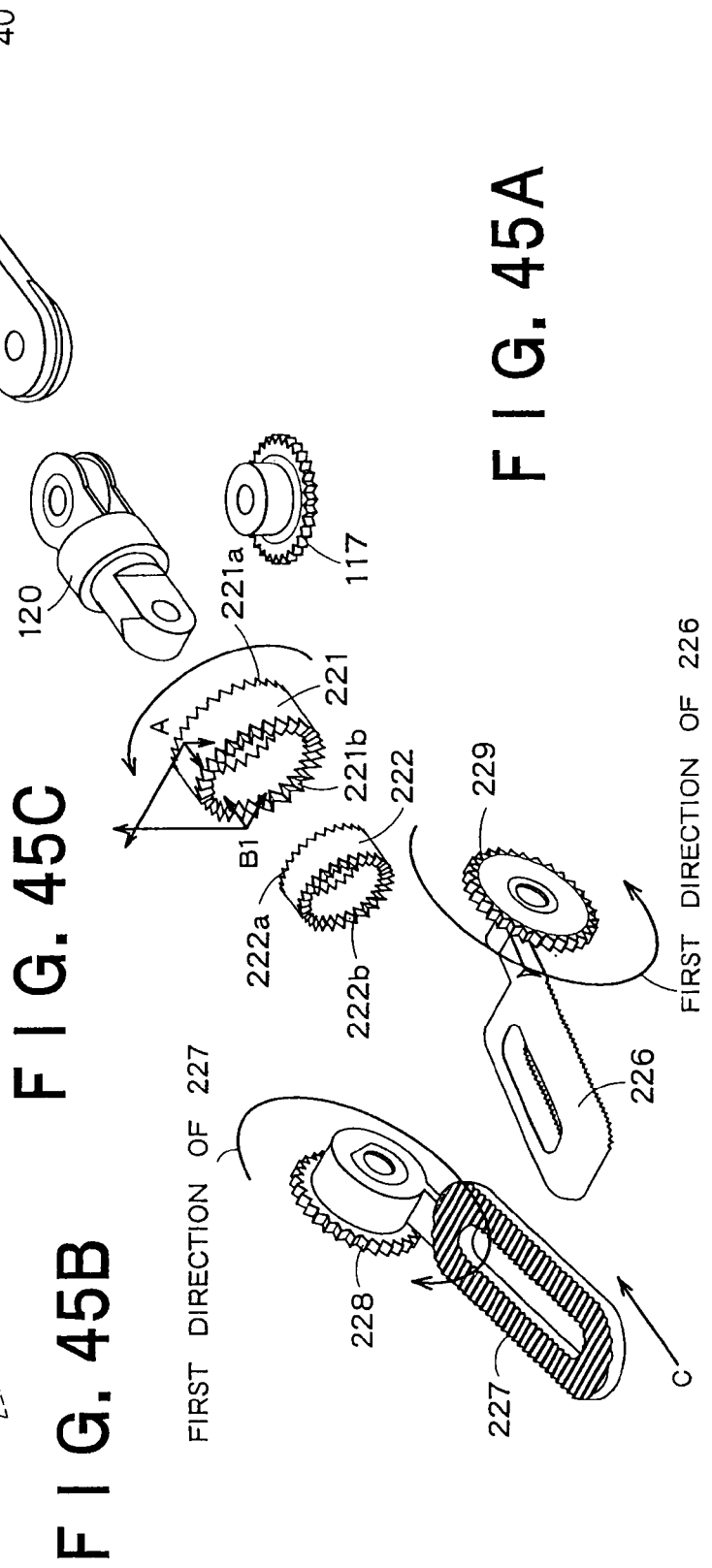
FIG. 45A is an exploded perspective view of the manipulator having the same structure as that of FIG. 43.
FIG. 45B is a view seen from the thrust direction (C direction) of the second gear member.
FIG. 45C is a view schematically showing force transmitting paths.

FIG. 45A is an exploded perspective view of a manipulator having a structure similar to that shown in FIG. 43. To drive the first treating member 226 of the manipulator in FIG. 45A in a first direction (gripping direction), the engagement position between the first and third gears 117 and 222a and the engagement position where the fifth and seventh gears 222b and 229 are set so as to be separated from the rotating direction of the first gear member 222 by an amount corresponding to a phase of 0 to 180☐. To drive the first treating member 226 in a second direction (opening direction) opposite to the first direction, the engagement position between the first and third gears 117 and 222a and the engagement position where the fifth and seventh gears 222b and 229 are set so as to be separated from the rotating direction of the first gear member 222 by an amount corresponding to a phase of 180 to 360☐. More specifically, the engagement position between the fifth and seventh gears 222b and 229 is adjusted to meet the above phase relationships.

To drive the second treating member 227 in the first direction (gripping direction), the engagement position between the second and fourth gears 218 and 221a and the engagement position where the sixth and eighth gears 221b and 228 are set so as to be separated from the rotating direction of the second gear member 221 by an amount corresponding to a phase of 0 to 180☐. To drive the second treating member 227 in a second direction (opening direction) opposite to the first direction, the engagement position between the second and fourth gears 218 and 221a and the engagement position where the sixth and eighth gears 221b and 228 are set so as to be separated from the rotating direction of the second gear member 221 by an amount corresponding to a phase of 180 to 360☐. More specifically, the engagement position between the sixth and eighth gears 221b and 228 is adjusted to meet the above phase relationships.

Description will be given with reference to the reason why the gears are desirably arranged so as to meet the above phase relationship. In FIG. 45A, the engagement position between the sixth and eighth gears 221b and 228 corresponds to the engagement position between the second and fourth gears 218 and 221a as rotated through 90° toward the rotating direction of the second gear member 221 (load direction by gripping).

The second treating member 227 is driven in a gripping direction, that is, a high load direction, when the second gear 218 rotates in the direction of an arrow in FIG. 45A.

On the other hand, in FIG. 46A, the engagement position between the sixth and eighth gears 221b and 228 corresponds to the engagement position between the second and fourth gears 218 and 221a as rotated through 270° toward the rotating direction (load direction by gripping) of the second gear member 221.

The second treating member 227 is driven in the gripping direction, that is, the high load direction, when the second gear 218 rotates in the direction of an arrow in FIG. 46A.

FIGS. 45A and 46A show reaction forces received from the second and eighth gears 218 and 228 by the second gear member 221.

The force acting on a gear is normally divided into three components, a tangential (torque transmitting direction) component that is a main component, a thrust-directional component attributed to the pressure angle of the gear or the angle of the teeth, and a radial component.

FIGS. 45B and 46B show the second gear member 221 as viewed from the thrust direction ("C" direction in the figures). The three components provide a force received from the second gear 218 by the second gear member 221, a force received from the eighth gear 228 by the second gear member 221, a radial force, and a force balanced with these forces, that is, a reaction force received by the second gear member 221 from the main shaft 120 via the second gear member.

A comparison of FIG. 45B with FIG. 46B clearly indicates that the reaction force in FIG. 45B is much weaker than that in FIG. 46B. The reaction force corresponds to a vertical reaction force to the frictional torque of the second gear member 221. Accordingly, the magnitude of the frictional torque is in proportion to the magnitude of the reaction force to the frictional torque.

FIGS. 45C and 46C schematically show force transmitting paths. In FIG. 45C, there is a phase difference of 90° between the engagement position between the second and fourth gears 218 and 221a and the engagement position between the sixth and eighth gears 221b and 228 in the force transmitting direction. In FIG. 46C, the phase difference is 270° in the force transmitting direction.

Thus, the force transmitting path in FIG. 46C is longer than that in FIG. 45C. If the main shaft 120b, second gear member 221, and second gear member 218 have ideal shapes, there should be no difference in torque transmission between these force transmitting paths. However, an error component of the actual dimensions may cause back-lash, which may tilt the gear. The tilted gear may abut only partly against the corresponding element. This may increase the magnitudes of the frictional torque and the reaction forces other than the tangential (torque transmitting direction) one. Therefore, torque transmission may not be ideal.

In particular, owing to the longer force transmitting path, the structure in FIG. 46C is likely to be affected by the tilt of the gear caused by back-lash or the like. This significantly reduces transmission efficiency. In contrast, owing to the shorter and linear force transmitting path, the structure in FIG. 45C is unlikely to be affected by the tilt of the gear caused by back-lash or the like. This structure can thus transmit torque both directly and efficiently.

In the above-described embodiment, the first treating member 226 and the second treating member 227 have the structures capable of conducting the gripping operation by individually driving them around the second rotor axis 226. However, if the manipulator including at least one or more gear structure similar to that of the present embodiment is used, the same advantageous effect will be obtained even in the other embodiment besides the present embodiment.

For example, as shown in FIG. 40, even in the structure capable of conducting the gripping operation by driving only the first treating member 325, with respect to the second gear 218, the fourth gear 332a, the fifth gear 332b and the sixth gear 323 for driving the first treating member 325, it is possible to obtain the same advantageous effect by arranging the engaging position between the second gear 218 and the fourth gear 332a and the engaging position between the fifth gear 332b and the sixth gear 323 in the same way as the present embodiment.

In other words, when the treating member is driven in the first direction (the direction of high load, for example, gripping direction), it may be desirable that the engaging position at which the second gear 218 engages with the fourth gear 322a and the engaging position at which the fifth gear 322b engages with the sixth gear 323 are arranged within phase 0° to 180° for rotation direction of the fifth gear 322b.

In the above embodiments, the treating portion may not necessarily be electrically driven but may be mechanically driven. Moreover, the present invention is applicable to a gripping forceps, a releasing forceps, an excluding forceps, a scissor forceps, an electric scalpel, an ultrasonic scalpel or the like.

The above embodiments have been described in conjunction with the manipulator which integrates the operating portion, the driving portion, the connecting portion and the treating portion directly operated by the operator. However, the structure of the manipulator is not limited to the above embodiments. The present invention is applicable to the other manipulators having a separated operating portion, a structure supported at multiple degree of freedom, a structure which is arranged at a tip of a slave and is controlled remotely.

The above embodiments have been described in conjunction with the medical manipulator. However, the present invention is not limited to this and is applicable to various manipulators such as one that deals with the inside of energy equipment.

In the above-described embodiments, the rotor shaft may be rotated in the direction of the rotor axis at a state integrated with the rotor portions such as the other rotor shaft and the gear, or the structure having the fixed axis.

The invention claimed is:

1. A manipulator, comprising:
a first rotor axis portion which crosses to a direction along a longitudinal direction of a connecting portion at a tip of which a treating portion is provided to treat a treatment target;
a main shaft portion which is rotatably supported around the first rotor axis portion such that the first rotor axis portion is a rotational pivot axis about which the main shaft portion rotates;
a first treating member and a second treating member which are provided in the treating portion;
a first gear rotatably supported in the direction around the first rotor axis;
a second gear rotatably supported in the direction around the first rotor axis;
a third gear which engages with the first gear and is rotatably supported around the main shaft portion;
a fourth gear which engages with the second gear and is rotatably supported around the main shaft portion;
a fifth gear which coaxially rotates with the third gear;
a sixth gear which coaxially rotates with the fourth gear;
a seventh gear which is provided to transmit rotation torque of the fifth gear to the first treating member and engages with the fifth gear;
an eighth gear which is provided to transmit rotation torque of the sixth gear to the second treating member and engages with the sixth gear; and
a second rotor axis portion which is a rotation center of the seventh gear and the eighth gear and is arranged in a torsional relationship with the first rotor axis portion.

2. The manipulator according to claim 1, wherein the first and second treating members constitutes a gripper portion which conducts open and close operations in accordance with rotations of the seventh and eighth gears.

3. The manipulator according to claim 1, wherein the second rotor axis portion is orthogonal to a surface including the first rotor axis and the main shaft portion.

4. The manipulator according to claim 1, wherein the fourth gear and the sixth gear share a common base.

* * * * *